United States Patent
Anversa et al.

(10) Patent No.: US 9,534,204 B2
(45) Date of Patent: Jan. 3, 2017

(54) HUMAN LUNG STEM CELLS AND USES THEREOF

(75) Inventors: Piero Anversa, Boston, MA (US); Annarosa Leri, Boston, MA (US)

(73) Assignee: AAL Scientifics, Inc., New York, NY (US)

( * ) Notice: Subject to any disclaimer, the term of this patent is extended or adjusted under 35 U.S.C. 154(b) by 0 days.

(21) Appl. No.: 13/877,381

(22) PCT Filed: Oct. 5, 2011

(86) PCT No.: PCT/US2011/054849
§ 371 (c)(1),
(2), (4) Date: May 14, 2013

(87) PCT Pub. No.: WO2012/047951
PCT Pub. Date: Apr. 12, 2012

(65) Prior Publication Data
US 2013/0216508 A1    Aug. 22, 2013

Related U.S. Application Data

(60) Provisional application No. 61/389,737, filed on Oct. 5, 2010.

(51) Int. Cl.
*A61K 35/42* (2015.01)
*C12N 5/071* (2010.01)
*A61K 45/06* (2006.01)

(52) U.S. Cl.
CPC ............. *C12N 5/0689* (2013.01); *A61K 35/42* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,547,674 B2 | 6/2009 | Anversa et al. | |
| 2008/0292677 A1 | 11/2008 | Cortiella et al. | |
| 2009/0148421 A1 | 6/2009 | Anversa et al. | |
| 2009/0162329 A1 | 6/2009 | Anversa et al. | |
| 2009/0180998 A1 | 7/2009 | Anversa et al. | |

FOREIGN PATENT DOCUMENTS

| | | |
|---|---|---|
| WO | WO 2007124594 A1 * | 11/2007 |
| WO | WO2007149447 A2 | 12/2007 |

OTHER PUBLICATIONS

Cortiella, Joaquin; et al; "Tissue-Engineered Lung: An In Vivo and In Vitro Comparison of Polyglycolic Acid and Pluronic F-127 Hydrogel/Somatic Lung Progenitor Cell Constructs to Support Tissue Growth" Tissue Engineering, 12, 1213-1225, 2006.*
Christie et al., J Heart Lung Transplant, 28:1031-49 (2009). "The registry of the international society for heart and lung transplantation: twenty-sixth official adult lung and heart-lung transplantation report—2009."
Kajstura et al., N Engl J Med, 364(19):1795-1806 (2011). "Evidence for human lung stem cells."
Bearzi et al., PNAS, 104(35):14068-14073 (2007). "Human cardiac stem cells."
Bender-Kim et al., Cell, 121(6):823-835 (2005). "Identification of bronchioalveolar stem cells in normal lung and lung cancer."
Kotton et al., Cell Tissue Res, 331(1):145-156 (2008). "Lung stem cells."
Kotton et al., Experimental Hematology, 32(4):340-343 (2004). "Lung stem cells: new paradigms."
Sandstedt et al., Basic Res Cardiol, 105(4):545-556 (2010). "C-kit+ CD45- cells found in the adult human heart represent a population of endothelial progenitor cells."
Hua, J. et al., Tissue and Cell 41(6):448-455 (Aug. 3, 2009).

\* cited by examiner

Primary Examiner — Taeyoon Kim
Assistant Examiner — David Berke-Schlessel

(57) ABSTRACT

Embodiments of the invention relate to human stem cells and their therapeutic use in the treatment and/or prevention of lung diseases. Provided herein are compositions comprising c-kit positive human lung stem cells and methods of preparing and using c-kit positive human lung stem cells for the treatment and/or prevention of lung diseases.

8 Claims, 17 Drawing Sheets

SEQUENCE LISTING

<160> NUMBER OF SEQ ID NOS: 39

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
agaaggagat tactgctctg gctc                                          24

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
acatctgctg gaaggtggac a                                             21

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
caaggactgg tctttctatc tcttg                                  25

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
attcatccaa tccaaatgcg                                        20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcacctgctg aaatgtatga cataat                                 26

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctgcagtttg ctaagttgga gtaaat                                 26

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aggagaagct ggagcaaaa                                         19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggctgaatac cttcccaaa                                         19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

```
ggtcccggtc aagaaacaga                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaggttcagg atgttggaga                                              20

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ccagctcgca gacctaca                                                18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cctggagtgg gaggaaga                                                18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gacttccccc agtgcttc                                                18

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgttgaactc ctcggtctc                                               19

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
```

```
aaagcagcaa gtttcggaca gtac                                              24

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccagggactc tttgatcttc aacag                                             25

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agggcgagga atgcagactc                                                   20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgctacctcc ggcaagacct                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
catgaggaac agcgcctctg                                                   20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tcaccctcac cctggtcaca                                                   20

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ggtgtccacc agcttcttca gc                                                22
```

```
<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cactggcctc gtggtgtatg                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cctgcagaga gcattccatc                                              20

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaagcaatgc tggaatgcca ac                                           22

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cttgcttgag ttccggtggg                                              20

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctggaagatg gcgaggactt taatc                                        25

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtaccctgc ttctgctgg                                               19
```

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cagtccacgc gcaagaacaa ag                                              22

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcaccaatga agccgatggc                                                 20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gtccattggc ctgtctgtca cc                                              22

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gagttgggga agagcaggta gaag                                            24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctatcaaac aagaagtcgt cacc                                            24

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gaagctgtca taggagggaa ca                                              22

```
<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
taaagagcct ctgaactcag acg                                              23

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
catctggcct tgctgtctaa g                                                21

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caaaccacag agtgggaaca                                                  20

<210> SEQ ID NO 37
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tacaagatca taataaggca gttgg                                            25

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tttttttttt ttttt                                                       15

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgcccatgcc gctcatg                                                     17
```

HUMAN LUNG STEM CELLS AND USES THEREOF

CROSS REFERENCE TO RELATED APPLICATIONS

This application is a 35 U.S.C. §371 National Phase Entry Application of International Application No. PCT/US2011/054849 filed Oct. 5, 2011, which designates the U.S., and which claims benefit under 35 U.S.C. §119(e) of the U.S. Provisional Application No. 61/389,737 filed on Oct. 5, 2010, the contents of which are incorporated herein by reference in their entireties.

GOVERNMENT SUPPORT

This invention was made with Government support under Grant No.: P01 HL092868; R01 HL 065577; 5R01HL060788; and P01 HL092868 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Mar. 28, 2013, is named 043214068122_SequenceListing.txt and is 9,098 bytes in size.

BACKGROUND OF INVENTION

Every year over 400,000 Americans die from some type of lung disease and that number is larger worldwide. Moreover, death rates due to lung diseases are currently increasing. According to the American Lung Association, chronic obstructive pulmonary disease (COPD) is expected to become the third leading cause of death by 2020.

A lung disease is any disease or disorder where lung function is impaired. Lung diseases can be caused by long-term and/or immediate exposure to, among other things, smoking, secondhand smoke, air pollution, occupational hazards such as asbestos and silica dust, carcinogens that trigger tumor growth, infectious agents, and over reactive immune defenses. Over a period of time, lung tissues including the airway and blood vessels become damaged such that there is not enough healthy tissue to support adequate gaseous exchange to supply sufficient oxygen for all the cells in the body for basic function. In essence, these people "suffocate" slowly to death. Therefore, lung disease can be a life-threatening illness or condition.

There are many types of lung diseases including: (A) Obstructive lung diseases such as asthma and COPD which includes chronic bronchitis and emphysema. These all affect a person's airways and limit or block the flow of air in or out of the lungs; (B) Infectious illnesses such as pneumonia, influenza, respiratory syncytial virus (RSV) and tuberculosis (TB). Bacteria or viruses cause these diseases that can also affect the membrane (or pleura) that surround the lungs; (C) Lung cancer which is a disease characterized by uncontrolled growth and spread of abnormal cells; (D) Respiratory failure, pulmonary edema, pulmonary embolism and pulmonary hypertension. These conditions are caused by problems with the normal gas exchange and blood flow in the lungs; and (E) Pulmonary fibrosis and sarcoidosis. These are diseases characterized by stiffening and scarring of the lungs and occupational diseases, such as mesothelioma and asbestosis, caused by expo-sure to hazardous substances.

Currently, all treatments for lung diseases are mainly palliative, where the emphasis is on maintaining quality of life through symptom management. Lung transplantation is the therapeutic measure of last resort for patients with end-stage lung disease who have exhausted all other available treatments without improvement. As of 2005, the most common reasons for lung transplantation in the United States were: 27% chronic obstructive pulmonary disease (COPD), including emphysema; 16% idiopathic pulmonary fibrosis; 14% cystic fibrosis; 12% idiopathic (formerly known as "primary") pulmonary hypertension; 5% alpha 1-antitrypsin deficiency; 2% replacing previously transplanted lungs that have since failed; and 24% other causes, including bronchiectasis and sarcoidosis.

Lung transplantation or pulmonary transplantation is a surgical procedure in which a patient's diseased lungs are partially or totally replaced by lungs which come from a donor. While lung transplants carry certain associated risks, they can also extend life expectancy and enhance the quality of life for end-stage pulmonary patients. Often, a combined heart and lung transplantation is done because both organs are intricately connected physically and functionally, and a dual transplant greatly increases the success of the transplant. However, the availability of a dual or even a single organ for transplant is very rare because certain criteria for potential donors must be fulfilled, e.g. health of donor, size match, the donated lung or lungs must be large enough to adequately oxygenate the patient, but small enough to fit within the recipient's chest cavity, age, and blood type. As a result, patients often die while on the waiting list.

Even for those lucky enough to receive a transplant, the average survival of a lung transplant patient is about 5 to 10 years which is relatively low compared to other type of organ transplantation; for lung transplant 53.4% and 28.4% respectively, and for heart-lung transplant 46.5% and 28.3% respectively (data taken from 2008 OPTN/SRTR Annual Report, US Scientific Registry of Transplant Recipients).

Sometimes, a lung transplant is not an option. Not all patients with lung disease make good candidates for lung transplant. Sometimes, despite the severity of a patient's respiratory condition, certain pre-existing conditions may make a person a poor candidate for lung transplantation. These conditions include: concurrent chronic illness (e.g. congestive heart failure, kidney disease, liver disease); current infections, including HIV and hepatitis, current or recent cancer; current use of alcohol, tobacco, or illegal drugs; age; within an acceptable weight range (marked undernourishment or obesity are both associated with increased mortality); psychiatric conditions; history of non-compliance with medical instructions; and previous multiple failed lung transplantation.

In addition for those patients having under gone a lung transplant, there may be other complications associated with the transplant which include organ rejection, post-transplant lymphoproliferative disorder, a form of lymphoma due to the immune suppressants, and gastrointestinal inflammation and ulceration of the stomach and esophagus.

Other solutions that supplement the palliative care that keep these patients alive are desirable, for example, for those on the waiting list, and especially those patients that do not qualify for lung transplant. Solutions that keep the patients off the lung transplant waiting list are also desired.

SUMMARY OF THE INVENTION

Embodiments of the invention relate to human stem cells and methods of preparing and using them.

Embodiments of the present invention are based on the discovery of a population of c-kit positive cells in the human adult lung tissues that have characteristics typical of a stem cell. Prior to the discovery, there has been no one cell type from lung tissues that have all the characteristics of a stem cell. The fundamental properties of stem cells are self-renewal, clonogenicity and multipotentiality in vitro and in vivo. The c-kit positive cells are generally of two major varieties: type 1—stem cell marker c-kit positive and the vascular endothelial growth factor receptor 2 negative (VEGF2), known also as KDR, and (b) type 2—expresses c-kit and KDR, i.e., c-kit and KDR positive.

These c-kit positive cells were able to replace and repair damaged lung tissues when transplanted into a mice. Based on these observations, embodiments of the present invention provide solutions to the problem of donor lung shortages and the problem of ineligibility for a lung transplant of a subject having a lung disease or is at risk of developing a lung disease in the future. Specifically, the problems are solved by implanting lung stem cells to defective and/or damaged lungs in order to promote lung repair and regeneration and to extend the life of the subject till a donor lung becomes available in the first case or for as long as possible with acceptable quality of life in the second case.

Accordingly, in one embodiment, the invention provides a population of isolated cells from a lung tissue sample, the population of isolated cells is substantially enriched for c-kit positive lung stem cells (LSCs). In one embodiment, this population of isolated cells that is substantially enriched for c-kit positive LSCs also comprises lung progenitor cells and lung precursor cells. In one embodiment, the population comprises c-kit and KDR positive LSCs and c-kit positive and KDR negative LSCs.

In one embodiment, provided herein is a composition for use in treating and/or preventing a lung disease in a subject, the composition comprising an enriched population of isolated c-kit positive LSCs from a lung tissue sample. In one embodiment, the composition comprises lung progenitor cells and lung precursor cells. In one embodiment, the composition further comprises a pharmaceutically acceptable carrier.

In one embodiment, provided herein is a composition for use in the manufacture of medicament for the treatment and/or prevention a lung disease in a subject, the composition comprising an enriched population of isolated c-kit positive LSCs from a lung tissue sample. In one embodiment, the enriched population of isolated c-kit positive LSCs also comprises lung progenitor cells and lung precursor cells.

In one embodiment, the invention provides a method of preparing a population of isolated cells substantially enriched for c-kit positive LSC, the method comprising obtaining a lung tissue sample from a subject; selecting c-kit positive cells from the lung tissue; and proliferating the selected c-kit cells in a culture medium to grow and increase the number of c-kit positive cells.

In another embodiment, the invention provides a method of proliferating or expanding a population of isolated cells substantially enriched for c-kit positive LSCs, the method comprising selecting at least one c-kit positive cell from a lung tissue sample; introducing the at least one selected cell to a culture medium; and proliferating the at least one selected cell in the culture medium, whereby the number of c-kit LSCs after proliferation is at least double the number of LSCs added to the culture medium initially, and preferably more than double. In some embodiments, the c-kit positive LSCs are proliferated or expanded in vitro for a period of 0.5 to 5 months.

In one embodiment, the invention provides a pharmaceutical composition comprising a population of isolated cells from a lung tissue sample; the population of isolated cells is substantially enriched for c-kit positive LSCs and is substantially negative for at least one marker of the hematopoietic lineage, mast cell lineage, mesenchymal stromal cell lineage, epithelial lineage and endothelial cell and smooth muscle cell lineage. In one embodiment, the population of isolated cells is substantially negative for all markers of hematopoietic lineage, mast cell lineage and mesenchymal stromal cell lineage described. In one embodiment, the composition further comprises a pharmaceutically acceptable carrier.

In one embodiment, the invention provides a method for treating or preventing a lung disease or disorder in a subject in need thereof, the method comprising obtaining a lung tissue sample from a subject; extracting a population of c-kit positive LSCs from the lung tissue; expanding the population of c-kit positive LSCs; and administering the population of c-kit positive LSCs to the subject for the c-kit LSCs to take up residence in the lungs and repairs/reconstitutes/and/or regenerates pulmonary cells and tissues in the lung of the subject.

In one embodiment, provided here is a method for treating or preventing a lung disease or disorder in a subject in need thereof, the method comprising administering a composition comprising a population of c-kit positive LSCs described herein to the subject.

In one embodiment of all aspects of the treatment method, the population of c-kit positive LSCs is derived from one subject and administered to another subject, meaning that the donor of the LSCs is not the same person as the recipient of the LSCs. It is understood that the donor and recipient should be antigen matched for such transplant, and the matching criteria and methods are well known in the art. The donor c-kit positive LSCs ideally should be allogenic and HLA type matched to a recipient.

Accordingly, in one embodiment, the invention provides a method for treating or preventing a lung disease or disorder in a subject in need thereof, the method comprising obtaining a lung tissue from a first subject; extracting a population of c-kit positive LSCs from the lung tissue sample; expanding the population of c-kit positive LSCs; and administering the population of c-kit positive LSCs to a second subject for the c-kit LSCs to take up residence in the lungs and repairs/reconstitutes/and/or regenerates pulmonary cells and tissues in the lung of the second subject. In one embodiment of this treatment method, the second subject is at least one HLA type matched with the first subject, the donor of the LSCs.

In one embodiment of all aspects of the treatment methods described, the administered population of isolated and substantially enriched c-kit positive LSCs repairs, reconstitutes or generates pulmonary epithelium, pulmonary vasculature/pulmonary endothelium and pulmonary alveoli in the lung of the subject.

In another embodiment of all aspects of the treatment methods described, the administered population of isolated and substantially enriched c-kit positive LSCs restores the structural and functional integrity of the lung of the subject.

In one embodiment of all aspects of the compositions and methods described, the lung tissue is from a human. In another embodiment of all aspects of the compositions and methods described, the human lung tissue is an adult lung tissue.

In one embodiment of all aspects of the compositions and methods described, the lung tissue sample is cryopreserved prior to the selection of c-kit positive cells. Cryopreservation can also be performed on the isolated c-kit positive LSCs from the lung tissue sample prior to the expansion in culture medium and on the expanded c-kit positive LSCs.

In one embodiment of all aspects of the compositions and methods described, the selection of c-kit positive cells is performed using an antibody against c-kit. In another embodiment of all aspects of the compositions and methods described, the selection of c-kit positive cells further comprises negative selection for at least one marker of the hematopoietic lineage, mast cell lineage, mesenchymal stromal cell lineage, epithelial lineage and/or endothelial cell and smooth muscle lineage cells.

Accordingly, in one embodiment of all aspects of the compositions and methods described, the population of isolated and substantially enriched c-kit positive LSCs is further substantially negative for at least one marker of the hematopoietic lineage, mast cell lineage, mesenchymal stromal cell lineage, epithelial lineage and/or smooth muscle and endothelial cell lineage. These c-kit positive cells are mainly negative for markers characteristic of the hematopoietic lineage, mast cell lineage, mesenchymal stromal cell lineage, epithelial lineage and/or endothelial cell lineage such as CD2, CD3, CD6, CD8, CD14, CD16, CD19, CD20, CD24, CD29, CD34, CD44, CD45, CD49d, CD49e, CD66b, CD90, CD105, CD133, glycophorin A, TTF1, p63, pan-cytokeratin, cytokeratin 5, CC10, aquaporin-5, SPC, Est1, vWF1, GATA 6, and alpha-SMA. It should not be construed that the lineage markers are limited to these markers only.

In one embodiment of all aspects of the compositions and methods described, the selection of c-kit positive cell is by flow cytometry.

In another embodiment of all aspects of the compositions and methods described, the selection of c-kit positive cell is by immunomagnetic selection with c-kit antibodies conjugated to beads.

In one embodiment of all aspects of the compositions and methods described herein, the method further comprises cyropreserving the population of isolated and substantially enriched c-kit positive LSC.

In one embodiment of all aspects of the treatment methods described, the therapeutic method further comprises administering at least one therapeutic agent, e.g., one that decreases pulmonary hypertension.

In one embodiment of all aspects of the treatment methods described, the therapeutic method further comprises selecting a subject who is suffering from a lung disorder prior to administering the population enriched for c-kit positive LSCs.

In one embodiment of all aspects of the treatment methods described, the therapeutic method further comprises selecting a subject in need of restoring the structural and functional integrity of a damaged lung prior to administering the cells.

In one embodiment of all aspects of the treatment methods described, the therapeutic method further comprises selecting a subject in need of treatment, prevention or repair or reconstitution or generation of pulmonary vasculature or pulmonary epithelium, pulmonary endothelium, or pulmonary alveoli prior to administering the cells. Subjects such as those who smoking and/or have been asbestos exposure are at high risk for developing various lung diseases and they would be candidate for the method to prevent their lung diseases from developing and also prevent the disease from progressing once the disease has started.

In one embodiment of all aspects of the therapeutic methods described herein, the administration is intrapulmonary administration, systemic administration, or a combination thereof.

In one embodiment of all aspects of the therapeutic methods described herein, the intrapulmonary administration is either intratracheal or intranasal administration.

DETAILED DESCRIPTION OF THE INVENTION

Figure 1A:
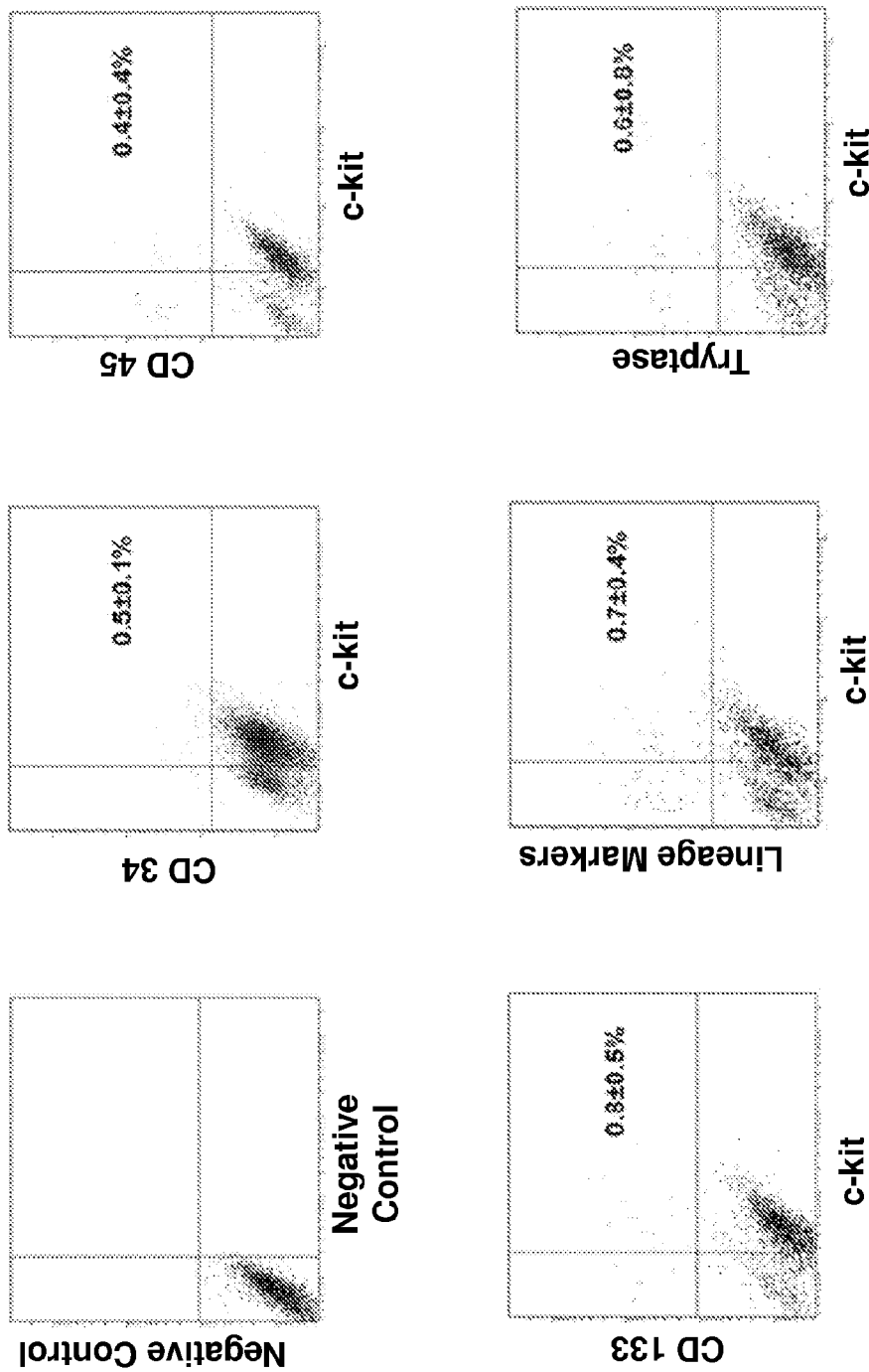
FIG. 1A show the bivariate distribution plots of c-kit-positive cells showing lack of expression of hematopoietic markers (CD34, CD45, CD133, cocktail of bone marrow cell lineages), tryptase and epitopes of mesenchymal stromal cells (CD44, CD90, CD105).
Figure 1A:
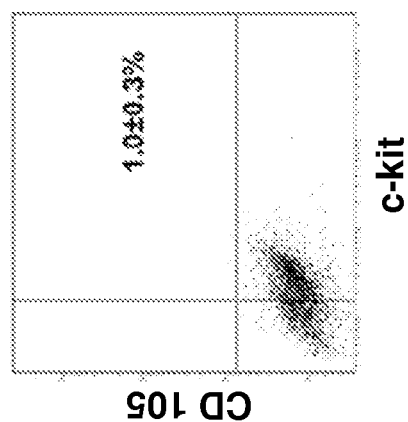
Figure 1A:
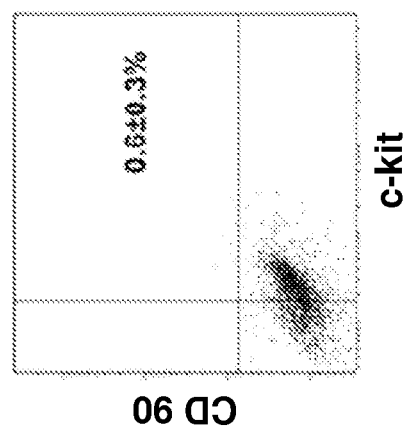
Figure 1A:
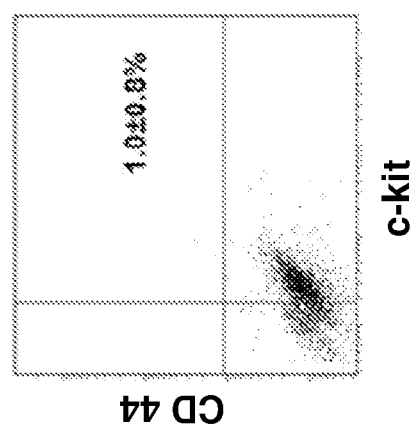
Figure 1B:
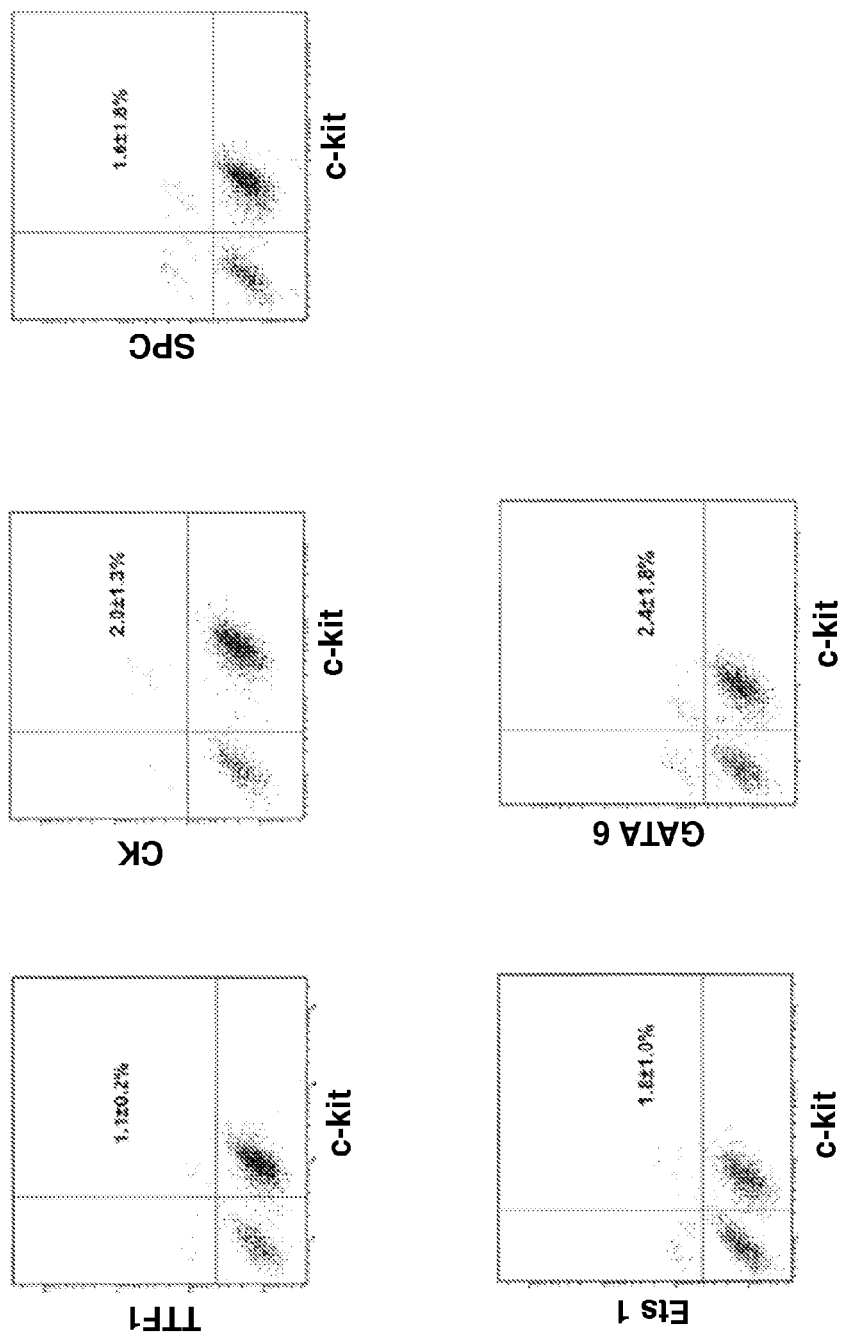
FIG. 1B show the bivariate distribution plots of c-kit-positive cells demonstrating that the cells are negative for antigens of lung cell classes.
Figure 1B:
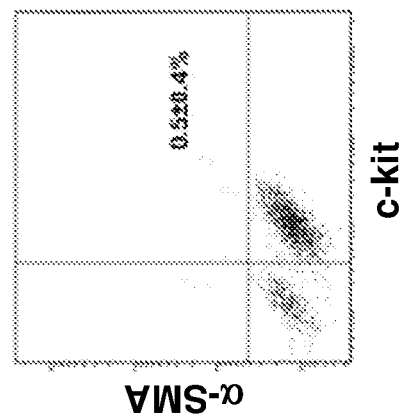
Figure 1B:
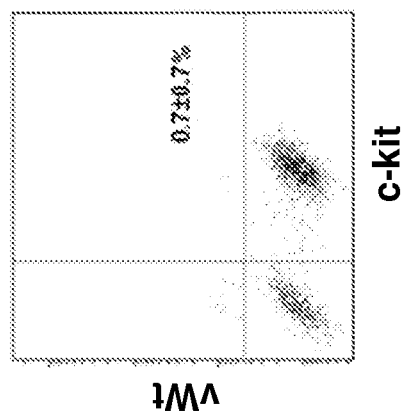

Embodiments of the present invention are based on the discovery of a population of c-kit positive cells in the human adult lung tissues that have characteristics typical of a stem cell and these human stem cells can repair and regenerate new lung tissues in a mouse lung. The fundamental properties of stem cells are the ability to self-renewal, i.e., make more of stem cells, clonogenicity and multipotentiality in vitro and in vivo. Prior to this discovery, there has been no one cell type from lung tissues that exhibit all three characteristics of a stem cell. The population of c-kit enriched cells is generally of two major varieties: type 1—stem cell marker c-kit positive and KDR (also known as Flk-1 VEGF-R2, Ly-73) negative, and type 2—c-kit positive and KDR positive.

As it is well known, stem cells, by virtue of its properties, give rise to all the cells and tissues of the body. Therefore, stem cells can be used to repair or speed up the repair of a damaged and/or defective lung. If sufficient amount of adult lung stem cells (LSCs) can be obtained, this amount of adult (LSCs) can be used to repair damaged and/or defective lungs by building new tissues in the lungs. In a defective and/or damaged lung, there may be few or absent LSCs. Since adult LSCs self-renew, the implanted adult LSCs will colonize and populate niches in the defective and/or damaged lung. By being clonal and multipotent, the implanted adult LSCs will also divide and differentiate to produce all new lung cells and tissues. Therefore, a population of isolated LSCs or a composition comprising a population of isolated LSCs can be used for treatment or prevention of a lung disease in a subject.

Accordingly, the problem of a subject with a lung disease dying prematurely before a donor lung becomes available or because of ineligibility for a lung transplant is solved by implanting LSCs to the defective and/or damaged lungs of the subject in order to promote de novo lung repair and regeneration. The de novo lung repair and regeneration can extend the life of the subject until a donor lung becomes available in the first case or sustain life of the subject for as long as possible with an acceptable quality of life in the second case.

Accordingly, in one embodiment, the invention provides a population of isolated cells from a sample of lung tissue, the population of isolated cells is substantially enriched for c-kit positive lung cells, which comprises predominately (≥99%) of LSCs.

In one embodiment, the population of isolated cells that is substantially enriched for c-kit positive cells also comprises a very small number of lung progenitor cells and lung precursor cells.

In one embodiment, provided herein is a composition for use in treating and/or preventing a lung disease in a subject, the composition comprising an enriched population of isolated c-kit positive LSCs from a lung tissue sample. In one embodiment of this composition, the composition comprises lung progenitor cells and lung precursor cells. In another embodiment of this composition, the composition further comprises a pharmaceutically acceptable carrier.

In one embodiment, provided herein is a composition for use in the manufacture of medicament for the treatment and/or prevention a lung disease in a subject, the composition comprising an enriched population of isolated c-kit positive LSCs from a lung tissue sample. In one embodiment of this composition, the enriched population of isolated c-kit positive LSCs also comprises lung progenitor cells and lung precursor cells. In another embodiment of this composition, the composition further comprises a pharmaceutically acceptable carrier.

In one embodiment, the invention provides a pharmaceutical composition comprising a population of isolated cells from a lung tissue sample and a pharmaceutical acceptable carrier; the population of isolated cells is substantially enriched for c-kit positive LSCs and is substantially negative for at least one marker of the hematopoietic lineage, mast cell lineage, mesenchymal stromal cell lineage, epithelial lineage, endothelial cell and smooth muscle cell lineage. Examples of these lineage markers are CD2, CD3, CD6, CD8, CD14, CD16, CD19, CD20, CD24, CD29, CD34, CD44, CD45, CD49d, CD49e, CD66b, CD90, CD105, CD133, glycophorin A, TTF1, p63, pan-cytokeratin, cytokeratin 5, CC10, aquaporin-5, SPC, Est1, vWF1, GATA 6, and alpha-SMA and these should no be construed as limiting to these only.

In one embodiment, the invention provides a method of preparing a population of isolated cells substantially enriched for c-kit positive LSCs, the method comprising obtaining a sample of lung tissue from a subject; selecting at least one c-kit positive cells from the sample of lung tissue; and proliferating the selected c-kit positive cells in a culture medium, whereby the number of c-kit positive cells increases by at least two fold over the initial amount selected, preferably by more than two folds.

In one embodiment, the invention provides a method of obtaining a population of isolated cells substantially enriched for c-kit positive LSCs, the method comprising cryopreserving a specimen of lung tissue obtained from a subject; thawing the cryopreserved specimen at a later date; selecting at least one c-kit positive cells from the specimen of lung tissue; and proliferating the selected c-kit positive cells in a culture medium whereby the number of c-kit positive cells at least doubles over the initial amount selected, preferably by more than double.

In one embodiment, the invention provides a method of proliferating a population of isolated cells substantially enriched for c-kit positive LSCs, the method comprising selecting at least one c-kit positive cell from a lung tissue sample; introducing the at least one c-kit positive selected cell to a culture medium; and proliferating the selected c-kit positive cell in the culture medium whereby the number of c-kit positive cells increase by at least two folds over the initial amount selected, preferably by more than two folds.

In another embodiment, the invention provides methods of use of this population of isolated cells that is substantially enriched for c-kit positive LSCs or use of a pharmaceutical composition comprising an enriched population of isolated c-kit positive LSCs. For example, for the repair, regenerate and/treatment of lung diseases and disorders. Without wishing to be bound by theory, the inventors considered the c-kit-positive-KDR-negative cells, termed pulmonary epithelial stem cells (PEPCs), were primarily responsible for the turnover and growth of pulmonary epithelial cells and the c-kit-positive-KDR-positive cells, termed pulmonary vascular progenitor cells (PVPCs), were primarily involved in the turnover and growth of pulmonary vessels. Hence, in one embodiment, a population of isolated c-kit positive LSCs which have been expanded in vitro, being a mixture of PEPCs and PVPCs, can be transplanted or implanted into an affected/damaged lung. The c-kit positive LSCs then take up residence in the lung, grow and differentiate into the various types of tissues normally found in a lung, for restoring and reconstituting the pulmonary epithelial and pulmonary vessels etc in a damage lung, e.g., epithelial, vascular, alveolar, secretory cells etc. The goal is to replace some of the damaged lung tissue due to disease in the affected lung. The replacement lung tissue serve to supplement existing or remaining lung tissue in the affected subject so that over all there is enough tissue for adequate gaseous change to sustaining life in that subject.

In a proof-of-principle experiment, the inventors injected some human c-kit positive LSCs into the damaged site of a mouse lung. The inventors showed that the human LCSs created human bronchioles, alveoli and pulmonary vessels integrated structurally with the recipient mouse organ (data not shown). Multiple injections of hLSCs were performed at the site of injury. The pulmonary repair process mediated by hLSC differentiation occurred independently of fusion events. The formation of a chimeric organ was confirmed by detection of human transcripts for epithelial and vascular genes. The epithelial differentiation of hLSCs was documented further by fate mapping in which the reporter gene was shared by clonogenic hLSCs and the derived type II alveolar epithelial cells. These observations provide strong evidence in favor of the crucial role that hLSCs can have in tissue homeostasis and regeneration following injury.

Adult stem cell transplantation has emerged as a new alternative to stimulate repair of injured tissues and organs. In the past decade, some studies in animals and humans have documented the ability of adult bone marrow-derived stem cells, i.e., hematopoietic stem cells, to differentiate into an expanding repertoire of non-hematopoietic cell types, including brain, skeletal muscle, chondrocytes, liver, endothelium, and heart. However, the lung and associated respiratory structures have remained relatively resistant to such therapeutic modalities. There are, however, reports indicating that mesenchymal stem cells can be used for stem cell therapies in the lung, and that hematopoietic stem cells can be co-administered with mesenchymal stem cells in pulmonary transplantation. For example, it has been described that co-transplantation of mesenchymal cells, isolated as non-hematopoietic cells from fetal lung CD34+ cells, enhanced the engraftment of hematopoietic stem cells (Noort et al., Exp Hematol 2002; 30:870-78).

Several other reports also describe the use of mesenchymal stem cells and non-hematopoietic stem cells derived from bone-marrow populations in lung therapies in animal models (Krause D S et al., Cell 2001, 105:369-377; Kotton D N, et al., Development 2001, 128:5181-5188; Ortiz L A, et al., Proc Natl Acad Sci USA 2003, 100:8407-8411; Theise N D et al., Exp Hematol 2002, 30:1333-1338; Abe S et al., Cytotherapy 2003, 5:523-533; Aliotta J M et al., Exp Hematol 2006, 34:230-241; Rojas M et al., Am J Respir Cell Mol Biol 2005, 33:145-152; Gupta N et al., J Immunol 2007; 179:1855-1863; US Patent Application 20090274665).

While evidence exists supporting the ability of some types of bone marrow-derived stem cells, i.e., mesenchymal stem cells, to give rise to lung tissue, other reports have been unable to detect significant regeneration of lung tissue with bone marrow cells (Kotton D N et al., Am J Respir Cell Mol Biol 2005; 33:328-334; Wagers A J, et al., Science 2002, 297:2256-2259; Chang J C, et al. Am J Respir Cell Mol Biol 2005, 33:335-342). In addition, other reports have described that hematopoietic stem cells derived from bone marrow administered via an intranasal route results in alveolar macrophages, and that this population does not transdifferentiate into respiratory epithelial cells (Fritzell J A et al., Am J Respir Cell Mol Biol 2009, 40:575-587).

However, there is no literature that demonstrates the presence of legitimate stem cells in the lung and the use of these LSCs for lung therapy. The advantage of the present invention is that the LSCs used of lung therapy can be autologous cells which will greatly increase success rate of the therapy. A portion of a patient's lung is removed surgically, e.g., during a biopsy. As little as one cubic centimeter is sufficient. The piece of tissue is treated to release single cells from the connective tissue. Using the stem cell marker, c-kit, as an indication of stem cells, c-kit positive cells are selected. Optionally, these c-kit positive LSCs can be further negatively selected for at least one marker of the hematopoietic lineage, mast cell lineage, mesenchymal stromal cell lineage, epithelial lineage, endothelial cell and smooth muscle cell lineage. The c-kit positive LSCs are then expanded in vitro to obtain sufficient number of cells required for the therapy. When there are enough cells, the cells are harvested and injected back into the same patient or a genetically matched patient with respect to the donor of the LSCs. At each transitional step, e.g., bet between selection and expansion ween selection and expansion or between expansion and implanting, the LSCs can be optionally cryopreserved. In one embodiment, the patient gets back the patient's own LSCs that have been selected and expanded in vitro. In another embodiment, the patient gets the LSCs derived from a genetically matched donor. In some embodiments, this method can also be extended to any mammal that has lungs, e.g., cat, dog, horse, monkey etc.

Accordingly, the invention provides a method for the treatment and/or prevention of a lung disease or disorder in a subject in need thereof comprising administering a therapeutically effective amount of a population of isolated and substantially enriched c-kit positive LSCs to the subject.

In one embodiment, provided here is a method for treating and/or preventing a lung disease or disorder in a subject in need thereof, the method comprising administering a composition comprising a population of c-kit positive LSCs described herein to the subject.

In another embodiment, the invention provides a method for treating and/or preventing a lung disease in a subject in need thereof, comprising obtaining a sample of lung tissue from a subject; extracting a population of c-kit positive LSCs from the lung tissue sample; expanding the selected c-kit positive LSCs in vitro to increase the numbers of such LSCs; and administering the expanded population of c-kit positive LSCs to the subject for the LSCs repair, reconstitute or regenerate pulmonary epithelium, pulmonary vasculature/pulmonary endothelium and/or or pulmonary alveoli in the lungs of the subject.

In another embodiment, the invention provides a method for treating or preventing a lung disease or disorder in a subject in need thereof, the method comprising obtaining a lung tissue from a first subject; extracting a population of c-kit positive LSCs from the lung tissue sample; expanding the population of c-kit positive LSCs; and administering the population of c-kit positive LSCs to a second subject for the c-kit LSCs to take up residence in the lungs and repairs/reconstitutes/and/or regenerates pulmonary cells and tissues in the lung of the second subject. In one embodiment of this treatment method, the second subject is at least one HLA type matched with the first subject, the donor of the LSCs.

In one embodiment of all aspects of the compositions and methods described, the c-kit positive LSCs that make up predominately the population of isolated cells have self-renewal capability, clonogenicity and multipotentiality. This means that single isolated c-kit positive cell can divide to give rise to more c-kit positive cells, forming a colony in culture. When stimulated under certain conditions, the c-kit positive cell can became determinate (i.e., selection a specific cell lineage to differentiate into) and further differentiate to cells of a specific lineage, e.g., the hematopoietic lineage, mast cell lineage, mesenchymal stromal cell lineage, epithelial lineage, endothelial cell and smooth muscle cell lineage. These cells and its progeny, upon determination and differentiation, will express the particular cell markers characteristic of the determined lineage. In addition, the determinate cell and its progeny will loss the expression of c-kit.

In one embodiment of all aspects of the compositions and methods described, the lung tissue is from a human. In another embodiment of all aspects of the compositions and methods described, the human is an adult.

In some embodiments of all aspects of the compositions and methods described, the c-kit positive LSCs comprise two sub-population of cells, one that expresses KDR (i.e., KDR positive) and one that do not express KDR (i.e., KDR negative). In some embodiments of all aspects of the compositions and methods described, the population of isolated cells substantially enriched for c-kit positive LSCs comprises c-kit positive/KDR negative cells and c-kit positive/KDR positive cells.

In one embodiment of all aspects of the described methods, the lung tissue is cryopreserved prior to selecting c-kit positive cells.

In one embodiment of all aspects of the described methods, the selection of the c-kit positive LSCs is performed using an antibody against c-kit.

In one embodiment of all aspects of the described methods, the antibody against c-kit is a monoclonal antibody.

In one embodiment of all aspects of the described methods, the monoclonal antibody against c-kit is a mouse monoclonal IgG against an antigenic epitope of human c-kit.

In one embodiment of the any of the described methods, the antibody against c-kit is fluorochrome conjugated.

In one embodiment of all aspects of the described methods, the antibody against c-kit is conjugated to magnetic particles.

In one embodiment of all aspects of the described methods, the method further comprises negative selection for at least one marker of the hematopoietic lineage, mast cell lineage, mesenchymal stromal cell lineage, and epithelial lineage endothelial cell and/or smooth muscle cell lineage cells.

In one embodiment of all aspects of the described methods, the selection of c-kit positive cells and/or the selection of various lineage marker negative cells by flow cytometry.

In one embodiment of all aspects of the described methods, the selection is by fluorescence activated cell sorting or high gradient magnetic selection.

In one embodiment of all aspects of the described methods, the at least one marker of a hematopoietic lineage is selected from the group consisting of CD34, CD45, and CD133.

In one embodiment of all aspects of the described methods, the at least one marker of a mast cell lineage is selected from the group consisting of CD6, CD29, CD49d, CD49e, CD45 and tryptase.

In one embodiment of all aspects of the described methods, the at least one marker of a mesenchymal stromal cell lineage is selected from the group consisting of CD44, CD90 and CD105.

In one embodiment of all aspects of the described methods, the at least one marker of an epithelial cell lineage is selected from the group consisting of TTF1, p63, pan-cytokeratin, cytokeratin 5, CC10, aquaporin-5 and SPC.

In one embodiment of all aspects of the described methods, the at least one marker of an endothelial cell and smooth muscle cell lineage is selected from the group consisting of Est1, vWF1, GATA 6, and alpha-SMA.

In one embodiment of all aspects of the described methods, the c-kit positive LSCs are further negative for CD2, CD3, CD8, CD14, CD16, CD19, CD20, CD24, CD66b, and glycophorin A.

In one embodiment of all aspects of the described methods, the c-kit positive LSCs are further expanded ex vivo. In one embodiment of all aspects of the described methods, the c-kit positive LSCs are further expanded in vitro. The goal is to have a sufficiently large amount of c-kit positive LSCs for implanting to ensure successful engrafting of the implanted LSCs into niches of the damaged lungs. Basically, there must be sufficient cells to grow and multiply in the damaged lung to provide all the cells needed to repair and/or replace the damage parts of the lungs.

In one embodiment of all aspects of the described methods, the c-kit positive LSCs are at least double in number after the expansion or proliferation step. In some embodiments of all aspects of the described methods, it is desirable that the number of c-kit positive cells, upon expansion or proliferation, is increased by at least 5 fold, 10 fold, 20 fold, 50 fold, 100 fold, 200 fold, 500 fold, 1000 fold, 2000 fold, 5000 fold, 10,000 fold, 20,000 fold, 50,000 fold or more at the end of the proliferation phase. The number of cells in a culture can be determined by any methods known in the art, e.g., by using a coulter counter. These methods are well known to those skilled in the art.

In one embodiment of all aspects of the described methods, the selected c-kit positive LSCs are cryopreserved for storage prior expansion.

In another embodiment of all aspects of the described methods, the expanded LSCs are cryopreserved for storage purposes. When needed, the frozen cells are thawed and then used for implant into a subject in need thereof.

In one embodiment of all aspects of the described methods, the method further comprises cyropreserving the population of isolated c-kit positive LSCs.

For a person who has been newly diagnosed with a lung disease, if a biopsy sample of his lung was obtained for the diagnosis, a population of c-kit positive LSCs can be prepared according to the methods described here and the LSCs can then be cyropreserved for future use in the event that the disease had progressed to an advance stage such that the person needed a lung transplant.

Similarly, people who are at risk of developing lung diseases can benefit from early preparation of a population of c-kit LSCs form their own lung tissue and cyropreserving the LSCs. For example, a heavy smoker and a person having prior exposure the asbestos. This is in because it can take anywhere from 10 to 40 years or more for symptoms of a smoking related or an asbestos-related condition to appear. Other type of people at risk of developing lung diseases or damage include but are not limited to a baby carrying a cystic fibrosis gene or is diagnosed with cystic fibrosis and an active military personnel deployed to a war zone.

In some embodiments of all aspects of the therapeutic methods, treating and treatment includes "restoring structural and functional integrity" to a damaged lung in a subject in need thereof.

In other embodiments of all aspects of the described methods, treating includes repairing damaged or inadequate human lung. In another embodiment, treating and treatment includes repair, reconstitution or regeneration of pulmonary epithelium, pulmonary vasculature/pulmonary endothelium and/or or pulmonary alveoli in a damaged lung.

The restoring or repairing need not be to 100% to that of the lung of a healthy person. As long as there is an improvement in the symptoms in the subject, restoring or repairing has been achieved. A skilled physician would be able to assess the severity of the symptoms before and after the treatment and based on a comparison determine whether there is an improvement. Often, the subject will be able to say whether there is an improvement in the symptoms. Examples of some symptoms include but are limited to shortness of breath, wheezing, or hoarseness, persistent cough, pain or tightening in the chest and the presence of fluid in the lungs.

In one embodiment of all aspects of the therapeutic methods, preventing and prevention includes slowing down the reduced functioning capacity and integrity of the lung due to disease, e.g., from cystic fibrosis and autoimmune diseases.

In one embodiment of all aspects of the therapeutic methods, the population of c-kit positive LSCs repairs, reconstitutes or generates pulmonary epithelium, pulmonary vasculature/pulmonary endothelium and/or or pulmonary alveoli.

In one embodiment of all aspects of the compositions and methods described, the population of isolated c-kit positive LSCs is further substantially negative for at least one marker of the hematopoietic lineage, mast cell lineage, mesenchymal stromal cell lineage, epithelial lineage and/or endothelial cell and smooth muscle cell lineage, e.g. CD2, CD3, CD6, CD8, CD14, CD16, CD19, CD20, CD24, CD29, CD34, CD44, CD45, CD49d, CD49e, CD66b, CD90, CD105, CD133, glycophorin A, TTF1, p63, pan-cytokeratin, cytokeratin 5, CC10, aquaporin-5, SPC, Est1, vWF1, GATA 6, and alpha-SMA.

In one embodiment of all aspects of the therapeutic methods, the method of treating and/or preventing a lung disease further comprises administering at least one therapeutic agent. Such therapeutic agent ideally would be those used for the treatment of the lung disease and these are generally known to skilled physicians, e.g., therapy for pulmonary hypertension or COPD.

In one embodiment of all aspects of the therapeutic methods, the method of treating and/or preventing a lung disease further comprises selecting a subject who is suffering from a lung disorder prior to administering the population of cells that is substantially enriched for c-kit positive LSCs, e.g., a subject suffering from COPD or mesothelioma.

In one embodiment of all aspects of the therapeutic methods, the method of treating and/or preventing a lung disease further comprises selecting a subject in need of restoring the structural and functional integrity of a damaged lung prior to administering the cells, e.g. a subject suffering from sarcoidosis.

In one embodiment of all aspects of the therapeutic methods, the method of treating and/or preventing a lung disease further comprises selecting a subject in need of treatment, prevention or repair or reconstitution or generation of pulmonary vasculature or pulmonary epithelium, pulmonary endothelium, or pulmonary alveoli prior to administering the cells, e.g., a subject suffering from pulmonary fibrosis.

For example, the selected subjects are those who have not responded at all or well to the traditional treatment and/or one who has exhausted all therapeutic option currently known in the art for a particular form or type of lung disease. Other examples of subjects to be selected would be those who are deemed not suitable subjects for any lung transplantation or have been on the transplant waiting list for a long time without sight of a suitable donor (also there is no live donor) and is on the critical list.

In one embodiment of all aspects of the therapeutic methods for treating or preventing a lung disease, the administration is intrapulmonary administration, systemic administration, or a combination thereof.

In one embodiment of all aspects of the therapeutic methods for treating or preventing a lung disease, the intrapulmonary administration is intratracheal or intranasal administration.

In one embodiment of all aspects of the therapeutic methods for treating or preventing a lung disease, the subject is an intubated subject.

In one embodiment of all aspects of the therapeutic methods for treating or preventing a lung disease, the c-kit positive LSCs are autologous cells.

In one embodiment of all aspects of the therapeutic methods for treating or preventing a lung disease, the c-kit positive LSCs are allogeneic cells obtained from one or more donors.

In one embodiment of all aspects of the therapeutic methods, the c-kit positive LSCs are human leukocyte antigen (HLA) typed matched for the recipient subject of the cells. In one embodiment, c-kit positive LSCs are isolated and expanded from a single donor and the progenitor cells are matched for at least 4 out of 6 alleles of the HLA class I: HLA-A and HLA-B; and HLA class II: DRB1 with the recipient. In another embodiment, c-kit positive LSCs are isolated and expanded from different donors and the progenitor cells are HLA type matched for at least 4 out of 6 alleles of the HLA class I: HLA-A and HLA-B; and HLA class II: DRB1 with the recipient subject. Methods for HLA typing are known in the art, e.g., in Bodmer, W., 1973, in Manual of Tissue Typing Techniques, Ray, J. G., et al., eds., DHEW Publication No. (NIH) 74-545, pp. 24-27 which is incorporated herein by reference in its entirety.

In one embodiment of all aspects of the therapeutic methods, the method further comprises with at least one therapeutic agent with the c-kit positive LSCs, e.g., those for treating cystic fibrosis, COPD, pulmonary fibrosis and sarcoidosis.

In one embodiment of all aspects of the therapeutic methods, the at least one therapeutic agent enhances homing, engraftment, or survival of the population of LSCs.

In one embodiment of all aspects of the therapeutic methods, the subject is a mammal, preferably a human. In another embodiment, the subject is an adult human. In one embodiment, the population of c-kit positive LSCs is a population of c-kit positive human LSCs.

Lung Stem Cells (LSCs)

Stem cells are cells that retain the ability to renew their own kind through mitotic cell division and their daughter cells can differentiate into a diverse range of specialized cell types. The two broad types of mammalian stem cells are: embryonic stem (ES) cells that are found in blastocysts, and adult stem cells that are found in adult tissues. In a developing embryo, ESs can differentiate into all of the specialized embryonic tissues. In adult organisms, adult stem cells and progenitor cells act as a repair system for the body, replenishing specialized cells, but also maintain the normal turnover of regenerative organs, such as blood, skin or intestinal tissues. Pluripotent stem cells can differentiate into cells derived from any of the three germ layers.

In some embodiment, the term "stem cell" as used herein, refers to an undifferentiated cell which is capable of proliferation and giving rise to more progenitor cells having the ability to generate a large number of mother cells that can in turn give rise to differentiated, or differentiable daughter cells known as precursor cells. The daughter cells themselves can be induced to proliferate and produce progeny that subsequently differentiate into one or more mature cell types, while also retaining one or more cells with parental developmental potential.

In some embodiment, the term "stem cell" also refers to a subset of progenitors that have the capacity or potential, under particular circumstances, to differentiate to a more specialized or differentiated phenotype, and also retains the capacity, under certain circumstances, to proliferate without substantially differentiating.

The LSCs described herein are somatic stem cells as oppose to ESs. In a preferred embodiment, the LSCs described are adult stem cells.

In one embodiment, as used herein, the term "c-kit positive lung stem cell" or "c-kit positive LSC" encompass stem cells, progenitor cells and precursor cells, all of which are c-kit positive.

In one embodiment, as used herein, the term "c-kit positive lung stem cell" or "c-kit positive LSC" encompasses c-kit positive/KDR positive cells and c-kit positive/KDR negative cells.

Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are "multipotent" because they can produce progeny of more than one distinct cell type, and is a required as used in this document. Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stem cells, thus maintaining some stem cells in the population as a whole, while other cells in the population give rise to differentiated progeny only.

In one embodiment, the population of isolated cells that is substantially enriched for c-kit positive cells comprises predominantly LSCs (≥99%) and a very small amount of lung progenitor cells and lung precursor cells (≤1%). Therefore, in one embodiment, the population of isolated cells that is substantially enriched for c-kit positive cells is referred to as a population of isolated c-kit positive LSC. It is meant that the population of c-kit positive LSCs can include some c-kit positive progenitor cells and/or c-kit precursor cells.

As used herein, in some embodiments, the term "a population of isolated and substantially enriched for c-kit positive LSCs" or "a population of isolated c-kit positive LSCs" encompasses a heterogeneous or homogeneous population of LSCs and/or lung progenitor cells and/or lung precursor cells. LSCs are multipotent and produced cell types of many lineages. In contrast, lung progenitor cells and lung precursor cells are lineage determinate cells. For example, if a lung progenitor cell is determinate for an epithelial lineage, i.e., will produce pulmonary epithelial cells in the future, this lung progenitor cell will not switch and produce blood cells, which are cells of the hematopoietic lineage. In some embodiments, lung progenitor cells and lung precursor cells are determinate for a pulmonary epithelial lineage, a pulmonary endothelial lineage or a pulmonary alveoli cell lineage. A population of isolated c-kit positive LSCs comprises at least two different cell types is referred to herein as a "heterogeneous population". It is also contemplated herein that lung stem cells or lung progenitor cells are isolated and expanded ex vivo prior to transplantation. A population of isolated c-kit positive LSCs comprising only one cell type (e.g., lung stem cells) is referred to herein as a "homogeneous population of cells".

In the example, this population of cells in the human adult lung tissues expresses the c-kit, also called KIT or CD117, which is a cytokine receptor that binds cytokine stem cell factor (SCF). SCF signals to cells to divide and grow. In general, c-kit is expressed on the surface of stem cells as well as the progenitor and precursor cell types which are progeny from the stem cells by mitotic division. Therefore, c-kit is a stem cell marker. By immunostaining for c-kit in human adult lung tissues, the inventors found such c-kit positive cells (data not shown). Prior to this discovery, there has been no reported evidence of the presence of stem cells in the lungs. These c-kit positive cells are mainly undifferentiated, and are nested in niches located in proximity of distal airways. These c-kit positive cells are mainly negative for markers characteristic of the hematopoietic lineage, mast cell lineage, mesenchymal stromal cell lineage, epithelial lineage and/or endothelial cell lineage such as CD2, CD3, CD6, CD8, CD14, CD16, CD19, CD20, CD24, CD29, CD34, CD44, CD45, CD49d, CD49e, CD66b, CD90, CD105, CD133, glycophorin A, TTF1, p63, pan-cytokeratin, cytokeratin 5, CC10, aquaporin-5, SPC, Est1, vWF1, GATA 6, and alpha-SMA (FIG. 1A-1D). The c-kit positive progenitor and c-kit positive precursor cell types that are progeny of these c-kit positive LSCs however also expressed a small amount of the thyroid transcription factor-1 (TTF1) in the absence of specialized cytoplasmic proteins (for the progenitor cells) and TTF1 and surfactant protein C(SPC) or cytokeratin (for the precursor cells, see FIG. 2).

The inventors showed that these c-kit positive LSCs have clonogenic properties. When these cells were isolated and plated at very low cell density, i.e., plated single cell in vitro, multicellular clones grew out of these single cells (data not shown) after 3-4 weeks, thus demonstrating the clonogenic properties of stem cells.

Moreover, the multicellular clones arising from the initially isolated c-kit positive LSCs are multipotent in term of the cell fate of the daughter cells of the colonies. The inventors showed that the multicellular clones can differentiate into the epithelial and vascular lineages as indicated by the expressions of the specific markers of epithelial (TTF1, cytokeratin, and SPC) (data not shown) and vascular (Est1, vWF1, GATA 6, and alpha-SMA) (FIGS. 1C and 1D) lineages.

Finally, these c-kit positive LSCs can self renew. The inventors showed that the c-kit positive LSCs divide asymmetrically to give one daughter cell which expresses TTF1, GATA 6 or Est1 (this being the lung progenitor cell, see FIG. 2) while the other daughter cell retains stem cell characteristics and becomes the stem cell (data not shown).

In one embodiment of all aspects of the compositions and methods described, the population of isolated cells that is substantially enriched for c-kit positive LSCs are substantially negative for markers characteristic of the hematopoietic lineage, mast cell lineage, mesenchymal stromal cell lineage, epithelial lineage and/or endothelial cell lineage such as CD2, CD3, CD6, CD8, CD14, CD16, CD19, CD20, CD24, CD29, CD34, CD44, CD45, CD49d, CD49e, CD66b, CD90, CD105, CD133, glycophorin A, TTF1, p63, pan-cytokeratin, cytokeratin 5, CC10, aquaporin-5, SPC, Est1, vWF1, GATA 6, and alpha-SMA.

In one embodiment of all aspects of the compositions and methods described, the population of isolated c-kit positive LSCs contains cells that have long-term and short-term regeneration capacities, and committed multipotent, oligopotent, and unipotent progenitors.

Accordingly, as used herein, the term "LSC" refers to a cell with multi-lineage pulmonary differentiation potential and sustained self-renewal activity. "Self renewal" refers to the ability of a cell to divide and generate at least one daughter cell with the identical (e.g., self-renewing) characteristics of the parent cell. The second daughter cell may commit to a particular differentiation pathway. For example, a self-renewing LSC divides and forms one daughter stem cell and another daughter cell committed to differentiation in the pulmonary epithelial or pulmonary vessel pathway. A committed progenitor cell has typically lost the self-renewal capacity, and upon cell division produces two daughter cells that display a more differentiated (i.e., restricted) phenotype.

"LCSs," as used in the methods described herein, therefore, encompasses all pluripotent cells capable of differentiating into several cell types of the respiratory system, including, but not limited to, pneumocyte type I and type II cells, interalveolar cells, smooth muscle cells, alveoli epithelial cells, endothelial cells and erythrocytes.

"Lung progenitor cells," as the term is used herein, refer to the subset of LSC that are committed to a particular pulmonary cell lineage and generally do not self-renew, and can be identified, for example by cell surface markers or intracellular proteins. For example, TTF1 which indicates commitment to the pulmonary epithelial lineage; or GATA6 and/or Est1 which indicates commitment to the pulmonary vessel lineage (see FIG. 2). In some embodiments of all aspects of the compositions and methods described, LSCs are selected for using one or more of these additional cell surface markers.

The presence of LSC can be determined by any method known in the art, or phenotypically through the detection of cell surface markers using assays known to those of skill in the art or those described in the example.

Isolation of LSCs

In some embodiments of all aspects of the compositions and methods described, the LSC are derived or isolated from lung tissue samples of the following sources: aborted fetus, fetal biopsy tissue, freshly deceased subjects, tissue biopsy from a live subject, a lung stem cell line. In some embodiments of all aspects of the compositions and methods described, the LSCs are derived ex vivo from other cells, such as embryonic stem cells, induced pluripotent stem cells (iPS cells) or adult pluripotent cells.

In one embodiment of all aspects of the compositions and methods described, the LSC can be isolated using any method known to one of skill in the art or according to the method described herein. For example, fine needle aspiration for a small lung tissue sample from a live subject.

LSC can be isolated for lung tissue samples by any method known in the art, e.g., by the method described in the Example section. Methods of dissociating individual cells from a tissue sample are known in the art, e.g., in U.S. Pat. No. 7,547,674 and U.S. Patent Application U.S. 2006/0239983, 2009/0148421, and 2009/0180998. These references are herein incorporated by reference in their entirety.

In one embodiment of all aspects of the compositions and methods described, the population of isolated LSCs is isolated by the following method. One skilled in the art would be able to make minor adjustment to the method as needed for lung tissues from different sources. A small piece of lung tissue, a minimum size of at least 1 cubic cm, is enzymatically digested with collagenase to obtain single cells (Kajstura, J., et al., 1995, Circulation 92:2306-2317; Leri, A., et al., 2001, Proc. Natl. Acad. Sci. USA 98:8626-8631). Small intact cells are resuspended and aggregates of cells are removed with a cell strainer. This cell strainer step is optional. Then the cells are incubated with a mouse c-kit antibody. Single cells c-kit positive cells are isolated and collected with immunomagnetic beads coated with anti-mouse IgG.

In one embodiment of all aspects of the compositions and methods described, the isolated c-kit positive cells obtained are then cultured by the following method. One skilled in the art would be able to make minor adjustment to the method as needed. The culture method is used to grow and expand the number of c-kit positive LSCs. The isolated c-kit positive cells are plated in modified F12K medium containing F12 medium (GIBCO, Grand Island, N.Y.) supplemented with 5-10% FBS (GIBCO) and insulin-selenium-transferrin mixture (SIGMA, St. Louis, Mo.) under standard tissue culture conditions. After reaching confluence, the cells are passaged to several other plates to expand the culture using standard tissue culture protocol of handling the cells.

In some embodiments of all aspects of the compositions and methods described, the LSC from the lung tissues described herein is expanded ex vivo using any method acceptable to those skilled in the art prior to use in the methods described herein. In some embodiments of all aspects of the compositions and methods described, the expanded c-kit positive LSCs are further sorted, fractionated, treated to remove any undesired cells, or otherwise manipulated to treat the patient using any procedure acceptable to those skilled in the art of preparing cells for transplantation. Example of an undesired cell is a malignant cell.

There is typically a very small number of LSCs in a sample of lung tissue, for example, there can be only one or two c-kit positive cell per one million cells. Therefore, expansion of the selected c-kit positive LSCs is necessary to increase the number of cells required for the therapeutic uses described herein. The greater number of LSCs transplanted in the therapeutic uses described herein increases the success rate of the therapy used therein. The LSCs are used to repair, reconstitute and generate some of the damaged tissues and cells in the subject's lung. Therefore, more LSCs transplanted means more cells available to repair, reconstitute and generate new lung cells and lung tissue. In some embodiments, a success of the transplant therapy can be measured by any method known in the art and those described herein, such as an improvement in the subject's lung function, blood oxygen saturation and general health conditions which are known to a physician skilled in the art.

In some embodiments of all aspects of the compositions and methods described, a lung tissue sample comprising LSC is isolated from a subject and is then further processed, for example, by cell sorting (e.g., FACS), to obtain a population of substantially enriched c-kit positive LSCs. In other embodiments of all aspects of the compositions and methods described, a population of substantially enriched c-kit positive LSCs refers to an in vitro or ex vivo culture of expanded LSCs.

In some embodiments of all aspects of the compositions and methods described, the lung tissue samples from the various sources are frozen samples, such as frozen or cryopreserved prior to extraction or selection of the c-kit positive LSCs. The lung tissue sample is obtained from a subject or other sources described herein and then cryopreserved with cryoprotectant. In another embodiment of all aspects of the compositions and methods described, the population of isolated c-kit LSCs from the lung tissue sample is cryopreserved with cryoprotectant prior to use. In yet another embodiment of all aspects of the compositions and methods described, the population of isolated c-kit LSCs that has been expanded in vitro culture is cryopreserved with cryoprotectant prior to use. Methods of cryopreservation of tissues and cells with cryoprotectant are well known in the art. Further methods for thawing the cryopreserved tissue or cells for use are also well known in the art.

The terms "isolate" and "methods of obtaining or preparing," as used herein, refer to a process whereby a cell or a population of cells, such as a population of LSCs, is removed from a subject or a lung tissue sample in which it was originally found. The term "isolated population," as used herein, refers to a population of cells that has been removed and separated from a biological sample, or a mixed or heterogeneous population of cells found in such a sample. Such a mixed population includes, for example, a population of LSCs obtained from a lung tissue sample. In some embodiments, an isolated population is a substantially pure population of cells as compared to the heterogeneous population from which the cells were isolated or enriched from.

In some embodiments, the isolated population is a population of isolated c-kit positive LSCs. In other embodiments of this aspect and all aspects described herein, the isolated population comprises a substantially enriched population of c-kit positive LSCs. In some embodiments, an isolated cell or cell population, such as a population of c-kit positive LSCs, is further cultured in vitro or ex vivo, e.g., in the presence of growth factors or cytokines, to further expand the number of cells in the isolated cell population or substantially c-kit enriched cell population. Such culture can be performed using any method known to one of skill in the art, for example, as described in the Examples section. In some embodiments, the isolated or substantially enriched c-kit positive LSCs populations obtained by the methods disclosed herein are later administered to a second subject, or re-introduced into the subject from which the cell population was originally isolated (e.g., allogenic transplantation vs. autologous administration).

The term "substantially enriched," with respect to a particular cell population, refers to a population of cells that is at least about 75%, at least about 80%, at least about 85%, at least about 90%, at least about 95%, at least about 98%, or at least about 99% pure, with respect to the cells making up a total cell population. In other words, the terms "substantially enriched" or "essentially purified", with regard to a population of c-kit positive LSCs isolated for use in the methods disclosed herein, refers to a population of c-kit positive LSCs that contain fewer than about 25%, fewer than about 20%, fewer than about 15%, fewer than about 10%, fewer than about 9%, fewer than about 8%, fewer than about 7%, fewer than about 6%, fewer than about 5%, fewer than about 4%, fewer than about 4%, fewer than about 3%, fewer than about 2%, fewer than about 1%, or less than 1%, of cells that are not LSC, as defined by the terms herein. Some embodiments of these aspects further encompass methods to expand a population of substantially pure or enriched LSCs, wherein the expanded population of c-kit positive LSCs s is also a substantially pure or enriched population of c-kit positive LSCs.

The term "substantially negative," with respect to a particular marker presence in a cell population, refers to a population of cells that is not more than about 1%, not more than about 0.9%, not more than about 0.8%, not more than about 0.7%, not more than about 0.6%, not more than about 0.5%, not more than about 0.4%, not more than about 0.3%, not more than about 0.2%, or not more than about 0.1% positive for that marker, with respect to the cells making up a total cell population.

The terms "enriching" or "enriched" are used interchangeably herein and mean that the yield (fraction) of cells of one type, such as LSCs for use in the methods described herein, is increased by at least 15%, by at least 20%, by at least 25%, by at least 30%, by at least 35%, by at least 40%, by at least 45%, by at least 50%, by at least 55%, by at least 60%, by at least 65%, by at least 70%, or by at least 75%, over the fraction of cells of that type in the starting biological sample, culture, or preparation. A population of c-kit positive LSCs obtained for use in the methods described herein is most preferably at least 60% enriched for c-kit positive LSCs.

In some embodiments, markers specific for LSCs are used to isolate or enrich for these cells. A "marker," as used herein, describes the characteristics and/or phenotype of a cell. Markers can be used for selection of cells comprising characteristics of interest. Markers will vary with specific cells. Markers are characteristics, whether morphological, functional or biochemical (enzymatic), particular to a cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, appearance (e.g., smooth, translucent), and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. Markers may be detected by any method available to one of skill in the art.

Accordingly, as used herein, a "cell-surface marker" refers to any molecule that is expressed on the surface of a cell. Cell-surface expression usually requires that a molecule possesses a transmembrane domain. Some molecules that are normally not found on the cell-surface can be engineered by recombinant techniques to be expressed on the surface of a cell. Many naturally occurring cell-surface markers are termed "CD" or "cluster of differentiation" molecules. Cell-surface markers often provide antigenic determinants to which antibodies can bind to. A cell-surface marker of particular relevance to the methods described herein is CD117 or c-kit. The useful LSCs according to the compositions and method preferably express c-kit or in other words, they are c-kit positive.

A cell can be designated "positive" or "negative" for any cell-surface marker or other intracellular marker, and both such designations are useful for the practice of the methods described herein. A cell is considered "positive" for a cell-surface marker if it expresses the marker on its cell-surface or intracellularly in amounts sufficient to be detected using methods known to those of skill in the art, such as contacting a cell with an antibody that binds specifically to that marker, and subsequently performing flow cytometric analysis of such a contacted cell to determine whether the antibody is bound the cell. It is to be understood that while a cell can express messenger RNA for a cell-surface marker, in order to be considered positive for the methods described herein, the cell must express it on its surface. Similarly, a cell is considered "negative" for a cell-surface marker or other intracellular marker if it does not express the marker in amounts sufficient to be detected using methods known to those of skill in the art, such as contacting a cell with an antibody that binds specifically to that marker and subsequently performing flow cytometric analysis of such a contacted cell to determine whether the antibody is bound the cell.

In some embodiments of all aspects of the compositions and methods described, the c-kit positive LSCs are negatively selected and the selection uses an agent specific for a cell surface marker. In some embodiments of all aspects of the compositions and methods described, the cell surface marker is a lineage specific marker such as hematopoietic lineage, mast cell lineage, mesenchymal stromal cell lineage, epithelial lineage and/or endothelial cell lineage.

In some embodiments of all aspects of the compositions and methods described, in the context of negative selection, where agents specific for lineage markers are used, all of the agents can comprise the same label or tag, such as fluorescent tag, and thus all cells positive for that label or tag can be excluded or removed, leaving the lineage marker-negative LSCs, lung progenitor cells and/or lung precursor cells for use in the methods described herein. This is negative selection, selecting for those cells that did not contact with the agents specific for lineage markers.

Accordingly, as defined herein, an "agent specific for a cell-surface marker or other intracellular marker" refers to an agent that can selectively react with or bind to that cell-surface marker or other intracellular marker, but has little or no detectable reactivity to another cell-surface marker, other intracellular marker or antigen. For example, an agent specific for c-kit will not identify or bind to CD49e. Thus, agents specific for cell-surface markers or other intracellular marker recognize unique structural features of the markers. In some embodiments, an agent specific for a marker binds to the marker, but does not cause initiation of downstream signaling events mediated by that marker, for example, a non-activating antibody. Agents specific for cell-surface molecules include, but are not limited to, antibodies or antigen-binding fragments thereof, natural or recombinant ligands, small molecules, nucleic acid sequence and nucleic acid analogues, intrabodies, aptamers, and other proteins or peptides.

In some embodiments of all aspects of the compositions and methods described, the preferred agents specific for cell-surface markers used for isolating LSCs are antibody agents that specifically bind the cell-surface markers, and can include polyclonal and monoclonal antibodies, and antigen-binding derivatives or fragments thereof. Well-known antigen binding fragments include, for example, single domain antibodies (dAbs; which consist essentially of single VL or VH antibody domains), Fv fragment, including single chain Fv fragment (scFv), Fab fragment, and F(ab')2 fragment. Methods for the construction of such antibody molecules are well known in the art. Accordingly, as used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments may be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings known to those skilled in the art, e.g., in Klein, "Immunology" (John Wiley, New York, N.Y., 1982); Clark, W. R. (1986); in "The Experimental Foundations of Modern Immunology" (Wiley & Sons, Inc., New York); and Roitt, I. (1991) "Essential Immunology", 7th Ed., (Blackwell Scientific Publications, Oxford). Such antibodies or antigen-binding fragments are available commercially from vendors such as R&D Systems, BD Biosciences, e-Biosciences and Miltenyi, or can be raised against these cell-surface markers or other intracellular marker by methods known to those skilled in the art.

In some embodiments of all aspects of the compositions and methods described, an agent specific for a cell-surface molecule or other intracellular marker, such as an antibody or antigen-binding fragment, is labeled with a tag to facilitate the isolation of the lung stem cells. The terms "label" or "tag", as used herein, refer to a composition capable of producing a detectable signal indicative of the presence of a target, such as, the presence of a specific cell-surface marker in a biological sample. Suitable labels include fluorescent molecules, radioisotopes, nucleotide chromophores, enzymes, substrates, chemiluminescent moieties, magnetic particles, bioluminescent moieties, and the likes. As such, a label is any composition detectable by spectroscopic, photochemical, biochemical, immunochemical, electrical, optical or chemical means needed for the methods to isolate and enrich for LSCs, lung progenitor cell and lung precursor cells.

The terms "labeled antibody" or "tagged antibody", as used herein, includes antibodies that are labeled by detectable means and include, but are not limited to, antibodies that are fluorescently, enzymatically, radioactively, and chemiluminescently labeled. Antibodies can also be labeled with a detectable tag, such as c-Myc, HA, VSV-G, HSV, FLAG, V5, or HIS, which can be detected using an antibody specific to the tag, for example, an anti-c-Myc antibody. Various methods of labeling polypeptides and glycoproteins are known in the art and may be used. Non-limiting examples of fluorescent labels or tags for labeling the antibodies for use in the methods of invention include hydroxycoumarin, succinimidyl ester, aminocoumarin, succinimidyl ester, methoxycoumarin, Cascade Blue, Hydrazide, Pacific Blue, maleimide, Pacific Orange, lucifer yellow, NBD, NBD-X, R-phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), Fluor X, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, ALEXA FLUOR® 350, ALEXA FLUOR® 405, ALEXA FLUOR® 430, ALEXA FLUOR® 488, ALEXA FLUOR® 500, ALEXA FLUOR® 514, ALEXA FLUOR® 532, ALEXA FLUOR® 546, ALEXA FLUOR®555, ALEXA FLUOR® 568, ALEXA FLUOR®594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, ALEXA FLUOR® 790, Cy2, Cy3, Cy3B, Cy3.5, Cy5, Cy5.5 or Cy7.

In some embodiments of all aspects of the compositions and methods described, a variety of methods to isolate a substantially pure or enriched population of c-kit positive LSCs are available to a skilled artisan, including immunoselection techniques, such as high-throughput cell sorting using flow cytometric methods, affinity methods with antibodies labeled to magnetic beads, biodegradable beads, non-biodegradable beads, and antibodies panned to surfaces including dishes and combination of such methods.

In some embodiments of all aspects of the compositions and methods described, the isolation and enrichment for populations of LSCs can be performed using bead based sorting mechanisms, such as magnetic beads. In such methods, a digested lung tissue sample is contacted with magnetic beads coated with antibodies against one or more specific cell-surface antigens, such as c-kit. This causes the cells in the sample that express the respective antigen to attach to the magnetic beads. After a period of time to allow the c-kit positive cells bind the beads, the mixture of cell and beads are exposed to a strong magnetic field, such as a column or rack having a magnet. The cells attached to the beads (expressing the cell-surface marker) stay on the column or sample tube, while other cells (not expressing the cell-surface marker) flow through or remain in solution. Using this method, cells can be separated positively or negatively, or using a combination therein, with respect to the particular cell-surface markers.

In some embodiments of all aspects of the compositions and methods described, magnetic activated cell sorting (MACS) strategies are used for isolation and pre-selection of LSCs. In some embodiments, LSCs are isolated in the presence of human plasma or human serum albumin (HSA), such as 2% HSA.

In some preferred embodiments of all aspects of the compositions and methods described, LSCs are isolated or enriched using positive selection for the cell-surface marker c-kit.

In other embodiments of all aspects of the compositions and methods described, one or more additional cell-surface markers are used for isolating and/or enriching for LSCs, using positive or negative selection methods, or a combination therein. Such additional cell-surface markers include, but are not limited to, CD2, CD3, CD6, CD8, CD14, CD16, CD19, CD20, CD24, CD29, CD34, CD44, CD45, CD49d, CD49e, CD66b, CD90, CD105, CD133, glycophorin A, TTF1, p63, pan-cytokeratin, cytokeratin 5, CC10, aquaporin-5, SPC, Est1, vWF1, GATA 6, and alpha-SMA.

As defined herein, "positive selection" refers to techniques that result in the isolation or enrichment of cells expressing specific cell-surface markers or intracellular proteins, while "negative selection" refers techniques that result in the isolation or enrichment of cells that do not expressing specific cell-surface markers or intracellular proteins. Negative selection can be performed by any method known in the art. For example, typical negative selection is carried out by removing the cells that do express the marker of interest.

In some embodiments of all aspects of the compositions and methods described, beads can be coated with antibodies by a skilled artisan using standard techniques known in the art, such as commercial bead conjugation kits. In some embodiments, a negative selection step is performed to remove cells expressing one or more lineage markers, followed by fluorescence activated cell sorting to positively select LSCs expressing one or more specific cell-surface markers. For example, in a negative selection protocol, a digested lung tissue sample, is first contacted with labeled antibodies specific for cell-surface markers of interest, such as CD2, CD3, CD6, CD8, CD34, CD49e, and CD66b and the sample is then contacted with beads that are specific for the labels of the antibodies, and the cells expressing the markers CD2, CD3, CD6, CD8, CD34, CD49e, and CD66b are removed using immunomagnetic lineage depletion.

A number of different cell-surface markers have specific expression on specific differentiated cell lineages, and are not expressed by the c-kit positive LSCs isolated for the methods described herein. Accordingly, when agents specific for these lineage cell-markers are contacted with c-kit positive LSCs, the cells will be "negative." Lineage cell-markers that are not expressed by the c-kit positive LSCs described herein are but not limited to, CD13 and CD33 (expressed on myeloid cells); CD71 (expressed on erythroid cells); CD19 and B220 (expressed on B cells), CD61 (expressed on human megakaryocytic cells); Mac-1 (CD11b/CD18) (expressed on monocytes); Gr-1 (expressed on granulocytes); Ter119 (expressed on erythroid cells); and Il7Ra, CD2, CD3, CD4, CD5, CD8 (expressed on T cells); CD14, CD56, and CD235a; TTF1, p63, pan-cytokeratin, cytokeratin 5, CC10, aquaporin-5 and SPC (for epithelial lineage); Est1, vWF1, GATA 6, and alpha-SMA (for endothelial cell and smooth muscle cell lineage); CD6, CD29, CD49d, CD49e, CD45 and tryptase (for mast cell lineage); CD44, CD90 and CD105 (for mesenchymal stromal cell lineage); and CD34, CD45, and CD133 (for general hematopoietic lineage).

In some embodiments of all aspects of the compositions and methods described, flow cytometric methods, alone or in combination with magnetic bead based methods, are used to isolate or enrich for c-kit positive LSCs. As defined herein, "flow cytometry" refers to a technique for counting and examining microscopic particles, such as cells and chromosomes, by suspending them in a stream of fluid and passing them through an electronic detection apparatus. Flow cytometry allows simultaneous multiparametric analysis of the physical and/or chemical parameters of up to thousands of particles per second, such as fluorescent parameters. Modern flow cytometric instruments usually have multiple lasers and fluorescence detectors. Increasing the number of lasers and detectors allows for labeling by multiple antibodies, and can more precisely identify a target population by their phenotypic markers. Certain flow cytometric instruments can take digital images of individual cells, allowing for the analysis of fluorescent signal location within or on the surface of cells.

A common variation of flow cytometric techniques is to physically sort particles based on their properties, so as to purify populations of interest, using "fluorescence-activated cell sorting" As defined herein, "fluorescence-activated cell sorting" or "flow cytometric based sorting" methods refer to flow cytometric methods for sorting a heterogeneous mixture of cells from a single biological sample into one or more containers, one cell at a time, based upon the specific light scattering and fluorescent characteristics of each cell and provides fast, objective and quantitative recording of fluorescent signals from individual cells as well as physical separation of cells of particular interest. Accordingly, in those embodiments when the agents specific for cell-surface markers are antibodies labeled with tags that can be detected by a flow cytometer, fluorescence-activated cell sorting (FACS) can be used in and with the methods described herein to isolate and enrich for populations of LSCs.

Expansion of LPCs

In some embodiments of all aspects of the compositions and methods described, the population of isolated and substantially enriched c-kit positive LSCs are further expanded to increase in numbers prior to their use in the therapeutic methods described herein.

In some embodiments of all aspects of the compositions and methods described, c-kit positive LSCs isolated or enriched by using the methods and techniques described herein are expanded in culture, i.e., the cell numbers are increased outside the body of the subject, using methods known to one of skill in the art, prior to administration to a subject in need.

In one embodiment of all aspects of the compositions and methods described, the isolated c-kit positive LSCs obtained are expanded in culture according to the following method. One skilled in the art would be able to make minor adjustment to the method as needed. The isolated c-kit positive cells are plated in modified F12K medium containing F12 medium (GIBCO, Grand Island, N.Y.) supplemented with 5-10% FBS (GIBCO) and insulin-selenium-transferrin mixture (SIGMA, St. Louis, Mo.) under standard tissue culture conditions, e.g., 95% air, 5% $CO_2$, 37° C. After reaching confluence, the cells from one confluent plate are passaged to several other plates to expand the culture using standard tissue culture protocol of handling the cells.

In some embodiments of all aspects of the compositions and methods described, such expansion methods can comprise, for example, culturing the c-kit positive LSCs in serum-free medium supplemented with factors and/or under conditions that cause expansion of LSCs, such as stem cell factor, IL-3, and GM-CSF. In some embodiments of all aspects of the compositions and methods described, the c-kit positive LSCs can further be cultured with factors and/or under conditions aimed at inducing differentiation of the LSCs to respiratory epithelia, such as using small airway growth medium, modified mouse tracheal epithelial cell medium, or serum-free medium supplemented with retinoic acid and/or keratinocyte growth factor. Some non-limiting expansion methods suitable for use with the methods described herein can be found in the Example section.

In other embodiments of all aspects of the compositions and methods described, c-kit positive LSCs are expanded by adapting not more than about 0.5%, nanotechnological or nanoengineering methods, as reviewed in Lu J et al., "A Novel Technology for Hematopoietic Stem Cell Expansion using Combination of Nanofiber and Growth Factors." Recent Pat Nanotechnol. 2010 4(2):125-35. For example, in some embodiments, nanoengineering of stem cell microenvironments can be performed. As used herein, secreted factors, stem cell-neighboring cell interactions, extracellular matrix (ECM) and mechanical properties collectively make up the "stem cell microenvironment". Stem cell microenvironment nanoengineering can comprise the use of micro/nanopatterned surfaces, nanoparticles to control release growth factors and biochemicals, nanofibers to mimic extracellular matrix (ECM), nanoliter-scale synthesis of arrayed biomaterials, self-assembly peptide system to mimic signal clusters of stem cells, nanowires, laser fabricated nanogrooves, and nanophase thin films to expand LSCs.

In other embodiments of all aspects of the compositions and methods described, the c-kit positive LSCs are genetically manipulated, e.g., transfected with an exogenous nucleic acid. Nanoengineering can be used for the transfection and genetic manipulation in LSCs, such as nanoparticles for in vivo gene delivery, nanoneedles for gene delivery to LSCs, self-assembly peptide system for LSC transfection, nanowires for gene delivery to LSCs, and micro/nanofluidic devices for LSC electroporation.

In other embodiments of all aspects of the compositions and methods described, the c-kit positive LSCs isolated or enriched for use in the methods can be expanded using bioreactors.

The terms "increased," "increase" or "expand", when used in the context of LSC expansion, generally mean an increase in the number of LSCs by a statistically significant amount; for the avoidance of any doubt, the terms "increased," "increase," "expand" or "expanded," mean an increase, as compared to a reference level, of at least about 10%, of at least about 15%, of at least about 20%, of at least about 25%, of at least about 30%, of at least about 35%, of at least about 40%, of at least about 45%, of at least about 50%, of at least about 55%, of at least about 60%, of at least about 65%, of at least about 70%, of at least about 75%, of at least about 80%, of at least about 85%, of at least about 90%, of at least about 95%, or up to and including a 100%, or at least about a 2-fold, or at least about a 3-fold, or at least about a 4-fold, or at least about a 5-fold, at least about a 6-fold, or at least about a 7-fold, or at least about a 8-fold, at least about a 9-fold, or at least about a 10-fold increase, or any increase of 10-fold or greater, as compared to a control or reference level. A control/reference sample or level is used herein to describe a population of cells obtained from the same biological source that has, for example, not been expanded using the methods described herein, e.g., at the start of the expansion culture or the initial number of cells added to the expansion culture.

Storage of Lung Tissue Samples and/or Lung Stem Cells

In some embodiments of all aspects of the compositions and methods described, the lung tissue samples are stored prior to use, i.e., prior to the extraction, isolation or selection of the c-kit positive LSCs therein. In some embodiments of all aspects of the compositions and methods described, the digested lung tissue sample is stored prior to extraction or selection of the c-kit positive LSCs therein. In some embodiments of all aspects of the compositions and methods described, the isolated c-kit positive LSCs are stored. In other embodiments, the c-ki of all aspects of the compositions and methods described t positive LSCs are first isolated and/or expanded prior to storage. In one embodiment, the storage is by cryopreservation. The LSCs are thawed when needed for the therapeutic methods described herein.

In some embodiments of all aspects of the compositions and methods described, the lung tissue samples or isolated c-kit positive LSCs (expanded or otherwise) are frozen prior to their use in the methods described herein. Freezing the samples can be performed in the presence of one or more different cryoprotectants for minimizing cell damage during the freeze-thaw process. For example, dimethyl sulfoxide (DMSO), trehalose, or sucrose can be used.

Administration and Uses of LCSs in Regenerative Medicine

Certain embodiments described herein are based on the discovery of somatic stem cells human in the human lung tissue and that these human lung stem cells (hLSCs) can repair damaged lung tissues in mice. When hLSCs were placed into a mouse with damaged lungs, long-term engraftment of the administered hLSCs cells occurred and these hLSCs differentiated into respiratory epithelium and vessels, which led to consequent lung growth and alveolar regeneration and repair. This experimental observation indicated that isolated c-kit positive LSCs can be used for pulmonary vascular regeneration and alveolar development.

Accordingly, provided herein are methods for the treatment and/or prevention of a respiratory/lung disease or disorder in a subject in need thereof. As used herein, the term "repiratory disease or disorder" "lung disease or disorder" and "lung disorder" are used interchangeably. Some of these methods involve administering to a subject a therapeutically effective amount of isolated c-kit positive LSCs using intrapulmonary administration, such as an intransal or intratracheal route. In some aspects of these methods, a therapeutically effective amount of isolated c-kit positive LSCs is administered using a systemic, such as an intraperitoneal or intravenous route. In other aspects of these methods, a therapeutically effective amount of isolated c-kit positive LSCs is administered using both intrapulmonary and intraperitoneal administration. These methods are particularly aimed at therapeutic and prophylactic treatments of human subjects having or at risk for a respiratory disease or disorder, e.g., a subject having asbestos exposure. The isolated or enriched c-kit positive LSCs described herein can be administered to a selected subject having any respiratory disease or disorder or is predispose to developing one, the administration can be by any appropriate route which results in an effective treatment in the subject. In some embodiments of all aspects of the therapeutic methods described herein, a subject having a respiratory disorder is first selected prior to administration of the cells.

The terms "subject", "patient" and "individual" are used interchangeably herein, and refer to an animal, for example, a human from whom cells for use in the methods described herein can be obtained (i.e., donor subject) and/or to whom treatment, including prophylactic treatment, with the cells as described herein, is provided, i.e., recipient subject. For treatment of those conditions or disease states that are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g., dog, cat, horse, and the like, or food production mammal, e.g., cow, sheep, pig, and the like.

Accordingly, in some embodiments of the therapeutic methods described herein, a subject is a recipient subject, i.e., a subject to whom the isolated c-kit positive LSCs are being administered, or a donor subject, i.e., a subject from whom a lung tissue sample comprising c-kit positive LSCs are being obtained. A recipient or donor subject can be of any age. In some embodiments, the subject is a "young subject," defined herein as a subject less than 10 years of age. In other embodiments, the subject is an "infant subject," defined herein as a subject is less than 2 years of age. In some embodiments, the subject is a "newborn subject," defined herein as a subject less than 28 days of age. In a preferred embodiment, the subject is a human adult.

In some embodiments of the therapeutic methods described herein, the isolated c-kit positive LSCs population being administered comprises allogeneic LSCs obtained from one or more donors. As used herein, "allogeneic" refers to LSCs or lung tissue samples comprising LSCs obtained from one or more different donors of the same species, where the genes at one or more loci are not identical. For example, an isolated c-kit positive LSCs population being administered to a subject can be obtained from the lung tissue obtained from one more unrelated donor subjects, or from one or more non-identical siblings or other sources. In some embodiments, syngeneic isolated c-kit positive LSCs populations is used, such as those obtained from genetically identical animals, or from identical twins. In other embodiments of this aspect, the isolated c-kit positive LSCs are autologous LSCs. As used herein, "autologous" refers to LSCs or lung tissue samples comprising c-kit positive LSCs obtained or isolated from a subject and being administered to the same subject, i.e., the donor and recipient are the same.

Lung disease is any disease or disorder that occurs in the lungs or that causes the lungs to not work properly. There are three main types of lung disease. Most lung diseases actually involve a combination of these categories: (1) Airway diseases—These diseases affect the tubes (airways) that carry oxygen and other gases into and out of the lungs. These diseases cause a narrowing or blockage of the airways. They include asthma, emphysema, and chronic bronchitis. People with airway diseases sometimes describe the feeling as "trying to breathe out through a straw." (2) Lung tissue diseases—These diseases affect the structure of the lung tissue. Scarring or inflammation of the tissue makes the lungs unable to expand fully ("restrictive lung disease"). It also makes the lungs less capable of taking up oxygen (oxygenation) and releasing carbon dioxide. Pulmonary fibrosis and sarcoidosis are examples of lung tissue diseases. People sometimes describe the feeling as "wearing a too-tight sweater or vest" that won't allow them to take a deep breath. (3) Pulmonary circulation diseases—These diseases affect the blood vessels in the lungs. They are caused by clotting, scarring or inflammation of the blood vessels in the lungs. They affect the ability of the lungs to take up oxygen and to release carbon dioxide. These diseases can also affect heart function.

The most common lung diseases include: asthma, chronic bronchitis, chronic obstructive pulmonary disease (COPD), emphysema, pulmonary fibrosis and sarcoidosis. Other lung diseases include: asbestosis, aspergilloma, aspergillosis, acute invasive atelectasis, eosinophilic pneumonia, lung cancer, metastatic lung cancer, necrotizing pneumonia, pleural effusion pneumoconiosis, pneumocystosis, pneumonia, pneumonia in immunodeficient patient, pneumothorax, pulmonary actinomycosis, pulmonary alveolar proteinosis, pulmonary anthrax, pulmonary arteriovenous malformation, pulmonary edema, pulmonary embolus, pulmonary histiocytosis X (eosinophilic granuloma), pulmonary hypertension, pulmonary nocardiosis, pulmonary tuberculosis, pulmonary veno-occlusive disease, and rheumatoid lung disease.

The methods described herein can be used to treat, ameliorate the symptoms, prevent and/or slow the progression of a number of respiratory diseases or their symptoms, such as those resulting in pathological damage to lung or airway architecture and/or alveolar damage. The terms "respiratory disorder," "respiratory disease," "pulmonary disease," and "pulmonary disorder," are used interchangeably herein and refer to any condition and/or disorder relating to respiration and/or the respiratory system, including the lungs, pleural cavity, bronchial tubes, trachea, upper respiratory tract, airways, or other components or structures of the respiratory system. Such respiratory diseases include, but are not limited to, bronchopulmonary dysplasia (BPD), chronic obstructive pulmonary disease (COPD) condition, cystic fibrosis, bronchiectasis, cor pulmonale, pneumonia, lung abcess, acute bronchitis, chronic bronchitis, emphysema, pneumonitis, e.g., hypersensitivity pneumonitis or pneumonitis associated with radiation exposure, alveolar lung diseases and interstitial lung diseases, environmental lung disease (e.g., associated with asbestos, fumes or gas exposure), aspiration pneumonia, pulmonary hemorrhage syndromes, amyloidosis, connective tissue diseases, systemic sclerosis, ankylosing spondylitis, pulmonary actinomycosis, pulmonary alveolar proteinosis, pulmonary anthrax, pulmonary edema, pulmonary embolus, pulmonary inflammation, pulmonary histiocytosis X, pulmonary hypertension, surfactant deficiencies, pulmonary hypoplasia, pulmonary neoplasia, pulmonary nocardiosis, pulmonary tuberculosis, pulmonary veno-occlusive disease, rheumatoid lung disease, sarcoidosis, post-pneumonectomy, Wegener's granulomatosis, allergic granulomatosis, granulomatous vasculitides, eosinophilia, asthma and airway hyperreactivity (AHR), e.g., mild intermittent asthma, mild persistent asthma, moderate persistent asthma, severe persistent asthma, acute asthma, chronic asthma, atopic asthma, allergic asthma or idiosyncratic asthma, cystic fibrosis and associated conditions, e.g., allergic bronchopulmonary aspergillosis, chronic sinusitis, pancreatic insufficiency, lung or vascular inflammation, bacterial or viral infection, e.g., *Haemophilus influenzae, S. aureus, Pseudomonas aeruginosa* or RSV infection or an acute or chronic adult or pediatric respiratory distress syndrome (RDS) such as grade I, II, III or IV RDS or an RDS associated with, e.g., sepsis, pneumonia, reperfusion, atelectasis or chest trauma.

Chronic obstructive pulmonary diseases (COPDs) include conditions where airflow obstruction is located at upper airways, intermediate-sized airways, bronchioles or parenchyma, which can be manifested as, or associated with, tracheal stenosis, tracheal right ventricular hypertrophy pulmonary hypertension, polychondritis, bronchiectasis, bronchiolitis, e.g., idiopathic bronchiolitis, ciliary dyskinesia, asthma, emphysema, connective tissue disease, bronchiolitis of chronic bronchitis or lung transplantation.

The methods described herein can also be used to treat or ameliorate acute or chronic asthma or their symptoms or complications, including airway epithelium injury, airway smooth muscle spasm or airway hyperresponsiveness, airway mucosa edema, increased mucus secretion, excessive, T cell activation, or desquamation, atelectasis, corpulmonale, pneumothorax, subcutaneous emphysema, dyspnea, coughing, wheezing, shortness of breath, tachypnea, fatigue, decreased forced expiratory volume in the 1st second (FEV1), arterial hypoxemia, respiratory acidosis, inflammation including unwanted elevated levels of mediators such as IL-4, IL-5, IgE, histamine, substance P, neurokinin A, calcitonin gene-related peptide or arachidonic acid metabolites such as thromboxane or leukotrienes (LTD4 or LTC4), and cellular airway wall infiltration, e.g., by eosinophils, lymphocytes, macrophages or granulocytes.

Any of these lung diseases and disorders, and other respiratory or pulmonary conditions or symptoms are described elsewhere, e.g., The Merck Manual, 17.sup.th edition, M. H. Beers and R. Berkow editors, 1999, Merck Research Laboratories, Whitehouse Station, N.J., ISBN 0911910-10-7, or in other references cited herein it its entirety. In some of these conditions, where inflammation plays a role in the pathology of the condition, therapeutic agents used together with the c-kit LSCs can ameliorate or slow the progression of the condition by reducing damage from inflammation, such as damage to the lung epithelium. In other cases, therapeutic agents used together with the c-kit LSCs can act to limit pathogen replication or pathogen-associated lung tissue damage.

As used herein, the terms "administering," "introducing", "transplanting" and "implanting" are used interchangeably in the context of the placement of cells, e.g., c-kit positive LSCs, of the invention into a subject, by a method or route which results in at least partial localization of the introduced cells at a desired site, such as a site of injury or repair, such that a desired effect(s) is produced. The cells e.g., c-kit positive LSCs, or their differentiated progeny (e.g., respiratory epithelium-like cells) can be implanted directly to the respiratory airways, or alternatively be administered by any appropriate route which results in delivery to a desired location in the subject where at least a portion of the implanted cells or components of the cells remain viable. The period of viability of the cells after administration to a subject can be as short as a few hours, e.g., twenty-four hours, to a few days, to as long as several years, i.e., long-term engraftment. For example, in some embodiments of all aspects of the therapeutic methods described herein, an effective amount of an isolated or enriched population of isolated c-kit positive LSCs is administered directly to the lungs of an infant suffering from bronchopulmonary dysplasia by intratracheal administration. In other embodiments of all aspects of the therapeutic methods described herein, the population of isolated and enriched c-kit positive LSCs is administered via an indirect systemic route of administration, such as an intraperitoneal or intravenous route.

When provided prophylactically, the isolated and enriched c-kit positive LSCs can be administered to a subject in advance of any symptom of a respiratory disorder, e.g., asthma attack or for a cystic fibrosis subject. Accordingly, the prophylactic administration of an isolated or enriched for c-kit positive LSCs population serves to prevent a respiratory disorder, or further progress of respiratory diseases as disclosed herein.

When provided therapeutically, isolated and enriched c-kit positive LSCs are provided at (or after) the onset of a symptom or indication of a respiratory disorder, e.g., upon the onset of COPD.

As used herein, the terms "treat," "treatment," "treating," or "amelioration" refer to therapeutic treatment, wherein the object is to reverse, alleviate, ameliorate, decrease, inhibit, or slow down the progression or severity of a condition associated with, a disease or disorder. The term "treating" includes reducing or alleviating at least one adverse effect or symptom of a condition, disease or disorder associated with an inflammatory disease, such as, but not limited to, asthma. Treatment is generally "effective" if one or more symptoms or clinical markers are reduced as that term is defined herein. Alternatively, treatment is "effective" if the progression of a disease is reduced or halted. That is, "treatment" includes not just the improvement of symptoms or markers, but also a cessation or at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. In some embodiments, "treatment" and "treating" can also mean prolonging survival of a subject as compared to expected survival if the subject did not receiving treatment.

As used herein, the term "prevention" refers to prophylactic or preventative measures wherein the object is to prevent or delay the onset of a disease or disorder, or delay the onset of symptoms of associated with a disease or disorder. In some embodiments, "prevention" refers to slowing down the progression or severity of a condition or the deterioration of lung function associated with a lung disease or disorder.

In another embodiment, "treatment" of a lung disease also includes providing relief from the symptoms or side-effects of the disease (including palliative treatment). For example, any reduction in inflammation, bronchospasm, bronchoconstriction, shortness of breath, wheezing, lower extremity edema, ascites, productive cough, hemoptysis, or cyanosis in a subject suffering from a respiratory disorder, such as asthma, no matter how slight, would be considered an alleviated symptom. In some embodiments of the aspects described herein, the symptoms or a measured parameter of a disease or disorder are alleviated by at least 5%, at least 10%, at least 20%, at least 30%, at least 40%, at least 50%, at least 60%, at least 70%, at least 80%, or at least 90%, upon administration of a population of isolated and enriched for LSCs, as compared to a control or non-treated subject.

Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total usage of the compositions as disclosed herein will be decided by the attending physician within the scope of sound medical judgment. The exact amount required will vary depending on factors such as the type of lung disease being treated, degree of damaged, whether the goal in for treatment or prevention or both, age of the subject, the amount of cells available etc. Thus, one of skill in the art realizes that a treatment may improve the disease condition, but may not be a complete cure for the disease.

In one embodiment of all aspects of the therapeutic methods described, the term "effective amount" as used herein refers to the amount of a population of isolated or enriched for c-kit positive LSCs needed to alleviate at least one or more symptoms of the respiratory disease or disorder, and relates to a sufficient amount of pharmacological composition to provide the desired effect, e.g., treat a subject having bronchopulmonary dysplasia. The term "therapeutically effective amount" therefore refers to an amount isolated and enriched for c-kit positive LSCs using the therapeutic methods as disclosed herein that is sufficient to effect a particular effect when administered to a typical subject, such as one who has or is at risk for bronchopulmonary dysplasia.

In another embodiment of all aspects of the methods described, an effective amount as used herein would also include an amount sufficient to prevent or delay the development of a symptom of the disease, alter the course of a symptom disease (for example but not limited to, slow the progression of a symptom of the disease), or even reverse a symptom of the disease. The effective amount of c-kit positive cells need for a particular effect will vary with each individual and will also vary with the type of lung disease addressed. Thus, it is not possible to specify the exact "effective amount". However, for any given case, an appropriate "effective amount" can be determined by one of ordinary skill in the art using routine experimentation.

In some embodiments of all aspects of the therapeutic methods described, the subject is first diagnosed as having a disease or disorder affecting the lung tissue prior to administering the cells according to the methods described herein. In some embodiments of all aspects of the therapeutic methods described, the subject is first diagnosed as being at risk of developing lung disease or disorder prior to administering the cells, e.g., a long time smoker, a coal miner and a person having prior exposure to asbestos.

For use in all aspects of the therapeutic methods described herein, an effective amount of isolated c-kit positive LSCs comprises at least $10^2$, at least $5 \times 10^2$, at least $10^3$, at least $5 \times 10^3$ LSCs, at least $10^4$, at least $5 \times 10^4$, at least $10^5$, at least $2 \times 10^5$, at least $3 \times 10^5$, at least $4 \times 10^5$, at least $5 \times 10^5$, at least $6 \times 10^5$, at least $7 \times 10^5$, at least $8 \times 10^5$, at least $9 \times 10^5$, or at least $1 \times 10^6$ c-kit positive LSCs or multiples thereof per administration. In some embodiments, more than one administration of isolated c-kit positive LSCs is performed to a subject. The multiple administration of isolated c-kit positive LSCs can take place over a period of time. The c-kit positive LSCs can be isolated or enriched for from one or more donors, or can be obtained from an autologous source.

Exemplary modes of administration for use in the methods described herein include, but are not limited to, injection, intrapulmonary (including intranasal and intratracheal) infusion, inhalation (including intranasal), ingestion, and rectal administration. "Injection" includes, without limitation, intravenous, intraarterial, intraventricular, intracardiac, transtracheal injection and infusion. The phrases "parenteral administration" and "administered parenterally" as used herein, refer to modes of administration other than enteral and topical administration, usually by injection, and includes, without limitation, intravenous, intraventricular, intracardiac, transtracheal injection and infusion.

In preferred embodiments of all aspects of the therapeutic methods described, an effective amount of isolated c-kit positive LSCs is administered to a subject by intrapulmonary administration or delivery. As defined herein, intrapulmonary administration or intrapulmonary delivery refers to all routes of administration whereby a population of isolated and enriched for c-kit positive LSCs, is administered in a way that results in direct contact of these cells with the airways of a subject, including, but not limited to, transtracheal, intratracheal, and intranasal administration. In such embodiments, the cells are injected into the nasal passages or trachea. In some embodiments, the cells are directly inhaled by a subject. In some embodiments of all aspects of the therapeutic methods described, intrapulmonary delivery of cells includes administration methods whereby cells are administered, for example as a cell suspension, to an intubated subject via a tube placed in the trachea or "tracheal intubation."

As used herein, "tracheal intubation" refers to the placement of a flexible tube, such as a plastic tube, into the trachea. The most common tracheal intubation, termed herein as "orotracheal intubation" is where, with the assistance of a laryngoscope, an endotracheal tube is passed through the mouth, larynx, and vocal cords, into the trachea. A bulb is then inflated near the distal tip of the tube to help secure it in place and protect the airway from blood, vomit, and secretions. In some embodiments of all aspects of the therapeutic methods described, cells are administered to a subject having "nasotracheal intubation," which is defined as a tracheal intubation where a tube is passed through the nose, larynx, vocal cords, and trachea.

In some embodiments of all aspects of the therapeutic methods described, an effective amount of isolated and enriched c-kit positive LSCs is administered to a subject by systemic administration, such as intravenous administration.

The phrases "systemic administration," "administered systemically", "peripheral administration" and "administered peripherally" as used herein refer to the administration of population of LSCs other than directly into the lung, such that it enters, instead, the subject's circulatory system.

In some embodiments of all aspects of the therapeutic methods described, one or more routes of administration are used in a subject to achieve distinct effects. For example, isolated or enriched population of c-kit positive LSCs are administered to a subject by both intratracheal and intraperitoneal administration routes for treating or repairing respiratory epithelium and for pulmonary vascular repair and regeneration respectively. In such embodiments, different effective amounts of the isolated or enriched c-kit positive LSCs can be used for each administration route.

In some embodiments of all aspects of the therapeutic methods described, the methods further comprise administration of one or more therapeutic agents, such as a drug or a molecule, that can enhance or potentiate the effects mediated by the administration of the isolated or enriched c-kit positive LSCs, such as enhancing homing or engraftment of the LSCs, increasing repair of respiratory epithelia, or increasing growth and regeneration of pulmonary vasculature, i.e., vascular regeneration. The therapeutic agent can be a protein (such as an antibody or antigen-binding fragment), a peptide, a polynucleotide, an aptamer, a virus, a small molecule, a chemical compound, a cell, a drug, etc. As defined herein, "vascular regeneration" refers to de novo formation of new blood vessels or the replacement of damaged blood vessels (e.g., capillaries) after injuries or traumas, as described herein, including but not limited to, respiratory disease. "Angiogenesis" is a term that can be used interchangeably to describe such phenomena.

In some embodiments of all aspects of the therapeutic methods described, the methods further comprise administration of one or more together with growth, differentiation, and angiogenesis agent or factor that are known in the art to stimulated cell growth, differentiation, and angiogenesis in the lung tissue. In some embodiments, any one of these factors can be delivered to prior to or after administering the compositions described herein. Multiple subsequent delivery of any one of these factors can also occur to induce and/or enhance the engraftment, differentiation and/or angiogenesis. Suitable growth factors include but are not limited to transforming growth factor-beta (TGFβ), vascular endothelial growth factor (VEGF), platelet derived growth factor (PDGF), angiopoietins, epidermal growth factor (EGF), bone morphogenic protein (BMP), basic fibroblast growth factor (bFGF), insulin and 3-isobutyl-1-methylxasthine (IBMX). Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, Pa.: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag, and these are hereby incorporated by reference in their entirety.

In one embodiment, the composition can include one or more bioactive agents to induce healing or regeneration of damaged tissue, such as recruiting blood vessel forming cells from the surrounding tissues to provide connection points for the nascent vessels. Suitable bioactive agents include, but are not limited to, pharmaceutically active compounds, hormones, growth factors, enzymes, DNA, RNA, siRNA, viruses, proteins, lipids, polymers, hyaluronic acid, pro-inflammatory molecules, antibodies, antibiotics, anti-inflammatory agents, anti-sense nucleotides and transforming nucleic acids or combinations thereof. Other bioactive agents can promote increase mitosis for cell growth and cell differentiation.

A great number of growth factors and differentiation factors that are known in the art to stimulated cell growth and differentiation of the stem cells and progenitor cells. Suitable growth factors and cytokines include any cytokines or growth factors capable of stimulating, maintaining, and/or mobilizing progenitor cells. They include but are not limited to stem cell factor (SCF), granulocyte-colony stimulating factor (G-CSF), granulocyte-macrophage stimulating factor (GM-CSF), stromal cell-derived factor-1, steel factor, vascular endothelial growth factor (VEGF), TGFβ, platelet derived growth factor (PDGF), angiopoeitins (Ang), epidermal growth factor (EGF), bone morphogenic protein (BMP), fibroblast growth factor (FGF), hepatocyte growth factor, insulin-like growth factor (IGF-1), interleukin (IL)-3, IL-1α, IL-1β, IL-6, IL-7, IL-8, IL-11, and IL-13, colony-stimulating factors, thrombopoietin, erythropoietin, fit3-ligand, and tumor necrosis factor α. Other examples are described in Dijke et al., "Growth Factors for Wound Healing", Bio/Technology, 7:793-798 (1989); Mulder G D, Haberer P A, Jeter K F, eds. Clinicians' Pocket Guide to Chronic Wound Repair. 4th ed. Springhouse, Pa.: Springhouse Corporation; 1998:85; Ziegler T. R., Pierce, G. F., and Herndon, D. N., 1997, International Symposium on Growth Factors and Wound Healing: Basic Science & Potential Clinical Applications (Boston, 1995, Serono Symposia USA), Publisher: Springer Verlag.

In one embodiment of all aspects of the therapeutic methods described, the composition described is a suspension of LSCs in a suitable physiologic carrier solution such as saline. The suspension can contain additional bioactive agents include, but are not limited to, pharmaceutically active compounds, hormones, growth factors, enzymes, DNA, RNA, siRNA, viruses, proteins, lipids, polymers, hyaluronic acid, pro-inflammatory molecules, antibodies, antibiotics, anti-inflammatory agents, anti-sense nucleotides and transforming nucleic acids or combinations thereof.

In certain embodiments of all aspects of the therapeutic methods described, the therapeutic agent is a "pro-angiogenic factor," which refers to factors that directly or indirectly promote new blood vessel formation. The pro-angiogenic factors include, but are not limited to epidermal growth factor (EGF), E-cadherin, VEGF, angiogenin, angiopoietin-1, fibroblast growth factors: acidic (aFGF) and basic (bFGF), fibrinogen, fibronectin, heparanase, hepatocyte growth factor (HGF), angiopoietin, hypoxia-inducible factor-1 (HIF-1), insulin-like growth factor-1 (IGF-1), IGF, BP-3, platelet-derived growth factor (PDGF), VEGF-A, VEGF-C, pigment epithelium-derived factor (PEDF), vascular permeability factor (VPF), vitronection, leptin, trefoil peptides (TFFs), CYR61 (CCN1), NOV (CCN3), leptin, midkine, placental growth factor platelet-derived endothelial cell growth factor (PD-ECGF), platelet-derived growth factor-BB (PDGF-BB), pleiotrophin (PTN), progranulin, proliferin, transforming growth factor-alpha (TGF-alpha), transforming growth factor-beta (TGF-beta), tumor necrosis factor-alpha (TNF-alpha), c-Myc, granulocyte colony-stimulating factor (G-CSF), stromal derived factor 1 (SDF-1), scatter factor (SF), osteopontin, stem cell factor (SCF), matrix metalloproteinases (MMPs), thrombospondin-1 (TSP-1), pleitrophin, proliferin, follistatin, placental growth factor (PlGF), midkine, platelet-derived growth factor-BB (PDGF), and fractalkine, and inflammatory cytokines and chemokines that are inducers of angiogenesis and increased vascularity, e.g., interleukin-3 (IL-3), interleukin-8 (IL-8), CCL2 (MCP-1), interleukin-8 (IL-8) and CCL5 (RANTES). Suitable dosage of one or more therapeutic agents can include a concentration of about 0.1 to about 500 ng/ml, about 10 to about 500 ng/ml, about 20 to about 500 ng/ml, about 30 to about 500 ng/ml, about 50 to about 500 ng/ml, or about 80 ng/ml to about 500 ng/ml. In some embodiments, the suitable dosage of one or more therapeutic agents is about 10, about 25, about 45, about 60, about 75, about 100, about 125, about 150, about 175, about 200, about 225, about 250, about 275, about 300, about 325, about 350, about 375, about 400, about 425, about 450, about 475, or about 500 ng/ml. In other embodiments, suitable dosage of one or more therapeutic agents is about 0.6, about 0.7, about 0.8, about 0.9, about 1.0, about 1.5, or about 2.0 μg/ml.

In some embodiments of all aspects of the therapeutic methods described, the methods further comprise administration of one or more surfactants as therapeutic agents, or may be used in combination with one or more surfactant therapies. Surfactant, as used herein, refers to any surface active agent, including but not limited to wetting agents, surface tension depressants, detergents, dispersing agents and emulsifiers. Particularly preferred are those that from a monomolecular layer over pulmonary alveolar surfaces, including but not limited to lipoproteins, lecithins, phosphatidylglycerol (PG), dipalmitoyl-phosphatidyl choline (DPPG), apoprotein A, apoprotein B, apoprotein C, apoprotein D, palmitoyl oleoyl, phosphatidyl glycerol palmitic and sphygomyelins. Exemplary surfactants include, but are not limited to surfactant protein A, surfactant protein B, surfactant protein C, surfactant protein D, and mixtures and combinations thereof. Commercially available surfactants include, but are not limited to, KL-4, SURVANTA®, bovine lipid extract surfactant (BLES), INFASURF® (CALFACTANT®), CUROSURF®, HL-10, AEROSURF®, SUBOXONE®, ALVEOFACT®, SURFAXIN®, VENTICUTE®, PUMACTANT®/ALEC, and EXOSURF®.

In some embodiments of all aspects of the therapeutic methods described, administration of one or more other standard therapeutic agents can be combined with the administration of the enriched c-kit positive LSCs to treat the respiratory disorders or conditions, e.g., asthma, RDS or COPD, including the use of anticholinergic agents, β-2-adrenoreceptor agonists, such as formoterol or salmeterol, corticosteroids, antibiotics, anti-oxidation, antihypertension agents, nitric oxide, caffeine, dexamethasome, and IL-10 or other cytokines. In some embodiments, the included standard therapeutic agents are use for treating the symptoms of the lung disease. Table 1 shows some of the standard medical therapy for the some lung diseases.

For example, the use of c-kit positive LSCs in the methods described herein to treat, ameliorate or slow the progression of a condition such as CF can be optionally combined with other suitable treatments or therapeutic agents. For CF, this includes, but is not limited to, oral or aerosol corticosteroid treatment, ibuprofen treatment, DNAse or IL-10 treatment, diet control, e.g., vitamin E supplementation, vaccination against pathogens, e.g., *Haemophilus influenzae*, chest physical therapy, e.g., chest drainage or percussion, or any combination therein.

In some embodiments of all aspects of the therapeutic methods described, the standard therapeutic agents are those that have been described in detail, see, e.g., Harrison's Principles of Internal Medicine, 15.sup.th edition, 2001, E. Braunwald, et al., editors, McGraw-Hill, New York, N.Y., ISBN 0-07-007272-8, especially chapters 252-265 at pages 1456-1526; Physicians Desk Reference 54.sup.th edition, 2000, pages 303-3251, ISBN 1-56363-330-2, Medical Economics Co., Inc., Montvale, N.J. Treatment of any of lung disease, respiratory or pulmonary condition can be accomplished using the treatment regimens described herein. For chronic conditions, intermittent dosing can be used to reduce the frequency of treatment. Intermittent dosing protocols are as described herein.

For the clinical use of the methods described herein, isolated or enriched populations of enriched c-kit positive LSCs described herein can be administered along with any pharmaceutically acceptable compound, material, carrier or composition which results in an effective treatment in the subject. Thus, a pharmaceutical formulation for use in the methods described herein can contain an isolated or enriched population of c-kit positive LSCs in combination with one or more pharmaceutically acceptable ingredients.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent, media (e.g., stem cell media), encapsulating material, manufacturing aid (e.g., lubricant, talc magnesium, calcium or zinc stearate, or steric acid), or solvent encapsulating material, involved in maintaining the activity of, carrying, or transporting the isolated or enriched populations of LSCs from one organ, or portion of the body, to another organ, or portion of the body.

Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) phosphate buffered solutions; (3) pyrogen-free water; (4) isotonic saline; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) cellulose, and its derivatives, such as sodium carboxymethyl cellulose, methylcellulose, ethyl cellulose, microcrystalline cellulose and cellulose acetate; (17) powdered tragacanth; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) C2-C12 alchols, such as ethanol; (25) starches, such as corn starch and potato starch; and (26) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

DEFINITIONS

Unless otherwise defined, all technical and scientific terms used herein have the same meaning as commonly understood by one of ordinary skill in the art to which this invention belongs. Certain terms employed herein, in the specification, examples and claims are collected here.

As used herein, in vivo (Latin for "within the living") refers to those methods using a whole, living organism, such as a human subject. As used herein, "ex vivo" (Latin: out of the living) refers to those methods that are performed outside the body of a subject, and refers to those procedures in which an organ, cells, or tissue are taken from a living subject for a procedure, e.g., isolating c-kit positive LSCs from a lung tissue obtained from a donor subject, and then administering the isolated c-kit positive LSCs sample to a recipient subject. As used herein, "in vitro" refers to those methods performed outside of a subject, such as an in vitro cell culture experiment. For example, isolated c-kit positive LSCs can be cultured in vitro to expand or increase the number of c-kit positive LSCs, or to direct differentiation of the LSCs to a specific lineage or cell type, e.g., respiratory epithelial cells, prior to being used or administered according to the methods described herein.

The term "pluripotent" as used herein refers to a cell with the capacity, under different conditions, to commit to one or more specific cell type lineage and differentiate to more than one differentiated cell type of the committed lineage, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g., iPS cells as that term is defined herein) also have the characteristic of the capacity of extended passaging without loss of growth potential, relative to primary cell parents, which generally have capacity for only a limited number of divisions in culture.

The term "progenitor" cell are used herein refers to cells that have a cellular phenotype that is more primitive (i.e., is at an earlier step along a developmental pathway or progression than is a fully differentiated or terminally differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate. Progenitor cells give rise to precursor cells of specific determine lineage, for example, certain lung progenitor cells divide to give pulmonary epithelial lineage precursor cells. These precursor cells divide and give rise to many cells that terminally differentiate to pulmonary epithelial cells.

The term "precursor" cell are used herein refers to cells that have a cellular phenotype that is more primitive than a terminally differentiated cell but is less primitive than a stem cell or progenitor cells that is along its same developmental pathway. A "precursor" cell is typically progeny cells of a "progenitor" cell which are some of the daughter of "stem cells". One of the daughters in a typical asymmetrical cell division assumes the role of the stem cell.

The term "embryonic stem cell" is used to refer to the pluripotent stem cells of the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235, 970). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" is used to refer to any multipotent stem cell derived from non-embryonic tissue, including fetal, juvenile, and adult tissue. In some embodiments, adult stem cells can be of non-fetal origin. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells. As indicated above, stem cells have been found resident in virtually every tissue. Accordingly, the present invention appreciates that stem cell populations can be isolated from virtually any animal tissue.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as a lung stem cell), which in turn can differentiate into other types of precursor cells further down the pathway (such as a thymocyte, or a T lymphocyte precursor), and then to an end-stage differentiated cell, which plays a characteristic role in a certain tissue type, and may or may not retain the capacity to proliferate further.

The term "differentiated cell" is meant any primary cell that is not, in its native form, pluripotent as that term is defined herein. Stated another way, the term "differentiated cell" refers to a cell of a more specialized cell type derived from a cell of a less specialized cell type (e.g., a stem cell such as a lung stem cell) in a cellular differentiation process. Without wishing to be limited to theory, a pluripotent stem cell in the course of normal ontogeny can differentiate first to an endothelial cell that is capable of forming hematopoietic stem cells and other cell types. Further differentiation of a lung stem cell leads to the formation of the various pulmonary cell types, including pneumocyte type I and II cell types, endothelial cell types, smooth muscle, and epithelial cells.

As used herein, the term "somatic cell" refers to are any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell", by which is meant a somatic cell that is not present in or obtained from an embryo and does not result from proliferation of such a cell in vitro. In some embodiments the somatic cell is an "adult somatic cell", by which is meant a cell that is present in or obtained from an organism other than an embryo or a fetus or results from proliferation of such a cell in vitro.

As used herein, the term "adult cell" refers to a cell found throughout the body after embryonic development.

The term "phenotype" refers to one or a number of total biological characteristics that define the cell or organism under a particular set of environmental conditions and factors, regardless of the actual genotype. For example, the expression of cell surface markers in a cell.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The terms "renewal" or "self-renewal" or "proliferation" are used interchangeably herein, are used to refer to the ability of stem cells to renew themselves by dividing into the same non-specialized cell type over long periods, and/or many months to years.

In some instances, "proliferation" refers to the expansion of cells by the repeated division of single cells into two identical daughter cells.

The term "lineages" is used herein describes a cell with a common ancestry or cells with a common developmental fate.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "tissue" refers to a group or layer of specialized cells which together perform certain special functions. The term "tissue-specific" refers to a source of cells from a specific tissue.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" typically means a decrease by at least about 5%-10% as compared to a reference level, for example a decrease by at least about 20%, or at least about 30%, or at least about 40%, or at least about 50%, or at least about 60%, or at least about 70%, or at least about 80%, or at least about 90% decrease (i.e., absent level as compared to a reference sample), or any decrease between 10-90% as compared to a reference level. In the context of treatment or prevention, the reference level is a symptom level of a subject in the absence of administering a population of c-kit positive LSCs.

The terms "increased", "increase" or "enhance" are all used herein to generally mean an increase by a statically significant amount; for the avoidance of any doubt, the terms "increased", "increase" or "enhance" means an increase of at least 10% as compared to a reference level, for example an increase of at least about 20%, or at least about 30%, or at least about 40%, or at least about 50%, or at least about 60%, or at least about 70%, or at least about 80%, or at least about 90% increase or more or any increase between 10-90% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of c-kit positive LSCs expansion in vitro, the reference level is the initial number of r-kit positive LSCs isolated from the lung tissue sample.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

The term "consisting of" refers to compositions, methods, and respective components thereof as described herein, which are exclusive of any element not recited in that description of the embodiment.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005) and Animal Cell Culture Methods (Methods in Cell Biology, Vol. 57, Jennie P. Mather and David Barnes editors, Academic Press, 1st edition, 1998) which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean ±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

In some embodiments, the present invention can be defined in any of the following alphabetized paragraphs:

[A] A pharmaceutical composition comprising an isolated population of cells from a human lung tissue, the isolated population of cells is enriched for c-kit positive lung stem cells and is negative for at least one marker of the hematopoietic lineage, mast cell lineage, mesenchymal stromal cell lineage, epithelial lineage and/or endothelial cell lineage, and a pharmaceutical acceptable carrier.

[B] The pharmaceutical composition of paragraph [A], wherein the lung tissue is from an adult.

[C] The pharmaceutical composition of any one of paragraphs [A]-[B], wherein the at least one marker of a hematopoietic lineage is selected from the group consisting of CD34, CD45, and CD133.

[D] The pharmaceutical composition of any one of paragraphs [A]-[C], wherein the at least one marker of a mast cell lineage is selected from the group consisting of CD6, CD29, CD49d, CD49e, CD45 and tryptase.

[E] The pharmaceutical composition of any one of paragraphs [A]-[D], wherein the at least one marker of a mesenchymal stromal cell lineage is selected from the group consisting of CD44, CD90 and CD105.

[F] The pharmaceutical composition of any one of paragraphs [A]-[E], wherein the at least one marker of an epithelial cell lineage is selected from the group consisting of TTF1, p63, pan-cytokeratin, cytokeratin 5, CC10, aquaporin-5 and SPC.

[G] The pharmaceutical composition of any one of paragraphs [A]-[F], wherein the at least one marker of an endothelial cell and smooth muscle lineages is selected from the group consisting of Est1, vWF1, GATA 6, and alpha-SMA.

[H] The pharmaceutical composition of any one of paragraphs [A]-[G], wherein the c-kit cells are further negative for CD2, CD3, CD8, CD14, CD16, CD19, CD20, CD24, CD66b, and glycophorin A.

[I] The pharmaceutical composition of any one of paragraphs [A]-[H], wherein the c-kit cells are further expanded ex vivo.

[J] A method of preparing an isolated population of cells enriched for c-kit positive lung stem cells, the method comprising: obtaining human lung tissue from a subject; selecting c-kit positive cells from the human lung tissue; and proliferating said cells in a culture medium.

[K] A method of proliferating an isolated population of cells enriched for c-kit positive lung stem cells, the method comprising: selecting at least one c-kit positive cell from a human lung tissue sample; introducing said at least one selected cell to a culture medium; and proliferating said at least one selected cell in the culture medium.

[L] A method for treating or preventing a lung disorder in a subject in need thereof, comprising: obtaining a human lung tissue from a subject; extracting a population of c-kit positive lung stem cells from said lung tissue; expanding said population of c-kit positive lung stem cells; and administering said the expanded population of c-kit positive stem cells to the subject.

[M] The method of any one of paragraphs PHU, wherein the population of c-kit positive lung stem cells is further negative for at least one marker of the hematopoietic lineage, mast cell lineage, mesenchymal stromal cell lineage, epithelial lineage and/or smooth muscle and endothelial cell lineage

[N] The method of any one of paragraphs [J]-[M], wherein the human lung tissue is an adult lung tissue.

[O] The method of any one of paragraphs [J]-[N], wherein the human lung tissue is cryopreserved prior to selecting or extracting c-kit positive cells.

[P] The method of any one of paragraphs [J]-[O], wherein the selecting or extracting of c-kit positive cells is performed using an antibody against c-kit.

[Q] The method of any of one paragraphs [J]-[P], further comprising negative selection for at least one marker of the hematopoietic lineage, mast cell lineage, mesenchymal stromal cell lineage, epithelial lineage and/or endothelial cell lineage cells.

[R] The method of any paragraphs [J]-[Q], wherein the selecting is by flow cytometry.

[S] The method of any paragraphs [J]-[Q], wherein the selecting is by immunomagnetic selection with c-kit antibodies conjugated to beads.

[T] The method of any of one paragraphs [J]-[S], further comprising cyropreserving the c-kit positive lung cells.

[U] The method of any one of paragraphs [M]-[T], further comprising administering at least one therapeutic agent.

[V] The method of any one of paragraphs [M]-[U], wherein the population of c-kit positive lung stem cells repairs, reconstitutes and/or generates pulmonary epithelium, pulmonary vasculature/pulmonary endothelium and/or pulmonary alveoli.

[W] The method of any one of paragraphs [M]-[V], further comprising selecting a subject who is suffering from a lung disorder prior to administering the population enriched for c-kit positive lung stem cells.

[X] The method of any one of paragraphs [M]-[W], further comprising selecting a subject in need of restoring the structural and functional integrity of a damaged lung prior to administering the cells.

[Y] The method of any one of paragraphs [M]-[X], further comprising selecting a subject in need of treatment, prevention or repair or reconstitution or generation of pulmonary vasculature or pulmonary epithelium, pulmonary endothelium, or pulmonary alveoli prior to administering the cells.

[Z] The method of any one of paragraphs [M]-[Y], wherein the administration is intrapulmonary administration, systemic administration, or a combination thereof.

[AA] The method of paragraph [Z], wherein the intrapulmonary administration is intratracheal or intranasal administration.

[BB] A composition for use in treating and/or preventing a lung disease in a subject, the composition comprising an enriched population of isolated c-kit positive lung stem cells from a human lung tissue sample wherein the c-kit positive lung stem cells are negative for at least one marker of the hematopoietic lineage, mast cell lineage, mesenchymal stromal cell lineage, epithelial lineage and/or endothelial cell lineage.

[CC] The composition of paragraph [BB], wherein the lung tissue is from an adult.

[DD] The composition of paragraph [BB] or [CC], wherein the at least one marker of a hematopoietic lineage is selected from the group consisting of CD34, CD45, and CD133.

[EE] The composition of any one of paragraphs [BB]-[DD], wherein the at least one marker of a mast cell lineage is selected from the group consisting of CD6, CD29, CD49d, CD49e, CD45 and tryptase.

[FF] The composition of any one of paragraphs [BB]-[EE], wherein the at least one marker of a mesenchymal stromal cell lineage is selected from the group consisting of CD44, CD90 and CD105.

[GG] The composition of any one of paragraphs [BB]-[FF], wherein the at least one marker of an epithelial cell lineage is selected from the group consisting of TTF1, p63, pan-cytokeratin, cytokeratin 5, CC10, aquaporin-5 and SPC.

[HH] The composition of any one of paragraphs [BB]-[GG], wherein the at least one marker of an endothelial cell and smooth muscle lineages is selected from the group consisting of Est1, vWF1, GATA 6, and alpha-SMA.

[II] The composition of any one of paragraphs [BB]-[HH], wherein the c-kit cells are further negative for CD2, CD3, CD8, CD14, CD16, CD19, CD20, CD24, CD66b, and glycophorin A.

[JJ] The composition of any one of paragraphs [BB]-[II], wherein the c-kit cells are further expanded ex vivo.

[KK] A method for treating or preventing a lung disorder in a subject in need thereof, comprising administering a pharmaceutical composition of any one of paragraphs [A]-[I].

[LL] A method for treating or preventing a lung disorder in a subject in need thereof, comprising administering a composition of any one of paragraphs [BB]-[JJ].

[MM] The method of paragraph [KK] or [LL], further comprising administering at least one therapeutic agent.

[NN] The method of any one of paragraphs [KK]-[MM], wherein the population of c-kit positive lung stem cells repairs, reconstitutes and/or generates pulmonary epithelium, pulmonary vasculature/pulmonary endothelium and/or pulmonary alveoli.

[OO] The method of any one of paragraphs [KK]-[NN] further comprising selecting a subject who is suffering from a lung disorder prior to administering the population enriched for c-kit positive lung stem cells.

[PP] The method of any one of paragraphs [KK]-[QQ] further comprising selecting a subject in need of restoring the structural and functional integrity of a damaged lung prior to administering the cells.

[QQ] The method of any one of paragraphs [KK]-[PP] further comprising selecting a subject in need of treatment, prevention or repair or reconstitution or generation of pulmonary vasculature or pulmonary epithelium, pulmonary endothelium, or pulmonary alveoli prior to administering the cells.

[RR] The method of any one of paragraphs [KK]-[QQ], wherein the administration is intrapulmonary administration, systemic administration, or a combination thereof.

[SS] The method of paragraph [RR], wherein the intrapulmonary administration is intratracheal or intranasal administration.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein, different culture medium and supplements can be used to culture expand the isolated cells. One skilled in the art would be able to perform tests to evaluate the choice of culture medium and supplements. Such equivalents are intended to be encompassed by the following claims.

The references cited herein and throughout the specification are incorporated herein by reference.

EXAMPLE

The fundamental properties of stem cells are self-renewal, clonogenicity and multipotentiality in vitro and in vivo. The lack of this biological behavior raises questions on the appropriateness of the claim made on the identification and physiological role of tissue specific stem cells (1, 2), a limitation that is particularly apparent in the mammalian lung (3). Different cell populations with some of these features have been described in distinct anatomical regions of the lung (3-5), but the unambiguous demonstration of a non-committed cell in the absence of specialized functions remains elusive. Clara cells distributed in the tracheal epithelium, partly in the bronchioles in the mouse and in the small airways in humans can divide and contribute to the development and repair of proximal and more distal respiratory structures (6). However, these elements are insufficient to justify their inclusion in stem cell classes. Additionally, Clara cells secrete mucin that per se defeats the undifferentiated phenotype typical of stem cells. Similarly, the bronchioalveolar stem cells (BASCs) form in vitro small colonies and express molecular markers of Clara cells and epithelial cells (7), and whether these growth characteristics are operative in vivo has not been shown (3). Recently, the ability of BASCs to participate in lung growth and regeneration has been challenged (8). Type II alveolar epithelial cells divide and differentiate not only in type II but also in type I alveolar pneumocytes. Based on this growth potential, type II cells have been considered progenitors of the alveolar epithelium (9). Side population cells have been found but their differentiation mimics mesenchymal stromal cells (10). Basal epithelial cells have been considered as "stem cells" capable of giving rise to epithelial cell lineages (Rock et al. Proc. Natl. Acad. Sci. U.S.A. 2009, 106:12771-5). However, these cells express various epithelial markers, including p63 and cytokeratin 5, and, therefore, correspond to a category of early committed cells which derives from a more undifferentiated stem cell pool, such as c-kit-positive hLSCs.

To establish whether the human lung possesses a stem cell compartment, the inventors have employed the stem cell antigen c-kit as a marker for the identification and characterization of pulmonary primitive cells. The c-kit epitope is present in hematopoietic and cardiac stem cells (11-13) and was used to help uncover a pool of human lung stem cells (hLSCs) which are analogy to stem cells in the bone marrow and the heart are self-renewing, clonogenic and multipotent. If cells lack this growth behavior and acquire only the epithelial lineage or create exclusively endothelial cells (ECs) and smooth muscle cells (SMCs) in vitro, the de novo formation of pulmonary structures in vivo by this cell category would not be achievable. For actual tissue repair, hLSCs have to generate bronchioles, alveoli and vessels which are integrated structurally and functionally with the airways and vasculature of the recipient organ. Importantly, lung regeneration has to occur independently from cell fusion; heterokaryons divide poorly and have at most a transient positive effect on the age of the fused cells (14).

Materials and Methods

Human Lungs

A total of nine human lungs were studied. Samples were fixed in formalin and embedded in paraffin. These specimens were used to identify putative stem cell niches and the pattern of division of replicating human lung stem cells (hLSCs). The localization of these primitive cells in the distal airway was determined by immunolabeling with antibodies against the stem cell antigen c-kit (33-36). Epithelial cells were labeled by pan-cytokeratin (CK) and surfactant protein C(SPC). Endothelial cells (ECs) and vascular and non-vascular smooth muscle cells (SMCs) were detected with anti-von Willebrand factor (vWf) and anti-α-SM actin (α-SMA) antibody, respectively. Fibroblasts were identified by procollagen. Adherens junctions between hLSCs and epithelial cells, SMCs and fibroblasts were defined by the expression of E-cadherin (E-cadh). The presence of mast cells was assessed by the surface antigen CD45 and the hydrolytic enzyme tryptase (33-36).

hLSCs

Discarded human lung tissue specimens were obtained from 8 patients who underwent thoracic surgery and partial or completed resection of the lung. There was no knowledge concerning sex and age of the patients, type of the lung disease and duration of the disease. Additionally, the inventors had no information concerning the specific origin of these samples. The size of the specimens varied from 1-2 $cm^3$. For the isolation of hLSCs, fragments were enzymatically dissociated employing a protocol developed in the inventors' laboratory for the collection and expansion of human cardiac stem cells (35, 36). Tissue fragments were enzymatically dissociated in a solution containing collagenase to obtain a single cell suspension. Cells were sorted with magnetic immunobeads for c-kit (Miltenyi) and after sorting, cell phenotype was defined by immunocytochemistry (33-36). Putative hLSCs were then cultured in F12 medium (Gibco) supplemented with 5-10% FBS (Gibco) and insulin-selenium-transferrin mixture (Sigma). At P2-P3, cells were characterized by FACS and immunolabeling to detect lineage negative hLSCs (35, 36). In both cases, cells were fixed in 4% paraformaldehyde for 15 min at room temperature and tested for markers of hematopoietic cell lineages, mesenchymal stromal cells, mast cells and transcription factors and cytoplasmic proteins typical of pulmonary cell classes. For immunocytochemistry, when possible, primary antibodies were directly labeled with fluorochromes (Molecular Probes) to avoid cross-reactivity (35-38).

Cloning Assay and Clonogenic Cell Differentiation

Sorted lineage negative c-kit-positive cells were plated at limiting dilution, one cell per 20 mm$^2$ and allowed to form individual colonies. About 3-4 weeks later, clones of identical cells were obtained (33-36). Clones were collected utilizing cloning cylinders and expanded in F12 medium (35, 36). Differentiation of clonogenic cells was induced by MEM containing 10% FBS and 10-8 M dexamethasone (33-36). Cell phenotypes were defined by FACS analysis and immunocytochemistry.

hLSC Division

Symmetric and asymmetric division (35, 36, 39) of hLSCs was determined by immunolabeling mitotic cells with α-adaptin antibody. Mitotic chromosomes were identified by staining with propidium iodide. To establish the fate of daughter cells, antibodies for markers of lung lineage commitment were employed: anti-TTF1 (for epithelial lineage), anti-Ets1 (for endothelial lineage) and anti-GATA6 (for muscle lineage).

Lentiviral Infection hLSCs were infected with a lentivirus carrying EGFP in the presence of 8 μg/ml polybrene (32, 35, 36). After overnight incubation at 37° C., fresh medium was added. Five days later, the efficiency of infection was established by measuring the fraction of hLSCs showing native EGFP fluorescence. Efficiency of infection was 80±5 (n=7).

Lung Injury and Regeneration

Under ketamine (120 mg/kg bw) and xylazine (0.5 mg/kg bw) anesthesia (35, 37), C57Bl/6 female mice immunosuppressed with cyclosporine A (5 mg/kg/day) were mechanically ventilated and a cryoinjury, ~2-3 mm$^3$ in volume, was induced in the left lung with a stainless steel probe pre-cooled in liquid nitrogen. The area of damage was identified by pale color of the affected tissue. Shortly thereafter, six injections of clonogenic or non-clonogenic hLSCs, previously infected with a lentivirus carrying EGFP (35, 36, 38), were made in the region adjacent to the damaged parenchyma. Each injection consisted of ~20,000 cells mixed with 1% rhodamine-labeled polystyrene microspheres. This protocol allowed the direct visualization of the site of injection and the accuracy of cell delivery (33-38). Animals were sacrificed at 12 hours, 2 days or 10 days following surgery by intraperitoneal administration of sodium pentobarbital, 75 mg/kg bw. The lung was perfused through the trachea first with PBS for 1 minute and then with 10% phosphate-buffered formalin for 15 minutes (40). Throughout the procedure, the perfusion pressure was kept at 20 mmHg. Subsequently, the lung was excised, immersed in formalin for 24 hours and embedded in paraffin.

Serial Transplantation of hLSCs

Ten-fourteen days after cryoinjury and hLSC implantation, regenerated lungs were excised and subjected to enzymatic digestion to obtain a single cell suspension. EGFP-positive c-kit-positive hLSCs were sorted by FACS and injected immediately in new recipient immunosuppressed mice following a protocol identical to that described above. Animals were sacrificed ten days later; the lung was excised, immersed in formalin for 24 hours, and embedded in paraffin.

Immunohistochemistry and In Situ Hybridization

Antibodies were used to detect human pulmonary structures within the recipient mouse lung. Human cells were detected by EGFP localization and by in situ hybridization with a probe against the human-specific Alu repeat sequences (35, 36). Human X-chromosome and mouse X-chromosome were also identified (35, 36). Images were assembled with Adobe Photoshop 7.0 software according to the standard protocol detailed in the Nature guidelines for digital images. Processing included the assignment of pseudo-colors and changes in brightness. It was applied uniformly across the entire image and was used exclusively to equalize the appearance of multiple panels in a single figure.

Spectral Analysis

This methodology was performed with a Zeiss LSM510 Meta confocal microscope (Zeiss) utilizing the meta detector and the lambda acquisition mode. Lung sections were stained with DAPI only and the native fluorescence of EGFP was examined. Formalin-fixed tissue exhibits some auto-fluorescence due to cross-linking of proteins by the aldehyde groups of the fixative. The spectral properties of EGFP and formalin cross-linked cellular proteins are different. Intrinsic EGFP fluorescence was excited at 488 nm with an argon laser and its fluorescence intensity was recorded generating a lambda stack ranging from 492 to 748 nm at 10.7 nm intervals. The lens and corresponding numerical aperture were 60× and 1.4, respectively. For each region of interest, a graph plotting mean pixel intensity and the emission wavelength of the lambda stack was generated. To compare the shape of each curve obtained from EGFP-positive and EGFP-negative structures, the values of emission spectra were normalized by dividing the intensity of each wavelength by the peak signal. The spectrum obtained from EGFP-positive cells exhibited a major peak at ~525 nm, with a smaller peak at ~560 nm. In contrast, the spectrum of autofluorescence was more uniformly spread across the range of wavelengths and did not show a clearly defined peak of emission (32, 42-44). In an identical manner, the inventors analyzed immunolabeled EGFP-positive structures, including epithelial cells and SMCs.

Two-Photon Microscopy

Ten days after lung cryoinjury and implantation of EGFP-positive clonogenic or non-clonogenic hLSCs, the lungs together with the trachea and the heart were excised. The preparation was placed in a bath mounted on the stage of a two-photon microscope (Bio-Rad Radiance 2100 MP). Subsequently, the lungs were continuously perfused at a pressure of 20 mmHg through the trachea or pulmonary artery with PBS containing rhodamine-labeled dextran, which has a MW of 70 kDa and red fluorescence. This molecule does not cross the endothelial or epithelial barrier, allowing the visualization of the pulmonary vasculature or the respiratory tree, respectively. Rhodamine is covalently bound to dextran and has inherent red fluorescence so that these two distinct pulmonary compartments could be detected by two-photon microscopy. Mouse recipient pulmonary structures were by necessity EGFP-negative while the regenerated distal airway and vessels were EGFP-positive, constituting the progeny of the injected hLSCs.

All experiments were performed at 37° C. The microscope was positioned to view the area of injury and the adjacent parenchyma. EGFP and rhodamine were excited at 900 nm with mode-locked Ti:Sapphire femtosecond laser (Tsunami, Spectra-Physics) and the corresponding images were acquired at emission wavelengths of 525 and 600 nm, respectively. Collagen was visualized by second harmonic generation, which is the product of two-photon excitation and periodic structure of collagen. Thus, the red fluorescence of rhodamine-labeled dextran, the green fluorescence of EGFP, and the blue fluorescence of collagen were detected directly in the injured lung.

When the trachea was perfused with rhodamine-labeled dextran, the newly-formed airway structures were both EGFP-positive and rhodamine-positive. However, with this approach, the regenerated pulmonary vasculature was EGFP-positive and rhodamine-negative. Conversely, when the pulmonary artery was perfused with rhodamine-labeled dextran, the newly-formed vessels were both EGFP-positive and rhodamine-positive while the regenerated airways were EGFP-positive and rhodamine-negative.

Quantitative RT-PCR

Total RNA was extracted with TRIzol from clonal hLSCs for the detection of transcripts for c-kit, the stemness genes Oct3/4, Nanog, Sox2 and Klf4, and epithelial lineage genes. CD34 human bone marrow cells and Kazumi lymphoma cells were used as positive controls for c-kit expression. Additionally, RNA was obtained from the mouse lung 1-2 weeks after cryoinjury and injection of clonal and non-clonal hLSCs. cDNA was generated from 2 µg of total RNA incubated with oligo(dT)15 primer for 2 hours at 37° C. RT-PCR was performed on 7300 Real Time PCR Systems (Applied Biosystems) using ½oth of the cDNA per reaction (45-47). Cycling conditions were as follows: 95° C. for 10 minutes followed by 35 cycles of amplification (95° C. denaturation for 15 seconds, and 60° C. combined annealing/extension for 1 minute). Human-specific primers (see below) were designed with the Vector NTI software (INVITROGEN™). Quantified values were normalized against the input determined by the housekeeping human gene 132 microglobulin. Human lung total RNA (Applied Biosystems) and RNA extracted from an untreated mouse lung were used as positive and negative controls, respectively.

PCR products were run on 2% agarose/1×TBE gel and DNA bands with the expected molecular size were obtained. DNA was extracted with QIAquick Gel Extraction Kit (Qiagen), eluted in 30 µl of 10 mM Tris buffer (pH 8.5) and amplified by Platinum Blue PCR Supermix in the presence of the same forward and reverse primers used for real-time RT-PCR. PCR reaction was carried out in an Eppendorf Mastercycler (45-47). Cycling conditions were as follows: 94° C. for 2 minutes, followed by 20 cycles of amplification (94° C. denaturation for 15 seconds, 60° C. annealing for 30 seconds, 72° C. elongation for 15 seconds) with a final incubation at 72° C. for 2 minutes. After purification using QIAquick PCR Purification kit, samples were submitted to the DNA Sequencing Facility at Dana-Farber/Harvard Cancer Center to obtain the DNA sequence. The human origin of the transcripts was confirmed by employing BLAST searches. The following are the qRT-PCR primers for the respective genes analyzed:

```
Mouse ACTB (β-actin; amplicon size: 126 bp)
[cross-react with Human]
Forward:
                                           (SEQ. ID. No: 1)
5'- AGAAGGAGATTACTGCTCTGGCTC -3'

Reverse:
                                           (SEQ. ID. No: 2)
5'- ACATCTGCTGGAAGGTGGACA -3'

B2M (β2 microglobulin; amplicon size: 176 bp)
Forward:
                                           (SEQ. ID. No: 3)
5'- CAAGGACTGGTCTTTCTATCTCTTG -3'

Reverse:
                                           (SEQ. ID. No: 4)
5'- ATTCATCCAATCCAAATGCG -3' c-kit (amplicon size: 146 bp)
Forward:
                                           (SEQ. ID. No: 5)
5'- GCACCTGCTGAAATGTATGACATAAT -3'

Reverse:
                                           (SEQ. ID. No: 6)
5'- CTGCAGTTTGCTAAGTTGGAGTAAAT -3'

OCT3/4 (amplicon size: 165 bp)
Forward:
                                           (SEQ. ID. No: 7)
5'- AGGAGAAGCTGGAGCAAAA - 3'

Reverse:
                                           (SEQ. ID. No: 8)
5' - GGCTGAATACCTTCCCAAA - 3'

NANOG (amplicon size: 133 bp)
Forward:
                                           (SEQ. ID. No: 9)
5'- GGTCCCGGTCAAGAAACAGA - 3'

Reverse:
                                           (SEQ. ID. No: 10)
5' - GAGGTTCAGGATGTTGGAGA - 3'

SOX2 (amplicon size: 155 bp)
F:
                                           (SEQ. ID. No: 11)
CCAGCTCGCAGACCTACA R:
                                           (SEQ. ID. No: 12)
CCTGGAGTGGGAGGAAGA KLF4 (amplicon size: 144 bp)
Forward:
                                           (SEQ. ID. No: 13)
5' - GACTTCCCCCAGTGCTTC - 3'

Reverse:
                                           (SEQ. ID. No: 14)
5' - CGTTGAACTCCTCGGTCTC - 3'

TP63 (amplicon size: 185 bp)
Forward:
                                           (SEQ. ID. No: 15)
5'- AAAGCAGCAAGTTTCGGACAGTAC - 3'

Reverse:
                                           (SEQ. ID. No: 16)
5' - CCAGGGACTCTTTGATCTTCAACAG - 3'

KRT5 (cytokeratin 5; amplicon size: 162 bp)
Forward:
                                           (SEQ. ID. No: 17)
5'- AGGGCGAGGAATGCAGACTC - 3'

Reverse:
                                           (SEQ. ID. No: 18)
5' - TGCTACCTCCGGCAAGACCT - 3'

TTF1 (Nkx2-1; amplicon size: 116 bp)
Forward:
                                           (SEQ. ID. No: 19)
5'- CATGAGGAACAGCGCCTCTG -3'
```

-continued

Reverse:
5'- CGCCCATGCCGCTCATG -3'

SCGB1A1 (Clara cells 10 kDa secretory protein; amplicon size: 191 bp)
Forward:
(SEQ. ID. No: 20)
5'- TCACCCTCACCCTGGTCACA -3'

Reverse:
(SEQ. ID. No: 21)
5'- GGTGTCCACCAGCTTCTTCAGC -3'

SFTPC (surfactant protein C; amplicon size: 161 bp)
Forward:
(SEQ. ID. No: 22)
5'- CACTGGCCTCGTGGTGTATG -3'

Reverse:
(SEQ. ID. No: 23)
5'- CCTGCAGAGAGCATTCCATC -3'

CFTR (cystic fibrosis transmembrane conductance regulator; amplicon size: 159 bp)
Forward:
(SEQ. ID. No: 24)
5'- GAAGCAATGCTGGAATGCCAAC -3'

Reverse:
(SEQ. ID. No: 25)
5'- CTTGCTTGAGTTCCGGTGGG -3'

KRT18 (keratin 18; amplicon size: 164 bp)
Forward:
(SEQ. ID. No: 26)
5'- CTGGAAGATGGCGAGGACTTTAATC -3'

Reverse:
(SEQ. ID. No: 27)
5'- GGTACCCTGCTTCTGCTGG -3'

T1α (podoplanin; amplicon size: 175 bp)
Forward:
(SEQ. ID. No: 28)
5'- CAGTCCACGCGCAAGAACAAAG -3'

Reverse:
(SEQ. ID. No: 29)
5'- GCACCAATGAAGCCGATGGC -3'

AQP5 (aquaporin 5; amplicon size: 198 bp)
Forward:
(SEQ. ID. No: 30)
5'- GTCCATTGGCCTGTCTGTCACC -3'

Reverse:
(SEQ. ID. No: 31)
5'- GAGTTGGGGAAGAGCAGGTAGAAG -3'

ETS1 (v-ets erythroblastosis virus E26 oncogene homolog 1; amplicon size: 186 bp)
Forward:
(SEQ. ID. No: 32)
5'- GCTATCAAACAAGAAGTCGTCACC -3'

Reverse:
(SEQ. ID. No: 33)
5'- GAAGCTGTCATAGGAGGGAACA -3'

PECAM1 (CD31; amplicon size: 194 bp)
Forward:
(SEQ. ID. No: 34)
5'- TAAAGAGCCTCTGAACTCAGACG -3'

Reverse:
(SEQ. ID. No: 35)
5'- CATCTGGCCTTGCTGTCTAAG -3'

TGFBR1 (TGF βreceptor 1; amplicon size: 191 bp)
Forward:
(SEQ. ID. No: 36)
5'- CAAACCACAGAGTGGGAACA -3'

Reverse:
(SEQ. ID. No: 37)
5'- TACAAGATCATAATAAGGCAGTTGG -3'

Immunoprecipitation and Western Blotting

Protein lysates of hLSCs before and after exposure to dexamethasone were obtained using RIPA buffer (Sigma) and protease inhibitors. Equivalents of 20-50 µg of proteins were separated on 8-12% SDS-PAGE, transferred onto PVDF membranes (Bio-Rad) and subjected to Western blotting with Oct3/4 (rabbit polyclonal, Novus Biologicals), Nanog (rabbit polyclonal, Abnova), Sox2 (mouse monoclonal, Abcam), and Klf4 (mouse monoclonal, Abcam) antibodies diluted 1:100 in TBST overnight at 4° C. HRP-conjugated anti-IgG were used as secondary antibodies. Proteins were detected by chemiluminescence (SuperSignal West Femto Maximum Sensitivity Substrate, Thermo Scientific) and optical density was measured. Loading conditions were determined by the expression of GAPDH (Millipore) and/or by Ponceau S (Sigma) staining of the membrane after transfer (46-48).

For c-kit expression, 50-100 µg of proteins were immunoprecipitated with c-kit antibody (mouse monoclonal, Serotec) and subjected to Western blotting with c-kit antibody (rabbit polyclonal, Cell Signaling; #3074). CD34-positive bone marrow cells and Kazumi lymphoma cells were used as positive controls. The mature form of the c-kit receptor, capable of binding stem cell factor, corresponds to a 145 kDa band. The lower molecular weight form of c-kit at 120 kDa was also found.

Statistical Analysis

In all cases, results are presented as mean±SD. Statistical significance was determined by the analysis of variance and Bonferroni method or Student's t test; $P<0.05$ was considered significant.

Results hLSC Niches

Stem cells are stored in niches where they are connected to the supporting cells by gap and adherens junctions made by connexins and cadherins, respectively (15). It was found that the lower respiratory tract possessed structures with the characteristics of hLSC niches. They consisted of undifferentiated c-kit-positive cells together with early committed epithelial cells. E-cadherin was detected at the interface of putative hLSCs and epithelial cells, SMCs and fibroblasts (data not shown), indicating that these cells may function as supporting cells in the lung stem cell niches.

Bronchiolar profile composed of epithelial cells was positive for cytokeratin. Several c-kit-positive cells were present within the bronchiolar wall and its proximity. C-kit-positive cells were connected by E-cadherin to bronchiolar epithelial cells, smooth muscle cells (α-SMA), and fibroblasts (procollagen: procoll staining).

Progenitor cells retained the stem cell antigen c-kit and expressed the thyroid transcription factor-1 (TTF1) in the absence of specialized cytoplasmic proteins. TTF1 is the earliest marker of lung development and its deletion prevents the formation of lung parenchyma (16). Precursor cells positive for c-kit, TTF1 and surfactant protein C(SPC) or cytokeratin were also observed (data not shown). Importantly, the primitive and committed c-kit-positive cells were small and negative for CD45 and tryptase excluding their potential bone marrow origin and the mast cell phenotype (data not shown). These structural characteristics were documented in each of the nine human specimens examined histologically.

Human LSCs

Figure 2:
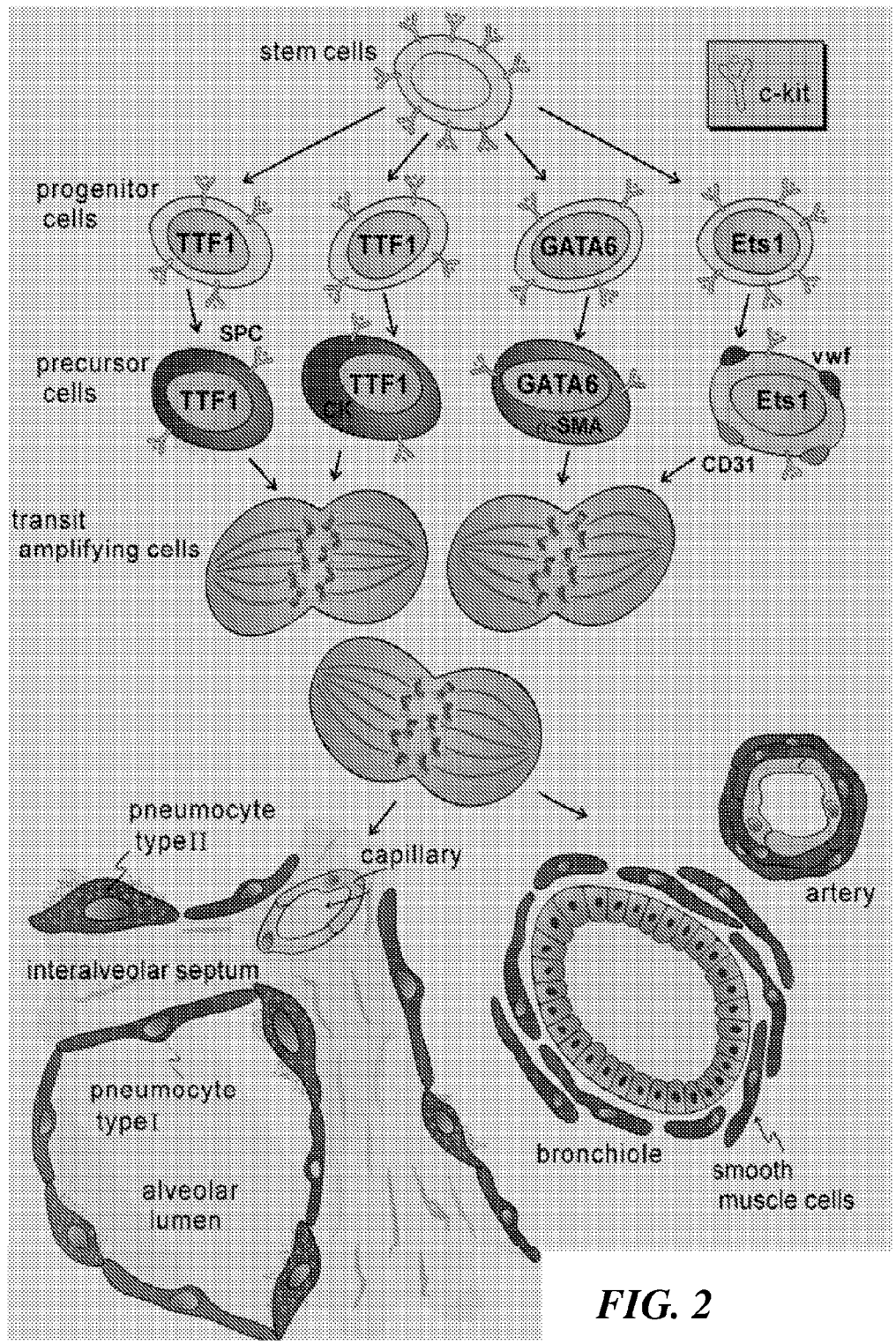
FIG. 2 is a schematic diagram showing the developmental pathway of a lung stem cell and the markers therein.

Based on these observations, lung samples discarded at surgery were digested enzymatically and putative hLSCs were collected by immunosorting for c-kit. After their expansion (data not shown), cells at P2-P3 were characterized by FACS analysis. C-kit-positive cells were negative for hematopoietic markers, including CD34, CD45, CD133 and a cocktail of antibodies against bone marrow-derived cells. The absence of CD45 and tryptase was consistent with the non-mast cell lineage of hLSCs. Additionally, putative hLSCs did not express CD44, CD90 and CD105, markers of mesenchymal stromal cells (FIG. 1A). These cells were also negative for transcription factor and cytoplasmic proteins of epithelial cells comprising TTF1, cytokeratin and SPC. Similarly, transcription factors and cytoplasmic proteins specific of ECs and SMCs were rarely found (data not shown). They included Ets1, von Willebrand factor (vWf), GATA6, and α-smooth muscle actin (α-SMA).

Figure 1C:
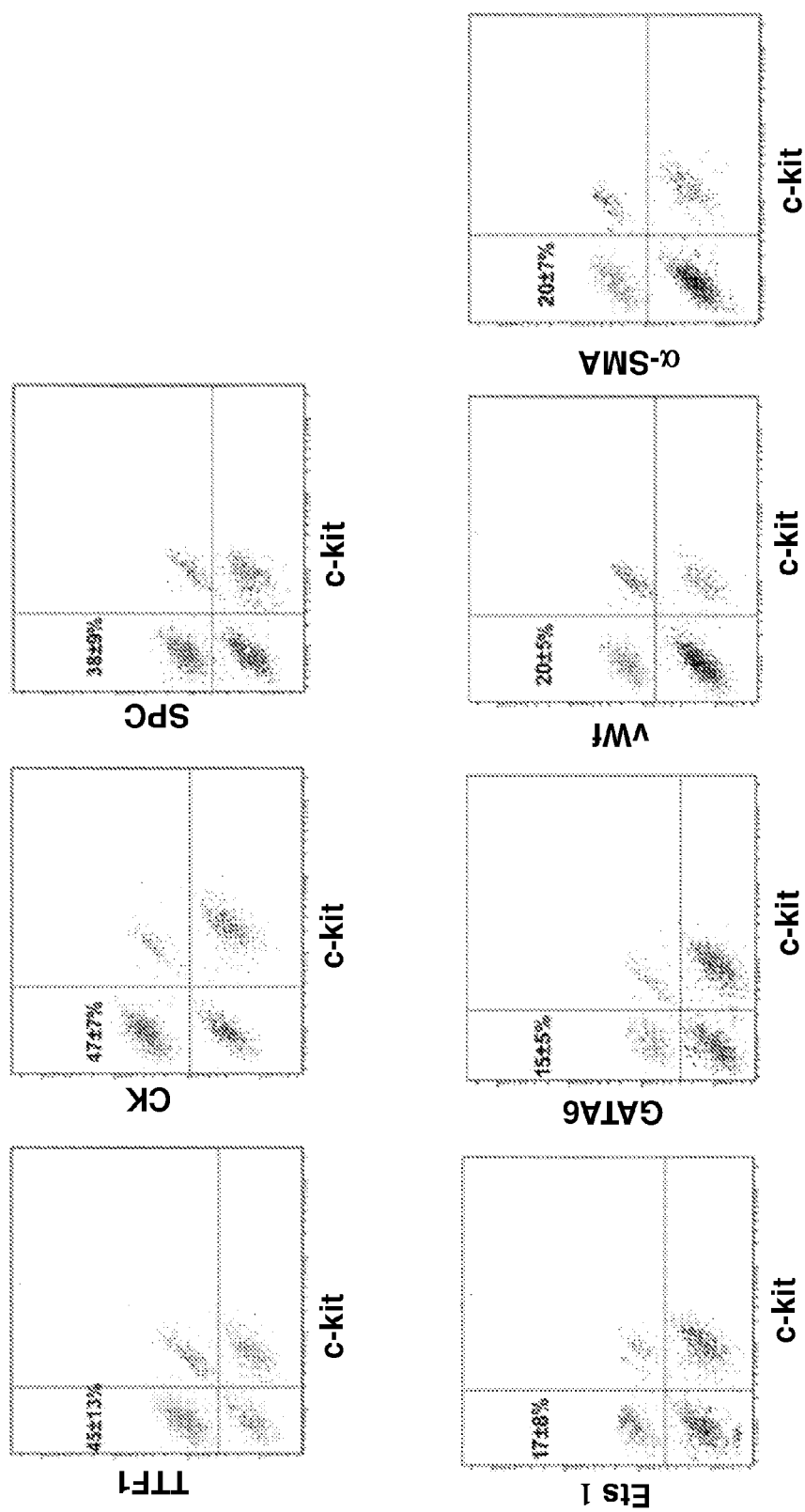
FIG. 1C are the fluorescent activated cell sorting data showing that the expression profile of dexamethasone induced differentiated clonogenic c-kit-positive lineage negative cells expressed markers of epithelial cell (TTF1, CK, SPC), ECs (Ets1, vWf) and SMCs (GATA6, α-SMA).
Figure 1D:
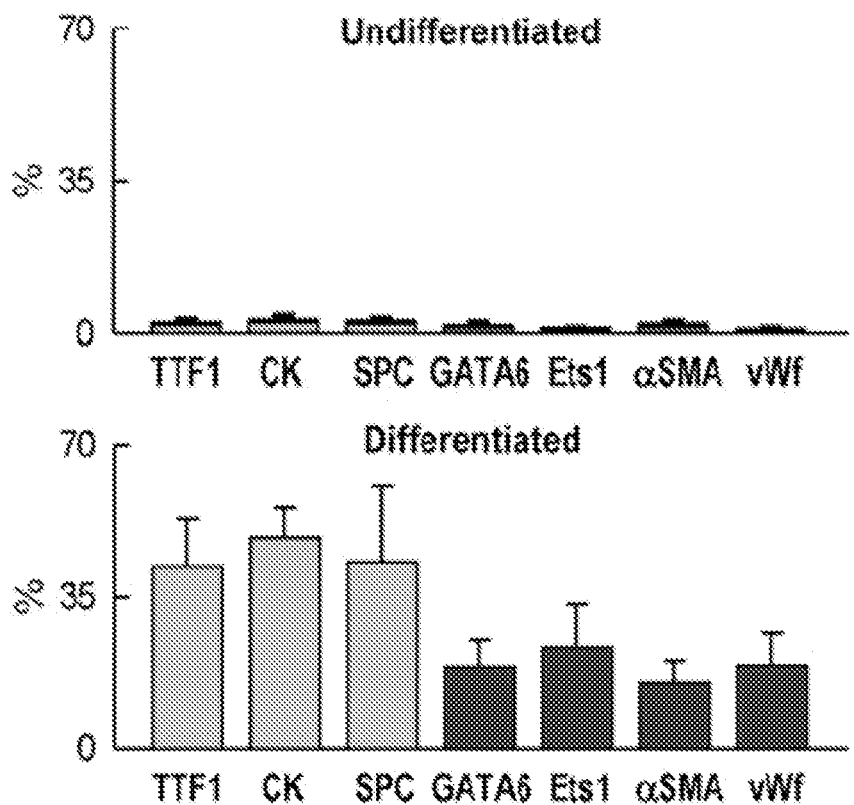
FIG. 1D shows the expression of markers specific for epithelial cells, endothelial cells and smooth muscle cells in undifferentiated and differentiated clonogenic c-kit positive cells after exposure to dexamethasone. Data are shown as mean±standard deviation (SD).
Figure 1D:
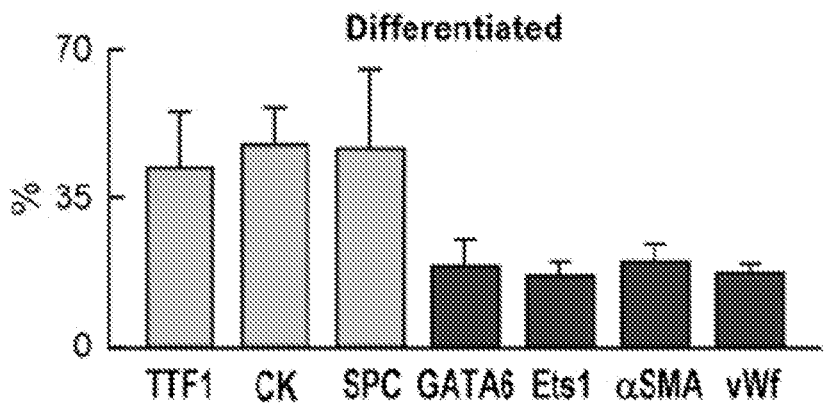

For clonal analysis, FACS-sorted c-kit-positive cells were plated at limiting dilution, 1 cell per 20 mm². After 3-4 weeks, multicellular clones were obtained; cells in the clones continued to express c-kit (data not shown). Clonal efficiency was 1.3±0.5% (N=4; ~40 clones per patient). Clonogenic hLSCs exposed to differentiating medium lost largely the c-kit epitope and expressed in a considerable manner the epithelial markers TTF1, cytokeratin and SPC. Smaller but significant fractions of cells expressed the vascular lineage proteins Ets1, GATA6, vWf and α-SMA (FIG. 1C). The commitment of hLSCs measured by FACS was complemented with the evaluation of cell differentiation by immunocytochemistry. Morphologically, progressive stages of epithelial and vascular cell differentiation were found in combination with mature cell phenotypes (data not shown). Both FACS and immunolabeling protocols provided comparable results (FIG. 1D). Collectively, these findings documented a lineage relationship between hLSCs and pulmonary cell progeny, pointing to a hierarchical model of organ growth.

Division of hLSCs

Stem cells divide symmetrically and asymmetrically. With symmetric division, two identical daughter cells are formed while with asymmetric division, two cells with different phenotype are generated. These patterns of growth are controlled by the distribution of the cell fate determinants Numb and α-adaptin (17). The uniform localization of these endocytic proteins at the two poles of the dividing stem cell leads to the generation of two cells with identical fate. In contrast, the localization of these proteins at one pole only of the dividing stem cell results in two cells with different destiny. Therefore, to define the growth behavior of hLSCs, these cells were cultured in growth medium and the partitioning of α-adaptin was established.

TTF1, GATA6 and Ets1 were employed as markers of cell commitment to distinguish the characteristics of the forming cells. hLSCs divided symmetrically and asymmetrically although symmetric division predominated. Asymmetric division of hLSCs gave rise to one daughter cell which expressed TTIF1, GATA6 or Ets1 while the other retained the stem cell phenotype. Conversely, symmetric division generated two lineage negative or positive daughter cells (data not shown).

Figure 3:
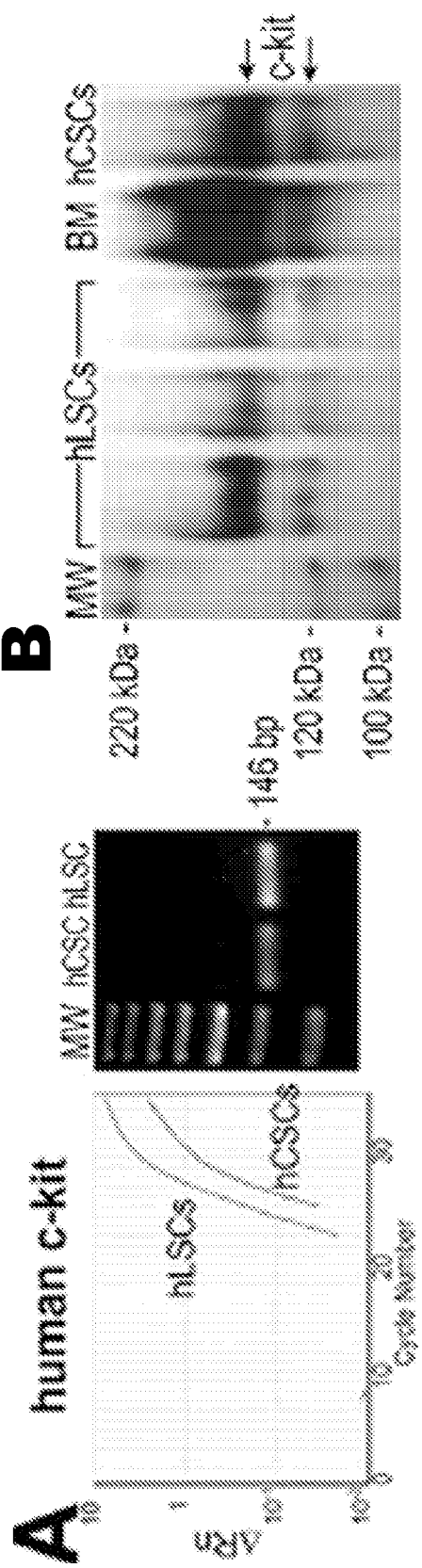
FIG. 3A shows the qRT-PCR of c-Kit in clonal hLSCs and hCSCs. The fragment of the mRNA of c-kit amplified in about 145 b.
FIG. 3B shows the immunoprecipitation and Western blotting of c-kit in clonal hLSCs, hCSCs, and bone marrow cells (BM). C-kit protein was detected at 145 and 120 kDa. The mature form of the receptor capable of binding to stem cell factor has a molecular weight of 145 kDa.

For additional clonal analysis, c-kit-positive cells were subjected to fluorescence activated cell sorting to place single cells in each well of Terasaki plates or seeded at a limiting dilution (1 cell per 20 mm²). After 3 or 4 weeks, multicellular clones were obtained; cells in the clones continued to express c-kit. Cloning efficiency (measured as the percentage of seeded cells) averaged 1% with both methods (data not shown). Clonal human lung stem cells were essentially all positive for c-kit and negative for epithelial-cell, endothelial cell, and smooth-muscle-cell markers (data not shown). The expression of c-kit was confirmed by means of qRT-PCR assay and Western blotting (FIG. 3A-3B). Messenger RNA (mRNA) transcripts for genes encoding thyroid transcription factor 1 (TTF1, p63, CK5, surfactant protein C [SP-C], Clara cell 10-kD secretory protein [CC10], and the epithelial-cell chloride channel CFTR [cystic fibrosis transmembrane conductance regulator]) were barely detectable, confirming the primitive state of the clonal human lung stem cells.

Figure 4:
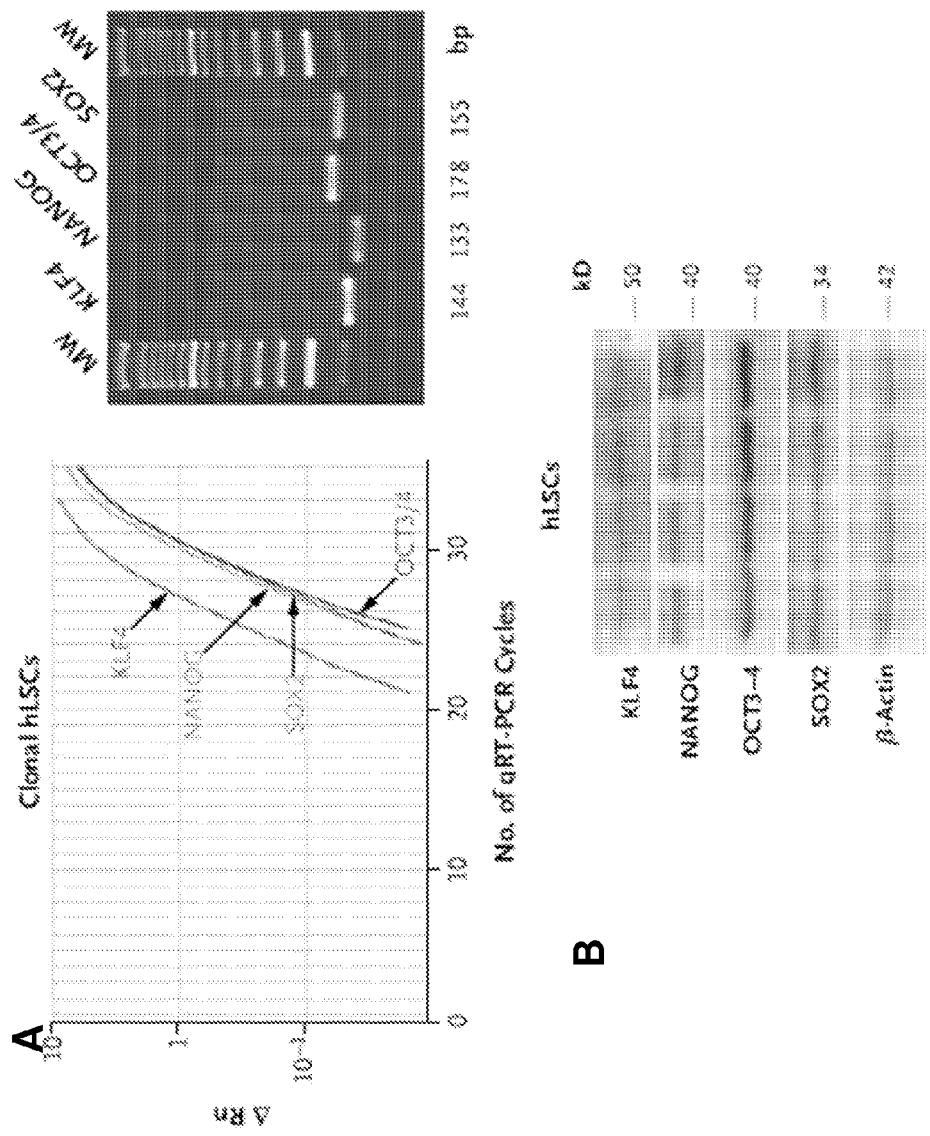
FIG. 4A (left) shows representative results of quantitative reverse-transcriptase-polymerase-chain-reaction (qRT-PCR) assays (with ΔRn indicating the $\log_{10}$-transformed relative number of messenger RNA [mRNA] transcripts) of transcripts for Kruppel-like factor 4 gene (KLF4), the homeobox transcription factor Nanog gene (NANOG), the octamer-binding transcription factor 3-4 gene (OCT3/4), and the sex-determining-region Y-box 2 gene (SOX2) in undifferentiated clonal human lung stem cells. MW denotes molecular-weight DNA ladders. The expression of these four genes in undifferentiated clonal hLSCs is also shown (right), with the transcript sizes shown along the bottom).
FIG. 4B is the Western blot analysis showing the expression of KLF4, NANOG, SOX2, OCT3/4 proteins with the respective protein sizes listed. β-Actin was used as an indicator of equal loading in all lanes.
FIG. 4C shows bivariate-distribution plots (with the x-axis units on a $\log_{in}$ scale and values within each quadrant indicating the mean [±SD] percentage of cells found in each quadrant) of c-kit KLF4, NANOG, OCT3/4, and SOX2 in undifferentiated clonal hLSCs.
Figure 4:
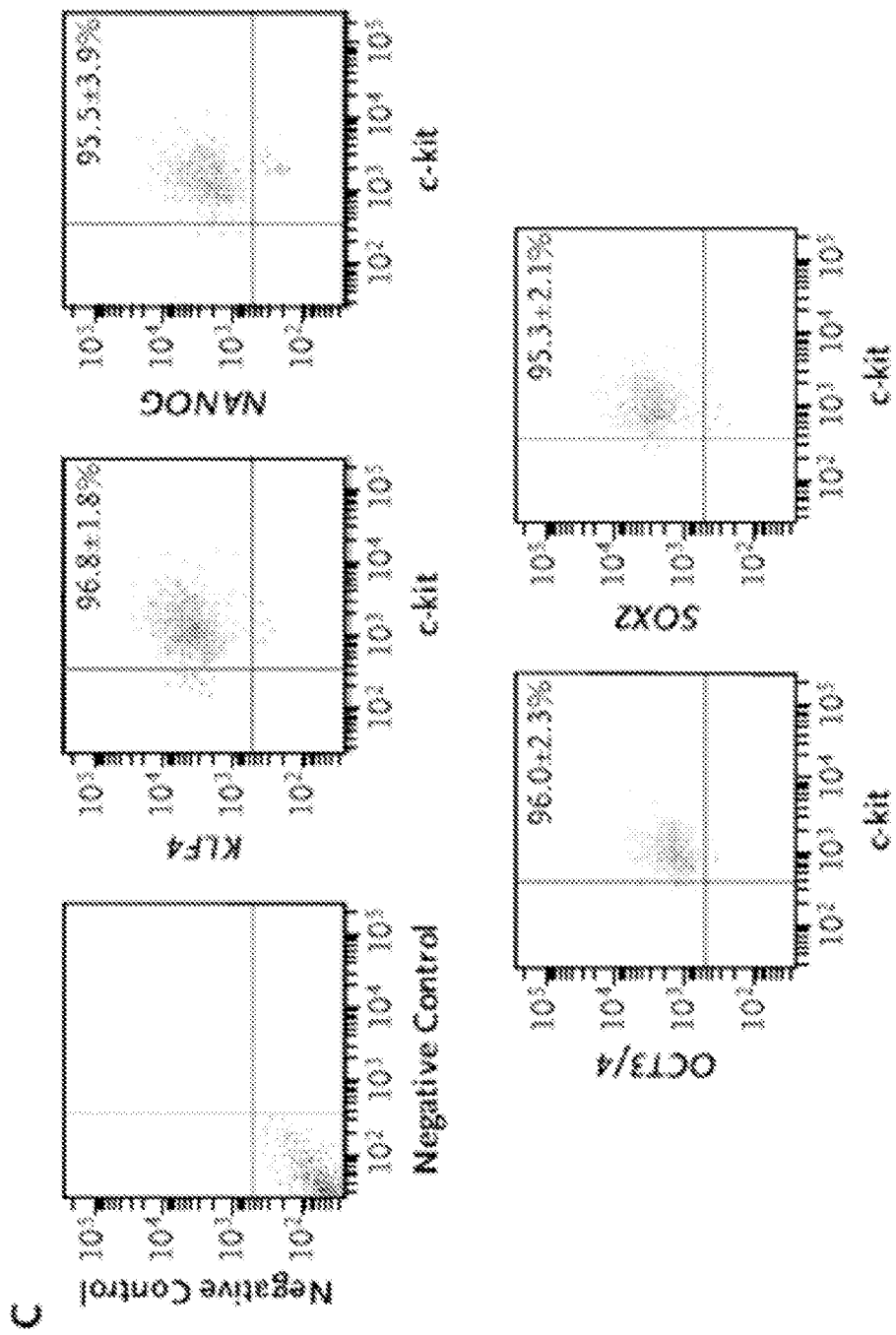

Clonal human lung stem cells exposed to dexamethasone largely lost the c-kit epitope and expressed epithelial and vascular lineage proteins (FIG. 1C). Progressive stages of commitment of epithelial and vascular cells were found, as indicated by morphologic characteristics (FIG. 1D). The presence of c-kit has been used to identify a pool of self-renewing, clonogenic, and multipotent human cardiac stem cells (35) (FIG. 3A). However, human lung stem cells and human cardiac stem cells acquired only cell phenotypes of the organ of origin. Under identical differentiating conditions, human lung stem cells did not generate cardiomyocytes and human cardiac stem cells failed to form lung epithelial cells (data not shown). Collectively, these data indicate that human lung stem cells are distinct from human cardiac stem cells and differentiate into structures of endodermal origin (epithelial cells) and mesodermal origin (vessels). Clonal human lung stem cells express the homeobox transcription factor Nanog (NANOG), octamer-binding transcription factor 3-4 (OCT3/4), sex-determining-region Y-box 2 (SOX2), and Kruppel-like factor 4 (KLF4) (FIG. 4A-4C). The genes encoding these four proteins promote reprogramming of fibroblasts into pluripotent stem cells (41), 16 indicating that adult human lung stem cells are multipotent cells with a high degree of plasticity.

Collectively, these in vitro results support the notion that the human lung harbors a compartment of stem cells which are self-renewing, clonogenic and multipotent. However, the actual documentation of resident hLSCs requires in vivo transplantation assays to establish whether these cells are self-renewing, multipotent and create functionally integrated structures in the lung microenvironment.

Behavior of Clonal and Non-Clonal Human Lung Stem Cells In Vivo

The confirmation of human lung stem cells requires serial transplantation in vivo to establish whether these cells create functionally integrated structures in the relevant tissue microenvironment. To test this possibility, cryoinjury was induced in the left lung of immunosuppressed mice (data not shown). Shortly after lung injury, clonal or nonclonal human lung stem cells were administered in the region adjacent to the area of damage.

These in vivo studies had three objectives. The first was to show that single cell-derived clonal human lung stem cells generate a multicomponent, structurally organized tissue in the recipient mouse lung. This aimed to fulfill the criteria required to prove the function of stem cells in vivo. The second objective was to show that clonal human lung stem cells self-renew in the damaged lung and can be harvested and be re-implanted in another set of animals with lung injury, promoting lung repair. This aimed to mimic the serial transplantation assay commonly used for the analysis of the self-renewal property of hematopoietic stem cells (HSCs). The third objective was to show that non-clonal (non-single-cell-derived), lineage-negative human lung stem cells engraft and form human lung parenchyma in the recipient mouse organ. This aimed to understand the clinical importance of sorted lineage-negative human lung stem cells; it would be unrealistic to use clonal human lung stem cells in patients in view of the low efficiency of clonal formation and the cost of this cell-culture approach.

Figure 5:
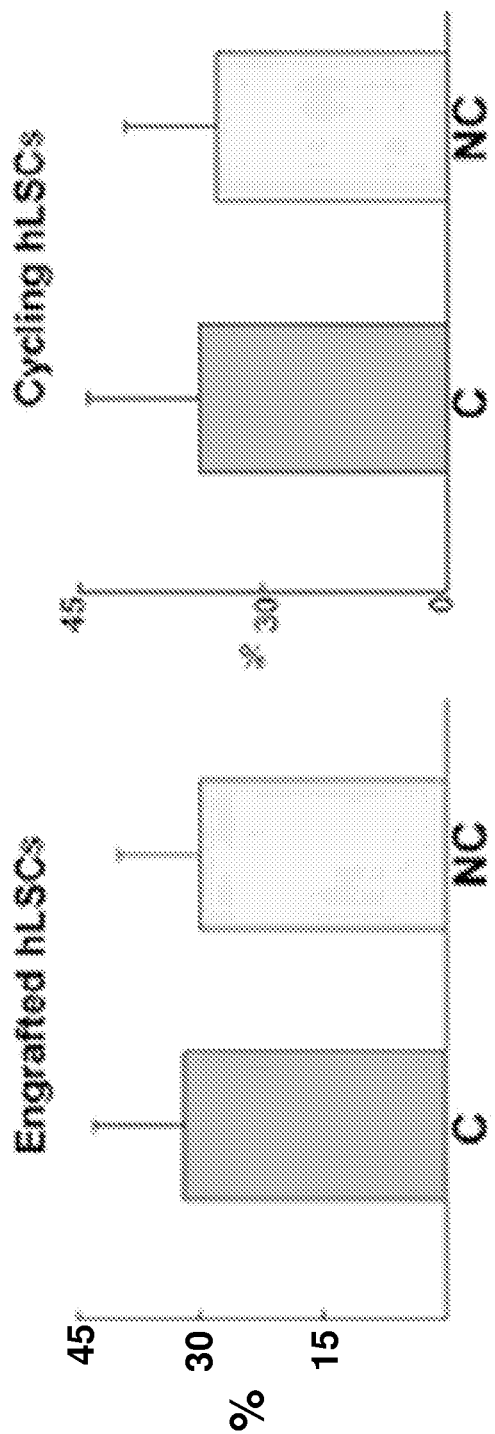
FIG. 5 shows the symmetric and asymmetric division of clonal EGFP-positive hLSCs (green) 2 days after injection in proximity to the injured lung. Data are shown as mean±SD. C, clonal: NC, non-clonal.

Symmetric and asymmetric division of clonal and non-clonal human lung stem cells in vivo was identified 12 to 48 hours after lung injury and cell delivery. The bipolar and unipolar localization of α-adaptin, together with the concurrent expression of TTF1, GATA6, or ETS1, confirmed the ability of human lung stem cells to form new stem cells and cells destined to acquire specialized functions. After 2 days, approximately 30% of the delivered cells were present within the damaged tissue and the bordering region, and approximately 25% were cycling (FIG. 5). After 10 to 14 days, clonal human lung stem cells had formed human bronchioles, alveoli, and pulmonary vessels, partly restoring the structural integrity of the recipient parenchyma (data not shown). Thus, the clonal human lung stem cells showed self-renewal and multipotentiality in vivo. Sorted nonclonal human lung stem cells performed a similar regeneration of the various components of the distal airways and their vasculature (data not shown). The restored EGFP-positive structures were not restricted to the injured portion of the lung.

Figure 6:
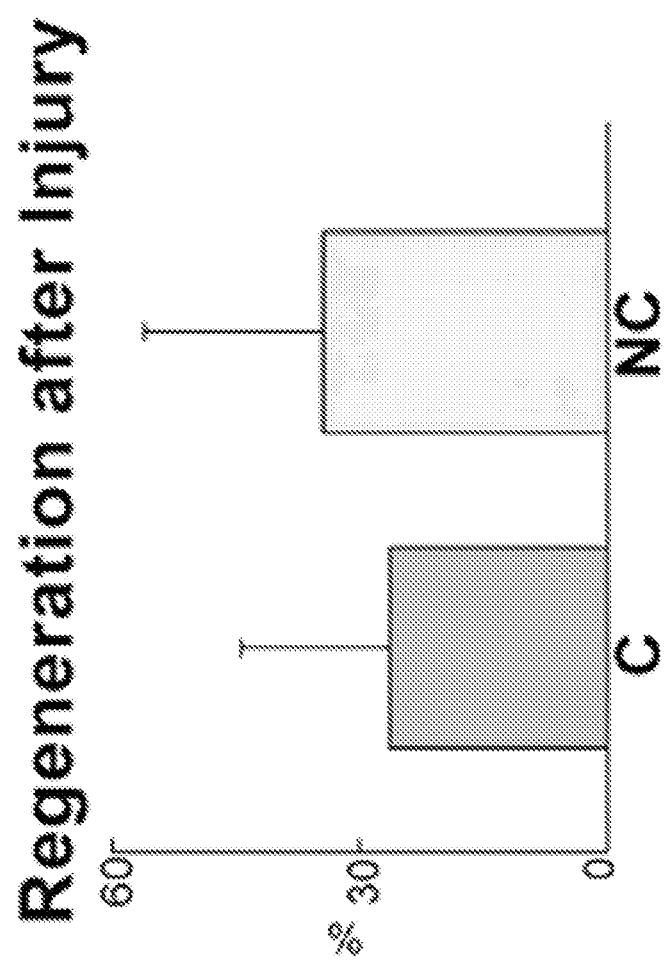
FIG. 6 shows the percent lung regeneration by clonal (C) and non-clonal (NC) hLSCs in the cryo-damaged lungs.

With both clonal and nonclonal human lung stem cells, epithelial cells organized in well-defined alveolar structures were present throughout the affected lobe (data not shown). Human lung stem cells generated bronchioles, approximately 30 to 250 μm in diameter, as well as small and intermediate-sized pulmonary arterioles approximately 20 to 70 μm in diameter (data not shown). Similar degrees of lung repair were found with clonal and nonclonal human lung stem cells, suggesting that these cells had roughly equivalent efficacy. Among both clonal and nonclonal cells, the fraction of epithelial cells labeled by bromodeoxyuridine averaged 90%. The newly formed human lung parenchyma replaced more than 30% of the original damaged tissue (FIG. 6). The specificity of the signal for native and labeled EGFP; pan-cytokeratin (pan-CK); pro-SP-C; SP-C; CC10; aquaporin 5 (AQP5); Alu repeat sequences (Alu); actin, alpha 2, smooth muscle, aorta (ACTA2); and von Willebrand factor (VWF) was validated by means of spectral analysis (data not shown).

Figure 7:
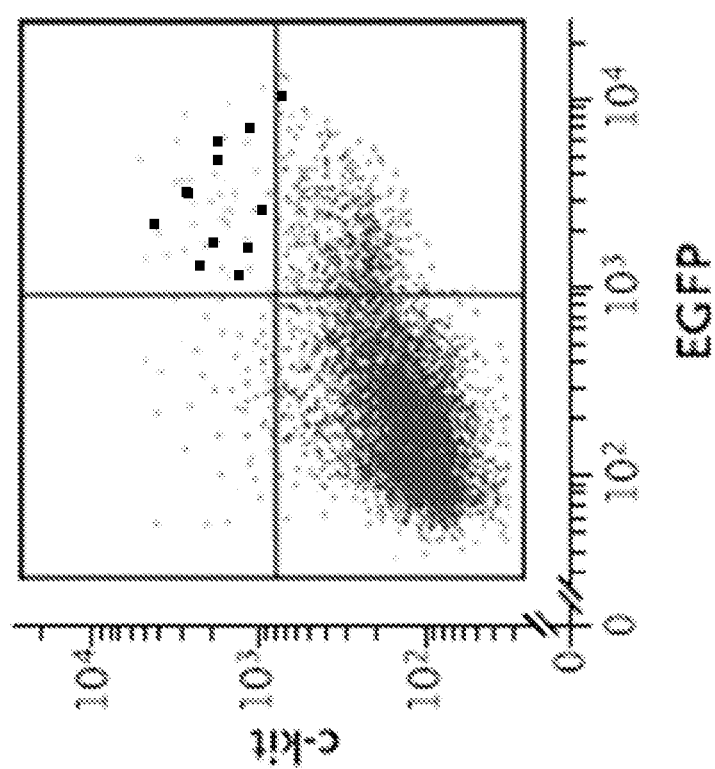
FIG. 7 shows a scatter plot indicating c-kit-positive, EGFP-positive human lung stem cells (big black dots) isolated after lung regeneration after the serial transplantation assay.

Ten to 14 days after cryoinjury and cell implantation, undifferentiated, cycling c-kit-positive human lung stem cells were identified within the regenerated human lung parenchyma and in the adjacent, intact recipient mouse lung (data not shown). Approximately 20,000 human lung stem cells were present in each treated mouse. After enzymatic digestion of the damaged lung, cells were sorted for detection of c-kit and EGFP (FIG. 7) and delivered immediately to the cryoinjured portion of the lung of another recipient mouse. Ten days after cell treatment, all eight treated mice were killed, and human bronchi, alveoli, and vessels were identified, documenting that the newly formed human lung structures derived from the serially transplanted human lung stem cells (data not shown). Undifferentiated, cycling, c-kit-positive human lung stem cells were detected in these mice (data not shown), providing further evidence in support of the self-renewal and long-term proliferation of human lung stem cells in vivo.

The c-kit epitope has been used to identify human cardiac stem cells and hematopoietic stem cells. However, the in vitro progeny of human lung stem cells and human cardiac stem cells are dramatically different, in spite of having the same differentiating conditions (35). In addition, hematopoietic stem cells generate blood cells almost exclusively. To test whether the microenvironment of the mouse lung dictated specific cell phenotypes in vivo, human c-kit-positive hematopoietic stem cells and human cardiac stem cells were delivered to the cryoinjured region of the lung; c-kit-negative human lung cells were used as the control. Ten days after cell administration, a small number of human, undifferentiated hematopoietic stem cells and human cardiac stem cells were found in the damaged area or its proximity (data not shown). Neither type of cells formed human lung structures. No cells were identified after injection of c-kit-negative human lung cells.

Integration of Human Pulmonary Structures

Figure 8:
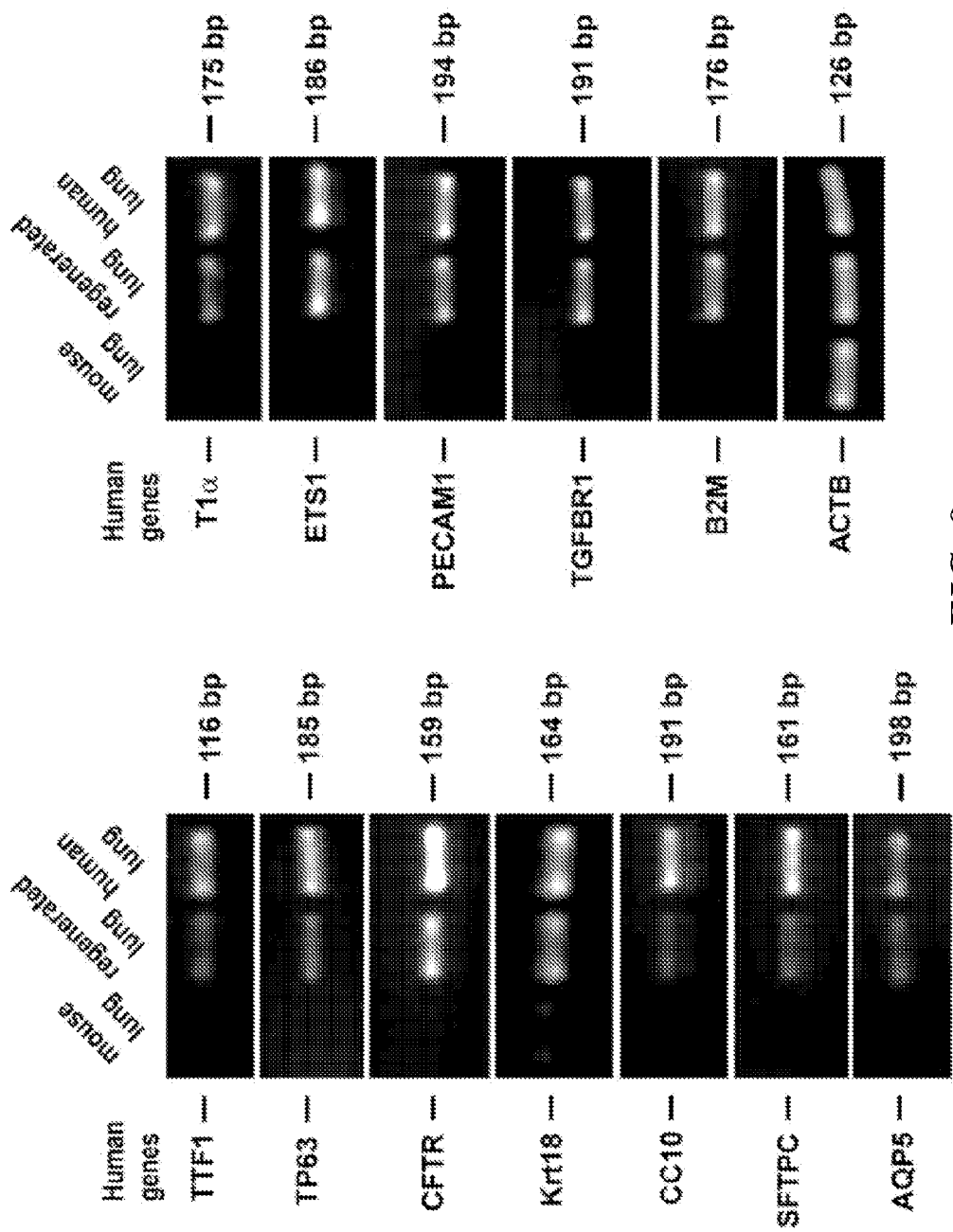
FIG. 8 are gels showing the transcripts of human epithelial cell genes (TTF1, TP63, CFTR, Krt18, CC10, SFTPC, AQP5, T1α), EC genes (ETS1, PECAM1), and SMC gene (TGFBR1). β2-microglobulin (B2M) and β-actin (ACTB) were used as housekeeping genes. ACTB primers identify β-actin in both mouse and human lungs. Additionally, mouse and human lung were used as negative and positive controls, respectively.

Seven to 15 days after cryoinjury and delivery of clonal human lung stem cells, qRT-PCR was used to detect mRNA transcripts for several human epithelial-cell genes (TTF1, TP63 [encoding p63], CFTR, KRT18 [encoding cytokeratin 18], CC10, SFTPC [encoding surfactant protein C], AQP5, and T1A [encoding podoplanin]), endothelial-cell genes (ETS1 and PECAM1 [encoding platelet-endothelial cell adhesion molecule]), and a gene encoding smooth-muscle-cell transforming growth factor β receptor 1 (TGFBR1) (FIG. 8). In addition, fusion events between human lung stem cells and mouse epithelial cells, smooth-muscle cells, and endothelial cells were ruled out through the identification of human and mouse X chromosomes in EGFP-positive bronchioles, alveoli, and pulmonary vessels (data not shown).

Figure 9:
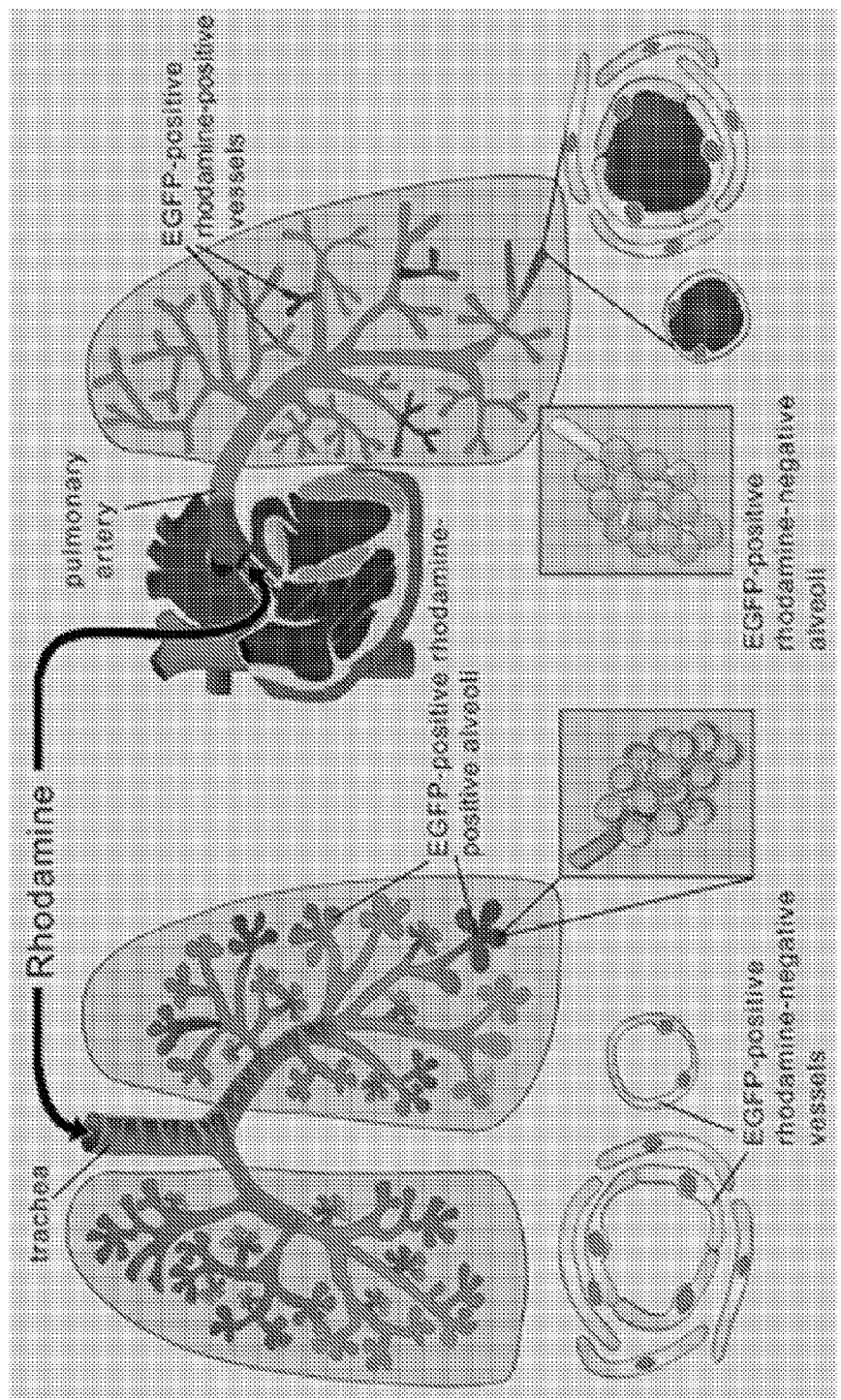
FIG. 9 shows the scheme of ex vivo experiments by two-photon microscopy. In the left part of the scheme, airways were perfused continuously with an oxygenated Tyrode solution containing rhodamine-labeled dextran, which has a MW of 70,000 Da and red fluorescence. Pre-existing mouse alveoli and regenerated human alveoli were identified by the absence and presence of EGFP labeling, respectively. In this preparation, structures positive for EGFP but negative for rhodamine reflected newly formed vessels. In a complementary protocol shown in the right part of the scheme, the pulmonary artery was perfused in an identical manner and pre-existing mouse vessels and regenerated human vessels were identified by the absence and presence of EGFP labeling of the vessel wall, respectively. In this preparation, structures positive for EGFP but negative for rhodamine reflected newly formed alveoli.

To document the integration of human structures with the recipient mouse lung, an ex vivo preparation was used. The mouse lung was examined 10 to 14 days after cryoinjury and the injection of EGFP-positive human lung stem cells. The trachea, bronchi, bronchioles, and alveoli were perfused with rhodamine-labeled dextran to visualize the airways by means of two-photon microscopy (38) (FIG. 9). Resident and regenerated alveoli were distinguished by the absence and presence of EGFP labeling, respectively. EGFP-positive alveoli were found, supporting their origin from the injected human lung stem cells (data not shown). Newly formed alveoli and vessels (EGFP-positive but rhodamine-negative) were in close proximity to each other, a finding that was consistent with the presence of integrated human respiratory domains in the mouse lung.

Perfusion of the pulmonary artery with dextran revealed a relevant number of vascular profiles with EGFP-positive walls, indicating their origin from the delivered human lung stem cells (data not shown). Human vessels and human alveoli (EGFP positive but rhodamine-negative) were in close proximity with one another, reflecting integrated respiratory units involved in gas exchange. Direct connections were found between preexisting pulmonary vessels (EGFP-negative-walled) and regenerated pulmonary vessels (EGFP-positive-walled) (data not shown), documenting the integration of temporally distinct preexisting (mouse) and new (human) segments of the pulmonary vasculature.

Human Lung Stem Cell Niches

Typically, stem cells are located in particular anatomical niches where they are connected to the supporting cells by means of gap junctions and adherens junctions consisting of connexins and cadherins, respectively (15). In 12 adult and 9 fetal human lung-tissue specimens, we found structures with the characteristics of stem-cell niches in bronchioles from 25 to 1200 μm in diameter, as well as within the alveolar wall (data not shown). E-cadherin was detected at the interface between human lung stem cells and epithelial cells, smooth-muscle cells, and fibroblasts, suggesting that the latter three cell types may function as supporting cells in the lung stem-cell niches. The anatomical proximity and structural connections between human lung stem cells and epithelial cells, smooth-muscle cells, and fibroblasts is consistent with the architectural organization of a niche, although the function of these potential supporting cells in the fate of human lung stem cells remains to be defined.

In human bronchioles approximately 1.2 mm in diameter, basal epithelial cells expressed p63 in their nuclei and CK5 in their cytoplasm; and c-kit-positive cells within the basal-cell layer expressed p63 and CK5, suggesting a lineage relationship between human lung stem cells and basal epithelial cells. The basal epithelium also contained c-kit-positive cells negative for p63 and CK5, reflecting uncommitted cells (data not shown); p63-positive and CK5-positive epithelial cells made up 14±4% of bronchiolar epithelial cells.

Progenitor epithelial cells retained the c-kit epitope and expressed TTF1 (16) in the absence of specialized cytoplasmic proteins. Precursor epithelial cells were positive for c-kit, TTF1, and pro-SP-C or cytokeratin. Similarly, progenitor endothelial cells and smooth-muscle cells expressing ETS1 and GATA6, respectively, were identified (data not shown).

Numbers of Human Lung Stem Cells

Figure 10:
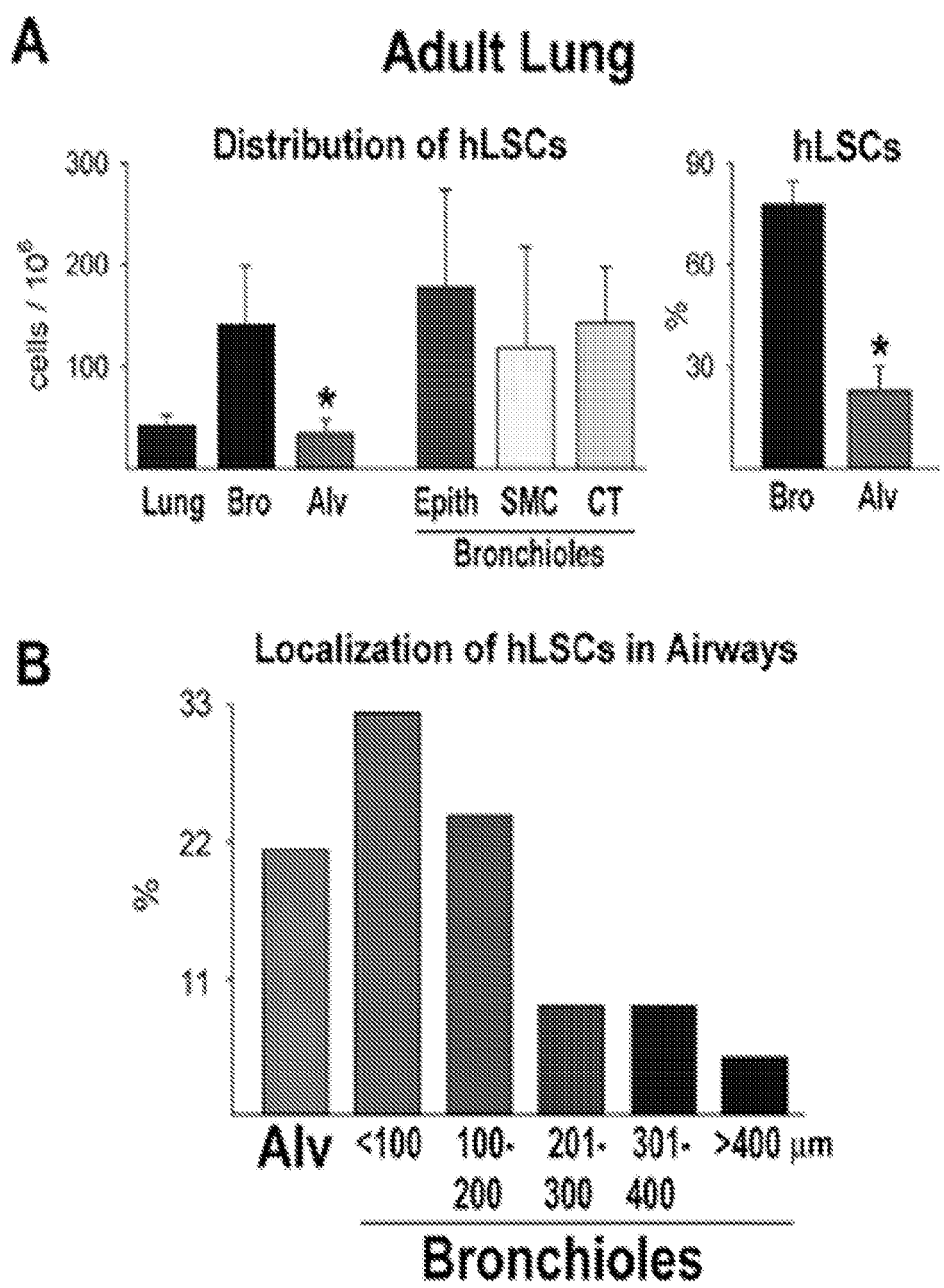
FIG. 10A shows the number and distribution of adult hLSCs. Results are shown as means±SD. *P<0.05 vs. bronchioles (Bro). Alv, alveoli; Epith, epithelial cells; CT, connective tissue.
FIG. 10B shows the distribution of hLSCs in alveoli and bronchioles of different size.

Stem cells are relatively uncommon in solid and nonsolid organs. In humans, there is 1 stem cell per approximately 10,000 to 20,000 cells in the bone marrow and per approximately 30,000 cells in the heart (35, 49). Undifferentiated human lung stem cells negative for nuclear and cytoplasmic proteins of lung cells were found at a frequency of 1 per 24,000 cells; counts in the bronchioles and alveoli were 1 per 6000 cells and 1 per 30,000 cells, respectively. It was estimated that 79% of human lung stem cells were nested in bronchioles and 21% in alveoli (FIG. 10A). Human lung stem cells showed a preferential localization in small bronchioles lacking cartilage and alveoli, decreasing progressively in number in the larger airways (FIG. 10B). Collectively, there were 7700 human lung stem cells per 10 cm3 of collapsed tissue volume.

Figure 11:
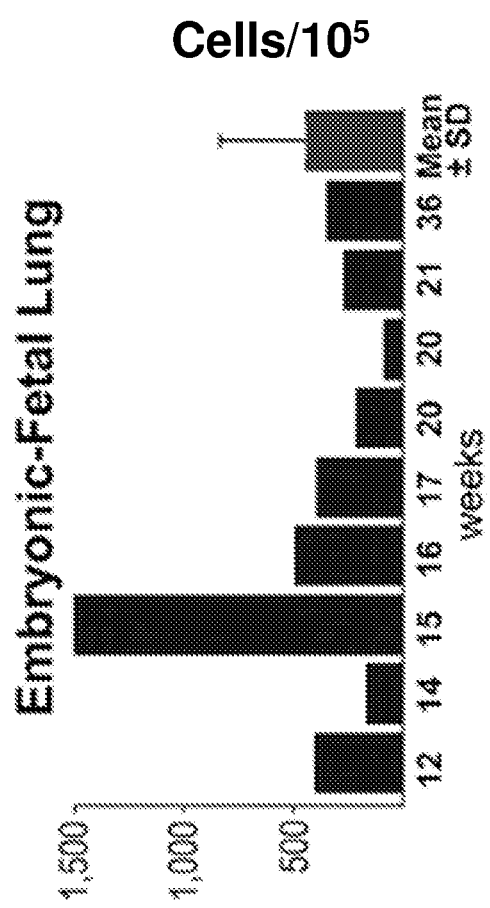
FIG. 11 shows the number of embryonic-fetal hLSCs in the 9 samples examined. Gestational age is indicated in weeks.

The availability of nine samples of fetal lung tissue from 12 to 36 weeks of gestation allowed us to count the number of human lung stem cells during this phase of rapid prenatal growth. The four pluripotency genes NANOG, OCT3/4, SOX2, and KLF4 were also detected in c-kit-positive cells of the fetal human lung (data not shown). Uncommitted human lung stem cells were found in combination with epithelial, endothelial, and smooth-muscle cell progenitors (data not shown), strongly indicating that fetal human lung stem cells acquired the cell phenotypes needed for the generation of functioning lung tissue. The frequency of human lung stem cells varied from 1 per 11,000 cells to 1 per 600 cells in the fetal lung, resulting in an average count of 1 per 4100 cells (FIG. 11).

CONCLUSION

The inventors have shown that the human lung possesses a pool of resident, undifferentiated, hLSCs nested in niches located in proximity of distal airways. These cells were found to be self-renewing, clonogenic and multipotent in vitro and in vivo. After injection in the damaged mouse lung, hLSCs created human bronchioles, alveoli and pulmonary vessels integrated structurally with the recipient organ. The pulmonary repair process mediated by hLSC differentiation occurred independently of fusion events. The formation of a chimeric organ was confirmed by detection of human transcripts for epithelial and vascular genes. The epithelial differentiation of hLSCs was documented further by fate mapping in which the reporter gene was shared by clonogenic hLSCs and the derived type II alveolar epithelial cells. These observations provide strong evidence in favor of the crucial role that hLSCs can have in tissue homeostasis and regeneration following injury. Thus these cells have therapeutic implications, for example, in the regeneration of bronchiolar and alveolar epithelial cells, vascular and non-vascular smooth muscle cells and endothelial cells of the distal airways in humans.

BASCs, Clara cells, SP cells and type II alveolar epithelial cells have been claimed to represent distinct classes of lung progenitor cells (3, 4, 6-10). Although the field of lung stem cell biology is highly controversial, these cell categories have been argued to possess properties commonly attributed to lineage negative undifferentiated cells. This conclusion has been based predominantly on the ability of these cells to enter the cell cycle, divide and contribute to pulmonary repair following extensive airway injury (19). Because of their proliferative capacity, these cells have been viewed as transit amplifying cells. BASCs, Clara cells, SP cells and type II alveolar epithelial cells have well-defined specialized functions which question their inclusion in the progenitor/stem cell category. For example, the committed state of these cells is apparent when the clonogenic property of BASCs is considered. At best, individual BASCs generate small colonies indicating that the founder cell is not a lineage negative clonogenic stem cell but represents a cell that has initiated the terminal differentiation program and is at the end of its proliferative lifespan. The expression of SPC and CC10 in BASCs corroborates this consideration.

Similarly, the assumption that cells that retain the power to replicate (20) may be deemed to be transit amplifying cells can hardly be justified. Fibroblasts divide in vitro and in vivo, form in both conditions an identical progeny and participate in tissue repair of all organs. However, they are not progenitor cells or transit amplifying cells. The lung may have a distinct biology for healing (5), but none of the progenitor cells described so far prior to the present discovery has the critical properties of progenitor/stem cells.

By definition, stem cells give rise to progenitors, precursors and subsequently to transit amplifying cells which constitute the pool of highly proliferating cells in self-renewing organs (21-23). These cells divide and concurrently mature until the adult phenotype is reached and, at times, terminal differentiation is acquired (12, 24). This hierarchical organization of lung stem cell biology has been documented in the present study in which a typical stem cell antigen, c-kit, has been employed to identify resident hLSCs. In a manner similar to bone marrow hematopoietic stem cells and cardiac stem cells (13, 25), hLSCs have been shown here to be negative for lineage markers of the organ of origin. Additionally, hLSCs do not express epitopes of hematopoietic stem cells and mesenchymal stromal cells excluding their potential derivation from the bone marrow. Importantly, clonogenic hLSCs delivered to the damaged mouse lung generate organized structures of the distal airways and vasculature which, together with their in vitro properties, demonstrate the fundamental role that these cells may have in cell turnover and regeneration.

An aspect that has to be emphasized regarding the identification and characterization of resident stem cells in the lung relates to the multipotentiality of these primitive cells. Restoration of damaged tissue necessitates cells capable of forming distal airways and the equally needed distal pulmonary vasculature. One structure only would not reestablish the morphological and functional integrity of the injured parenchyma. Unipotent stem cells with distinct differentiating potential would have to be simultaneously activated to generate functionally-competent gas exchange units. This limitation is shared by BASCs, Clara cells, SP cells and type II alveolar epithelial cells since they generate only type I and type II pneumocytes (3, 4, 6-9) or stromal cells (10). Similarly, bone marrow cells expressing Clara cell secretory protein transdifferentiate and acquire the phenotype of epithelial cell lineages (30), lacking the ability to reconstitute and integrate the various components of the gas exchange unit.

REFERENCES

1. Laugwitz K L, et al., Nature. 2005, 433:647-53.
2. Domian I J, et al. Science. 2009, 326:426-9.
3. Kotton D N, et al., Cell Tissue Res. 2008, 331:145-56.
4. Chen H, et al., Proc Am Thorac Soc. 2009, 6:602-6.
5. Blaisdell C J, et al., Stem Cells. 2009, 27:2263-70.
6. Stripp B R, et al., Proc Am Thorac Soc. 2008, 5:328-33.
7. Kim C F, et al., Cell. 2005, 121:823-35.
8. Rawlins E L, et al., Cell Stem Cell. 2009, 4:525-34.
9. Brody J. S, and Williams M. C. Annu Rev Physiol. 1992, 54:351-71.
10. Giangreco A, et al., Am J. Pathol. 2002, 161:173-82.
11. Orlic D, et al., Blood. 1993, 82:762-70.
12. Beltrami A P, et al., Cell. 2003, 114:763-76.
13. Bearzi C, et al., Proc Natl Acad Sci USA. 2007, 104:14068-73.
14. Pomerantz J, and Blau H M. Nat Cell Biol. 2004, 6:810-6.
15. Xie T. and Li L., Development. 2007, 134:2001-6.
16. Kimura S, et al., Genes Dev. 1996, 10:60-9.
17. Gonczy P., Nat Rev Mol Cell Biol. 2008, 9:355-66.
18. Tillmanns J, et al., Proc Natl Acad Sci USA. 2008, 105:1668-73.
19. Giangreco A, et al., Proc Natl Acad Sci USA. 2009, 106:9286-91.
20. Stevens T, et al., Proc Am Thorac Soc. 2008, 5:783-91.
21. Blanpain C. and Fuchs E. Annu Rev Cell Dev Biol. 2006, 22:339-73.
22. Fuchs E. and Horsley V. Genes Dev. 2008, 22:976-85
23. Leri A., et al., Physiol Rev. 2005, 85:1373-416.
24. Eriksson P S, et al., Nat. Med. 1998, 4:1313-7.
25. Orford K W and Scadden D T. Nat Rev Genet. 2008, 9:115-28
26. Hong K U, et al., Am J. Pathol. 2004, 164:577-88.
27. Snyder J C, et al., J. Pathol. 2009, 217:254-64.
28. Chen X, et al., Mol Biol Cell. 2005, 16:3140-51.
29. Bonner-Weir S and Weir G C. Nat. Biotechnol. 2005, 23:857-61.
30. Wong A P, et al., J Clin Invest. 2009, 119:336-48.
31. Hsieh P C, et al., Nat. Med. 2007, 13:970-4.
32. Hosoda T, et al., Proc Natl Acad Sci USA. 2009, 106:17169-74.
33. Beltrami A P, et al., Cell. 2003, 114:763-76.
34. Linke A, et al., Proc Natl Acad Sci USA. 2005, 102: 8966-71.
35. Bearzi C, et al., Proc Natl Acad Sci USA. 2007, 104:14068-73.
36. Bearzi C, Proc Natl Acad Sci USA. 2009, 106:15885-90.
37. Rota M, et al., Proc Natl Acad Sci USA. 2007, 104: 17783-8.
38. Tillmanns J, et al., Proc Natl Acad Sci USA. 2008, 105:1668-73.
39. Urbanek K, et al., Proc Natl Acad Sci USA. 2006, 103:9226-31.
40. Song Y, et al., Am J. Physiol. 2008, 295:H677-90.
41. Yamanaka S., and Blau H M., Nature 2010, 465:704-12.
42. D'Alessandro D A, et al., Circ. Res. 2009, 105:1128-40.
43. Kajstura J. et al., Circ. Res. 2010, 107:305-15.
44. Kajstura J., et al., Circ. Res. In press, 2010.
45. Gonzalez A., et al., Circ. Res. 2008, 102:597-606.
46. Boni A, et al., Proc Natl Acad Sci USA 2008, 105:15529-34.
47. Urbanek K, et al., Circ Res 2010, 107:429-41.
48. Urbanek K, et al., Circ Res 2005, 97:663-73.
49. Craig W., et al., J Exp Med, 1993; 177:1331-42.

TABLE 1

Standard therapy for some lung diseases.

| Lung disease | Standard therapies |
| --- | --- |
| Chronic obstructive pulmonary diseases (COPD, which include diseases such as emphysema, chronic bronchitis, and asthma) | See below |
| Emphysema (either due to smoking, or alpha 1 anti-trypsin deficiency) | Inhaled bronchodilators, inhaled glucocorticoids, oxygen therapy if severe disease. However none of these therapies are curative or reverse the disease. Replacement with alpha-1 antiprotease if deficient. Ultimately patients with severe progressive disease may be considered for lung transplantation. |
| Chronic bronchitis | Inhaled bronchodilators, inhaled glucocorticoids, oxygen therapy if severe disease. Antibiotics intermittently. However none of these therapies are curative or reverse the disease. Ultimately patients with severe progressive disease may be considered for lung transplantation. |
| Asthma | Inhaled glucocorticoids, inhaled bronchodilators, leukotriene modifiers. |
| Pulmonary fibrosis | No therapy proven to be efficacious-physicians will often try immunosuppressive agents or antioxidants. Supportive care including supplemental oxygen. Ultimately patients with |

TABLE 1-continued

Standard therapy for some lung diseases.

| Lung disease | Standard therapies |
| --- | --- |
| | progressive disease are considered for lung transplantation. |
| Interstitial pneumonias | Therapies include immunosuppressive agents, quit smoking, removal from environmental source. However, if the disease is progressive lung transplant may need to be considered. |
| Other interstitial lung diseases due to a variety of reasons including rheumatologic/immunologic diseases, smoking, exposure to environmental factors, or idiopathic. | |
| Lymphangioleiomyomatosis (LAM) | Hormonal manipulation, Sirolimus, lung transplantation when disease progressive. |
| Cystic fibrosis | Antibiotics, bronchodilators, agents to promote airway clearance of thick secretions, chest physiotherapy, glucocorticoids and supplemental oxygen if severe, and with time patients are often considered for lung transplantation. |
| Sarcoidosis | Immunosuppressive agents. If progressive and not responsive to therapy, consideration for lung transplantation. |
| Pulmonary hypertension | Oral vasodilators (only affective in a minority of patients), Prostanoid formulations (either inhaled or intravenous), endothelin receptor inhibitors, PDE5 inhibitors, combination therapies of the drug classes mentioned, supplemental oxygen, and anticoagulation-unfortunately patients progress and may be considered for lung transplantation. |
| Pulmonary veno-occlusive disease | Vasodilators, immunosuppressives, anticoagulants, and oxygen. Therapy shown to significantly prolong survival is lung transplantation. |
| Obliterative bronchiolitis (OB)-occurs due to rejection after lung transplantation. Even though transplant is definitive therapy for many progressive lung diseases, the 5-year survival is only 50%. | Immunosuppressive agents, patients may require repeat lung transplantation |

What is claimed:

1. A method for ameliorating a symptom, preventing and/or slowing the progression of a respiratory disease resulting in pathological damage to lung or airway architecture and/or alveolar damage or its symptoms in a human subject in need thereof, comprising administering a pharmaceutical composition comprising:
   (a) an isolated population of cells from a human lung tissue, the isolated population of cells is enriched for c-kit positive lung stem cells and is negative for the markers: CD2, CD3, CD6, CD8, CD14, CD16, CD19, CD20, CD24, CD29, CD34, CD44, CD45, CD49d, CD49e, CD66b, CD90, CD105, CD133, glycophorin A, TTF1, p63, pan-cytokeratin, cytokeratin 5, CC10, aquaporin-5, SPC, Est1, vWF1, GATA 6, and alpha-SMA;
   and
   (b) a pharmaceutically acceptable carrier to the subject to ameliorate a symptom, prevent and/or slow the progression of the respiratory disease or its symptoms, wherein the composition comprises at least $10^2$ cells.

2. The method of claim 1, further comprising administering at least one therapeutic agent.

3. The method of claim 1, wherein the population of c-kit positive lung stem cells repairs, reconstitutes and/or generates pulmonary epithelium, pulmonary vasculature/pulmonary endothelium and/or pulmonary alveoli.

4. The method of claim 1, further comprising selecting a subject who is suffering from a lung disorder prior to administering the population enriched for c-kit positive lung stem cells.

5. The method of claim 1, further comprising selecting a subject in need of restoring the structural and functional integrity of a damaged lung prior to administering the cells.

6. The method of claim 1, further comprising selecting a subject in need of treatment, prevention or repair or reconstitution or generation of pulmonary vasculature or pulmonary epithelium, pulmonary endothelium, or pulmonary alveoli prior to administering the cells.

7. The method of claim 1, wherein the administration is intrapulmonary administration, systemic administration, or a combination thereof.

8. The method of claim 7, wherein the intrapulmonary administration is intratracheal or intranasal administration.

* * * * *